US012573495B2

(12) United States Patent
Shelton, IV et al.

(10) Patent No.: US 12,573,495 B2
(45) Date of Patent: Mar. 10, 2026

(54) SURGICAL COMPUTING SYSTEM WITH SUPPORT FOR INTERRELATED MACHINE LEARNING MODELS

(71) Applicant: Cilag GmbH International, Zug (CH)

(72) Inventors: Frederick E. Shelton, IV, Hillsboro, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 147 days.

(21) Appl. No.: 18/092,023

(22) Filed: Dec. 30, 2022

(65) Prior Publication Data

US 2024/0221893 A1     Jul. 4, 2024

(51) Int. Cl.
| | |
|---|---|
| *G16H 20/40* | (2018.01) |
| *G06F 21/62* | (2013.01) |
| *G16H 50/20* | (2018.01) |

(52) U.S. Cl.
CPC ......... *G16H 20/40* (2018.01); *G06F 21/6245* (2013.01); *G16H 50/20* (2018.01)

(58) Field of Classification Search
CPC ........ G16H 10/60; G16H 50/20; G16H 40/67; G16H 40/20; G16H 50/70; G16H 20/40; G06F 21/6245; G06F 21/6254
USPC ........................................................... 705/2
See application file for complete search history.

(56) References Cited

U.S. PATENT DOCUMENTS

| | | | |
|---|---|---|---|
| 6,463,417 | B1 | 10/2002 | Schoenberg |
| 9,345,481 | B2 | 5/2016 | Hall et al. |
| 9,687,230 | B2 | 6/2017 | Leimbach et al. |
| 10,390,895 | B2 | 8/2019 | Henderson et al. |
| 10,695,081 | B2 | 6/2020 | Shelton, IV et al. |
| 10,842,523 | B2 | 11/2020 | Shelton, IV et al. |
| 10,881,399 | B2 | 1/2021 | Shelton, IV et al. |
| 10,932,808 | B2 | 3/2021 | Shelton, IV et al. |
| 11,410,259 | B2 | 8/2022 | Harris et al. |
| 11,423,007 | B2 | 8/2022 | Shelton, IV et al. |
| 11,464,590 | B1 | 10/2022 | Roh et al. |
| 12,165,200 | B1 | 12/2024 | Tilly et al. |
| 2007/0027459 | A1 | 2/2007 | Horvath et al. |

(Continued)

FOREIGN PATENT DOCUMENTS

| | | | |
|---|---|---|---|
| CN | 108430339 A | | 8/2018 |
| CN | 108511057 A | * | 9/2018 ............. G16H 50/20 |
| WO | 2021113168 A1 | | 6/2021 |

OTHER PUBLICATIONS

Alsallal, et al., "A Machine Learning Technique to Detect Counterfeit Medicine Based on X-Ray Fluorescence Analyser", International Conference On Computing, Electronics & Communications Engineering (ICCECE), IEEE, 2018, pp. 118-122.

(Continued)

*Primary Examiner* — Igor N Borissov
(74) *Attorney, Agent, or Firm* — Condo Roccia Koptiw LLP

(57) ABSTRACT

Systems, methods, and instrumentalities are disclosed for a surgical computing system with support for machine learning model interaction. Data exchange behavior between machine learning (ML) models and data storages may be determined and implemented. For example, data exchange may be determined based on privacy implications associated with a ML model and/or data storage. Data exchange may be determined based on processing goals associated with ML models.

15 Claims, 23 Drawing Sheets

(56) References Cited

U.S. PATENT DOCUMENTS

| 2007/0192140 A1 | 8/2007 | Gropper |
| 2008/0285626 A1 | 11/2008 | Ma et al. |
| 2009/0172773 A1 | 7/2009 | Moore |
| 2010/0228222 A1 | 9/2010 | Williams et al. |
| 2011/0112384 A1 | 5/2011 | Eisenhardt et al. |
| 2014/0005743 A1 | 1/2014 | Giuffrida et al. |
| 2014/0263552 A1 | 9/2014 | Hall et al. |
| 2017/0202605 A1 | 7/2017 | Shelton, IV et al. |
| 2017/0296213 A1 | 10/2017 | Swensgard et al. |
| 2017/0360512 A1 | 12/2017 | Couture et al. |
| 2018/0049822 A1 | 2/2018 | Henderson et al. |
| 2018/0360452 A1 | 12/2018 | Shelton, IV et al. |
| 2019/0006047 A1 | 1/2019 | Gorek et al. |
| 2019/0059929 A1 | 2/2019 | Shelton, IV et al. |
| 2019/0104919 A1 | 4/2019 | Shelton, IV et al. |
| 2019/0125455 A1 | 5/2019 | Shelton, IV et al. |
| 2019/0200844 A1 | 7/2019 | Shelton, IV et al. |
| 2019/0200981 A1 | 7/2019 | Harris et al. |
| 2019/0200997 A1 | 7/2019 | Shelton, IV et al. |
| 2019/0201047 A1 | 7/2019 | Yates et al. |
| 2019/0201119 A1 | 7/2019 | Harris et al. |
| 2019/0201123 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201144 A1 | 7/2019 | Shelton, IV et al. |
| 2019/0205441 A1 | 7/2019 | Shelton, IV et al. |
| 2019/0205567 A1 | 7/2019 | Shelton, IV et al. |
| 2019/0206555 A1 | 7/2019 | Morgan et al. |
| 2019/0206562 A1 | 7/2019 | Shelton, IV et al. |
| 2019/0206564 A1 | 7/2019 | Shelton, IV et al. |
| 2019/0206569 A1 | 7/2019 | Shelton, IV et al. |
| 2019/0207857 A1 | 7/2019 | Shelton, IV et al. |
| 2020/0015901 A1 | 1/2020 | Scheib et al. |
| 2020/0237452 A1 | 7/2020 | Wolf et al. |
| 2020/0405296 A1 | 12/2020 | Shelton, IV et al. |
| 2021/0076966 A1 | 3/2021 | Grantcharov et al. |
| 2021/0196384 A1 | 7/2021 | Shelton, IV et al. |
| 2021/0210189 A1 | 7/2021 | Casey et al. |
| 2021/0244487 A1 | 8/2021 | Beck |
| 2021/0315579 A1 | 10/2021 | Shelton, IV et al. |
| 2021/0322014 A1 | 10/2021 | Shelton, IV et al. |
| 2021/0343017 A1 | 11/2021 | Jordan |
| 2021/0344880 A1 | 11/2021 | Katra et al. |
| 2021/0370790 A1 | 12/2021 | Feldman |
| 2022/0039822 A1 | 2/2022 | Huang et al. |
| 2022/0096163 A1 | 3/2022 | Payyavula et al. |
| 2022/0104822 A1 | 4/2022 | Shelton, IV et al. |
| 2022/0233119 A1 | 7/2022 | Shelton, IV et al. |
| 2022/0238216 A1 | 7/2022 | Shelton, IV et al. |
| 2022/0265233 A1* | 8/2022 | Boddington .......... A61B 90/37 |
| 2022/0286687 A1 | 9/2022 | Bishop et al. |
| 2022/0318270 A1 | 10/2022 | Safary et al. |
| 2022/0331047 A1 | 10/2022 | Shelton, IV et al. |
| 2022/0367040 A1 | 11/2022 | Sutherland et al. |
| 2022/0370138 A1 | 11/2022 | Shelton, IV et al. |
| 2022/0392621 A1 | 12/2022 | George et al. |
| 2023/0027978 A1 | 1/2023 | Gaborit et al. |
| 2023/0095002 A1 | 3/2023 | Shelton, IV et al. |
| 2023/0097906 A1 | 3/2023 | Shelton, IV et al. |
| 2023/0098538 A1 | 3/2023 | Shelton, IV et al. |
| 2023/0326193 A1 | 10/2023 | Zia et al. |
| 2023/0352133 A1 | 11/2023 | Chen et al. |
| 2023/0377709 A1 | 11/2023 | Shelton, IV et al. |
| 2024/0024027 A1 | 1/2024 | Shelton et al. |
| 2024/0065550 A1 | 2/2024 | Connor |
| 2024/0112768 A1 | 4/2024 | Shelton, IV et al. |
| 2024/0216065 A1 | 7/2024 | Shelton, IV et al. |
| 2024/0216081 A1 | 7/2024 | Shelton, IV et al. |
| 2024/0220763 A1 | 7/2024 | Shelton, IV et al. |
| 2024/0221878 A1 | 7/2024 | Shelton, IV et al. |
| 2024/0221892 A1 | 7/2024 | Shelton, IV et al. |
| 2024/0221894 A1 | 7/2024 | Shelton, IV et al. |
| 2024/0221895 A1 | 7/2024 | Shelton, IV et al. |
| 2024/0221896 A1 | 7/2024 | Shelton, IV et al. |
| 2024/0221897 A1 | 7/2024 | Shelton, IV et al. |
| 2024/0221923 A1 | 7/2024 | Shelton, IV et al. |
| 2024/0221924 A1 | 7/2024 | Shelton, IV et al. |
| 2024/0221931 A1 | 7/2024 | Shelton, IV et al. |
| 2024/0221937 A1 | 7/2024 | Shelton, IV et al. |
| 2024/0221960 A1 | 7/2024 | Shelton, IV et al. |
| 2024/0265536 A1 | 8/2024 | Watanabe et al. |
| 2024/0346374 A1 | 10/2024 | Ni et al. |
| 2025/0142289 A1 | 5/2025 | Seo et al. |

OTHER PUBLICATIONS

Anonymous, , "Cloud computing", Wikipedia, the free encyclopedia, Dec. 22, 2022, pp. 1-24.

Asadizanjani, et al., "Counterfeit Electronics Detection Using Image Processing and Machine Learning", Journal of Physics Conference Series, vol. 787, 2017, pp. 1-6.

Qayyum, "Secure and Robust Machine Learning for Healthcare: A Survey", IEEE, Reviews In Biomedical Engineering, vol. 14, 2021, 156-180.

"International Search Report and Written Opinion received for PCT Application No. PCT/IB2023/063313", Apr. 5, 2024, 11 pages.

"International Search Report and Written Opinion received for PCT Application No. PCT/IB2023/063314", Jun. 11, 2024, 25 pages.

"International Search Report and Written Opinion received for PCT Application No. PCT/IB2023/063316", Apr. 10, 2024, 12 pages.

"International Search Report and Written Opinion received for PCT Application No. PCT/IB2023/063317", Apr. 25, 2024, 11 pages.

"International Search Report and Written Opinion received for PCT Application No. PCT/IB2023/063320", Mar. 25, 2024, 17 pages.

International Search Report and Written Opinion received for PCT Application No. PCT/IB2023/063321, Apr. 8, 2024, 13 pages.

"International Search Report and Written Opinion received for PCT Application No. PCT/IB2023/063322", Jun. 19, 2024, 20 pages.

"International Search Report and Written Opinion received for PCT Application No. PCT/IB2023/063324", Apr. 10, 2024, 14 pages.

"Invitation to Pay Additional Fees received for PCT Application No. PCT/IB2023/063314", Mar. 22, 2024, 13 pages.

"Invitation to Pay Additional Fees received for PCT Application No. PCT/IB2023/063318", Apr. 12, 2024, 14 pages.

"Invitation to Pay Additional Fees received for PCT Application No. PCT/IB2023/063322", Apr. 16, 2024, 11 pages.

Brownlee, Jason, "Dynamic Ensemble Selection (DES) for Classification in Python—MachineLearningMastery.com", Retrieved from the Internet: URL: https://web.archive.org/web/20221206025245/ https://machinelearningmastery.com/dynamic-ensemble-selection-in-python/ XP093167838, Dec. 6, 2022, pp. 1-3.

ISO 26262-1, "Road Vehicles—Functional Safety—Part 1: Vocabulary", International Organization for Standardization, Edition 2, Dec. 2018, 13 pages.

Zhao, et al., "Tracking-by-detection of Surgical Instruments in Minimally Invasive Surgery via the Convolutional Neural Network Deep Learning-based Method", Computer Assisted Surgery, vol. 22, No. S1, Dec. 2017, 11 pages.

* cited by examiner

750

SURGICAL COMPUTING SYSTEM WITH SUPPORT FOR INTERRELATED MACHINE LEARNING MODELS

CROSS-REFERENCE TO RELATED APPLICATIONS

This application is related to the following, filed contemporaneously, the contents of each of which are incorporated by reference herein:

U.S. application Ser. No. 18/092,025, titled A METHOD FOR ADVANCED ALGORITHM SUPPORT, U.S. application Ser. No. 18/092,015, titled SURGICAL COMPUTING SYSTEM WITH SUPPORT FOR INTERRELATED MACHINE LEARNING MODELS, U.S. application Ser. No. 18/092,019, titled SURGICAL COMPUTING SYSTEM WITH SUPPORT FOR MACHINE LEARNING MODEL INTERACTION.

BACKGROUND

Patient care is generally improved when tailored to the individual. Every person has different needs, so surgical and interventional solutions that center on the unique journey of every patient may represent efficient, groundbreaking pathways to healing. At the same time, the high stakes of patient care, in particular surgical processes, often drive a focus on conservative, repeatable activities.

Innovative medical technology, such as advanced surgical support computing systems and intelligent surgical instruments for example, may improve approaches to patient care and address the particular needs of health care providers.

The ever-increasing availability data and computing resources have made non-traditional algorithms, such as machine learning algorithms, a specific technical opportunity in health care systems. But incorporating such non-traditional algorithms into any medical technology presents many challenges.

SUMMARY

Systems, methods, and instrumentalities are disclosed for a surgical computing system with support for machine learning model interaction. Data exchange behavior between machine learning (ML) models and data storages may be determined and implemented. For example, data exchange may be determined based on privacy implications associated with a ML model and/or data storage. Data exchange may be determined based on processing goals associated with ML models.

For example, a surgical computing system may determine data exchange behaviors for ML models and processing systems. The surgical computing system may obtain surgical data. The surgical data may include subsets of surgical data. The subsets of surgical data may be associated with respective classifications (e.g., privacy classifications). For example, the respective classifications may be determined for each of the subsets of surgical data. The surgical computing system may determine processing goal(s) associated with processing systems (e.g., ML models), for example, in a hierarchy. The hierarchy may include multiple processing systems in a level-based system. The higher processing systems in the hierarchy may process non-private data. The lower processing systems may use increasingly more private data.

The surgical computing system may determine classification threshold associated with processing tasks associated with the ML models (e.g., processing systems). The processing tasks may include data preparation, reduction, analysis, and/or the like. The surgical computing system may determine whether a subset of data is above or below the classification threshold. The surgical computing system may determine data packages to send to the ML models. The data packages may be determined based on the classification threshold, processing goals, data needs, and/or the like, associated with the ML models. For example, a data package may refrain from including data that is below (e.g., or above) the classification threshold.

The classification threshold may be associated with a privacy level. For example, privacy may be balanced with processing task importance to determine data exchange and data packages. For example, private data may be refrained from being sent to a processing system associated with a minimally important processing task. However, private data may be sent to a processing system associated with an important processing task.

DETAILED DESCRIPTION

Figure 1:
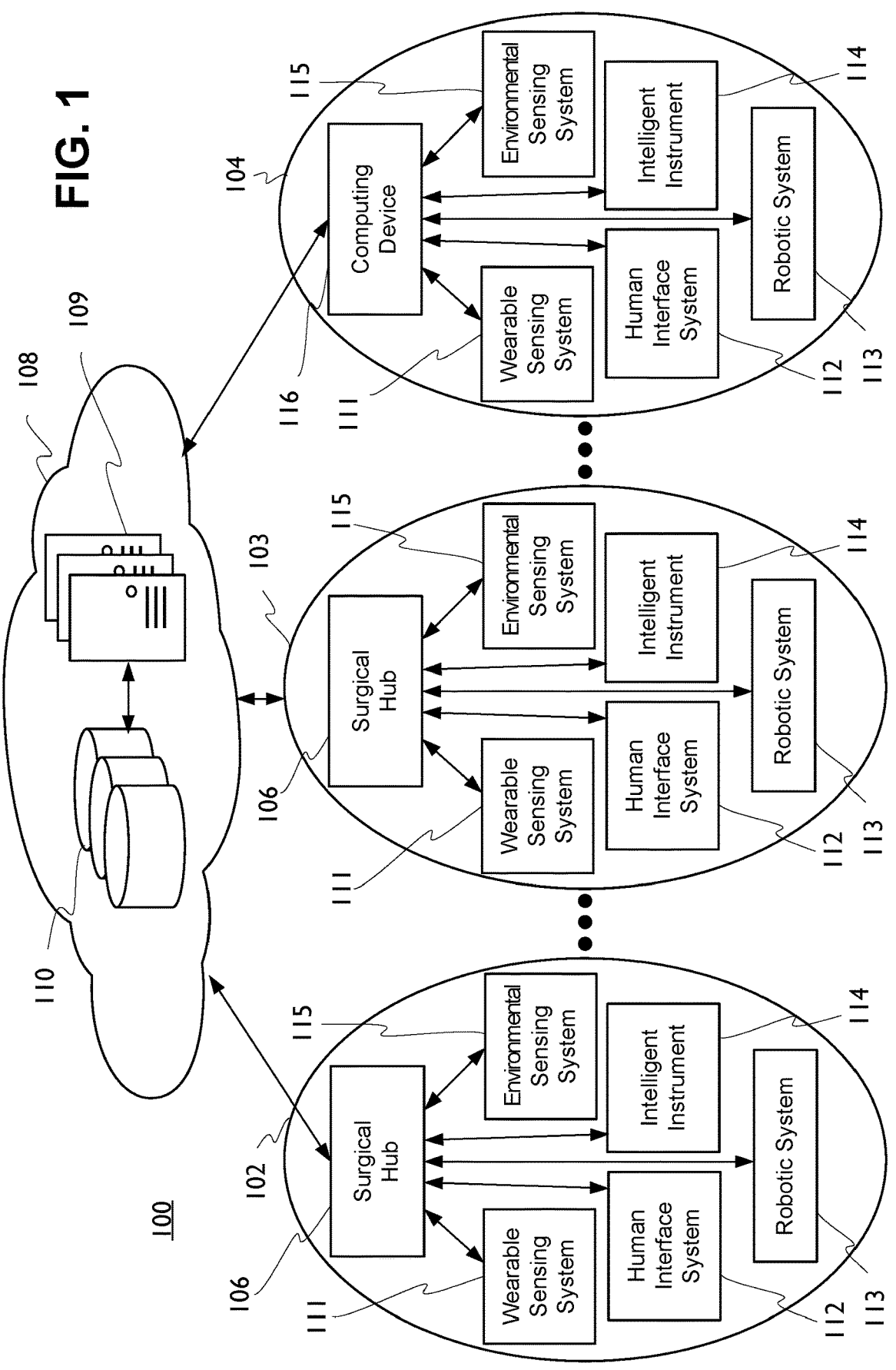
FIG. 1 is a block diagram of a computer-implemented surgical system.

FIG. 1 is a block diagram of a computer-implemented surgical system 100. An example surgical system, such as the surgical system 100, may include one or more surgical systems (e.g., surgical sub-systems) 102, 103, 104. For example, surgical system 102 may include a computer-implemented interactive surgical system. For example, surgical system 102, 103, 104 may include a surgical computing system, such as surgical hub 106 and/or computing device 116, in communication with a cloud computing system 108. The cloud computing system 108 may include a cloud server 109 and a cloud storage unit 110.

Surgical systems 102, 103, 104 may each computer-enabled surgical equipment and devices. For example, surgical systems 102, 103, 104 may include a wearable sensing system 111, a human interface system 112, a robotic system 113, one or more intelligent instruments 114, environmental sensing system 115, and/or the like. The wearable sensing system 111 may include one or more devices used to sense aspects of individuals status and activity within a surgical environment. For example, the wearable sensing system 111 may include health care provider sensing systems and/or patient sensing systems.

The human interface system 112 may include devices that enable an individual to interact with the surgical system 102, 103, 104 and/or the cloud computing system 108. The human interface system 112 may include a human interface device.

The robotic system 113 may include surgical robotic devices, such a surgical robot. The robotic system 113 may enable robotic surgical procedures. The robotic system 113 may receive information, settings, programming, controls and the like from the surgical hub 106 for example, the robotic system 113 may send data, such as sensor data, feedback information, video information, operational logs, and the like to the surgical hub 106.

Figure 2:
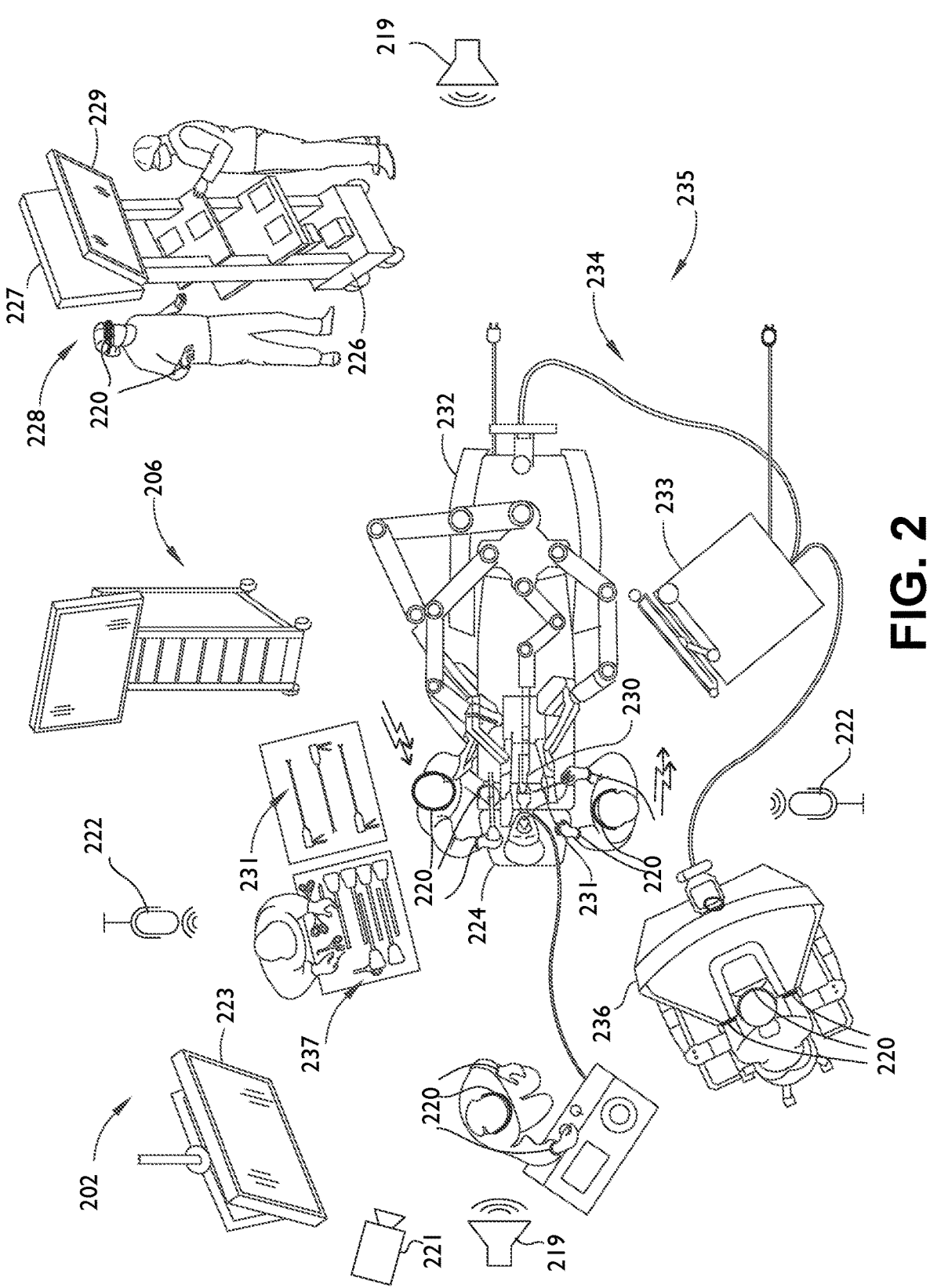
FIG. 2 shows an example surgical system in a surgical operating room.

The environmental sensing system 115 may include one or more devices, for example, used for measuring one or more environmental attributes, for example, as further described in FIG. 2. The robotic system 113 may include a plurality of devices used for performing a surgical procedure, for example, as further described in FIG. 2.

The surgical system 102 may be in communication with a remote server 109 that may be part of a cloud computing system 108. In an example, the surgical system 102 may be in communication with a remote server 109 via networked connection, such an internet connection (e.g., business internet service, T3, cable/FIOS networking node, and the like). The surgical system 102 and/or a component therein may communicate with the remote servers 109 via a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G.

In an example, the surgical hub 106 may facilitate displaying the image from an surgical imaging device, like a laparoscopic scope for example. The surgical hub 106 have cooperative interactions with the other local systems to facilitate displaying information relevant to those local systems. The surgical hub 106 may interact with one or more sensing systems 111, 115, one or more intelligent instruments 114, and/or multiple displays. For example, the surgical hub 106 may be configured to gather measurement data from the one or more sensing systems 111, 115 and send notifications or control messages to the one or more sensing systems 111, 115. The surgical hub 106 may send and/or receive information including notification information to and/or from the human interface system 112. The human interface system 112 may include one or more human interface devices (HIDs). The surgical hub 106 may send and/or receive notification information or control information to audio, display and/or control information to various devices that are in communication with the surgical hub.

For example, the sensing systems 111, 115 may include the wearable sensing system 111 (which may include one or more HCP sensing systems and one or more patient sensing systems) and the environmental sensing system 115. The one or more sensing systems 111, 115 may measure data relating to various biomarkers. The one or more sensing systems 111, 115 may measure the biomarkers using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The one or more sensors may measure the biomarkers as described herein using one of more of the following sensing technologies: photoplethysmography, electrocardiography, electroencephalography, colorimetry, impedimentary, potentiometry, amperometry, etc.

The biomarkers measured by the one or more sensing systems 111, 115 may include, but are not limited to, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle.

The biomarkers may relate to physiologic systems, which may include, but are not limited to, behavior and psychology, cardiovascular system, renal system, skin system, nervous system, gastrointestinal system, respiratory system, endocrine system, immune system, tumor, musculoskeletal system, and/or reproductive system. Information from the biomarkers may be determined and/or used by the computer-implemented patient and the surgical system 100, for example. The information from the biomarkers may be determined and/or used by the computer-implemented patient and the surgical system 100 to improve said systems and/or to improve patient outcomes, for example. The one or more sensing systems 111, 115, biomarkers, and physiological systems are described in more detail in U.S. application Ser. No. 17/156,287, titled METHOD OF ADJUSTING A SURGICAL PARAMETER BASED ON BIOMARKER MEASUREMENTS, filed Jan. 22, 2021, the disclosure of which is herein incorporated by reference in its entirety.

FIG. 2 shows an example of a surgical system 202 in a surgical operating room. As illustrated in FIG. 2, a patient is being operated on by one or more health care professionals (HCPs). The HCPs are being monitored by one or more HCP sensing systems 220 worn by the HCPs. The HCPs and the environment surrounding the HCPs may also be monitored by one or more environmental sensing systems including, for example, a set of cameras 221, a set of microphones 222, and other sensors that may be deployed in the operating room. The HCP sensing systems 220 and the environmental sensing systems may be in communication with a surgical hub 206, which in turn may be in communication with one or more cloud servers 209 of the cloud computing system 208, as shown in FIG. 1. The environmental sensing systems may be used for measuring one or more environmental attributes, for example, HCP position in the surgical theater, HCP movements, ambient noise in the surgical theater, temperature/humidity in the surgical theater, etc.

As illustrated in FIG. 2, a primary display 223 and one or more audio output devices (e.g., speakers 219) are positioned in the sterile field to be visible to an operator at the operating table 224. In addition, a visualization/notification tower 226 is positioned outside the sterile field. The visualization/notification tower 226 may include a first non-sterile human interactive device (HID) 227 and a second non-sterile HID 229, which may face away from each other. The HID may be a display or a display with a touchscreen allowing a human to interface directly with the HID. A human interface system, guided by the surgical hub 206, may be configured to utilize the HIDs 227, 229, and 223 to coordinate information flow to operators inside and outside the sterile field. In an example, the surgical hub 206 may cause an HID (e.g., the primary HID 223) to display a notification and/or information about the patient and/or a surgical procedure step. In an example, the surgical hub 206 may prompt for and/or receive input from personnel in the sterile field or in the non-sterile area. In an example, the surgical hub 206 may cause an HID to display a snapshot of a surgical site, as recorded by an imaging device 230, on a non-sterile HID 227 or 229, while maintaining a live feed of the surgical site on the primary HID 223. The snapshot on the non-sterile display 227 or 229 can permit a non-sterile operator to perform a diagnostic step relevant to the surgical procedure, for example.

In one aspect, the surgical hub 206 may be configured to route a diagnostic input or feedback entered by a non-sterile operator at the visualization tower 226 to the primary display 223 within the sterile field, where it can be viewed by a sterile operator at the operating table. In one example, the input can be in the form of a modification to the snapshot displayed on the non-sterile display 227 or 229, which can be routed to the primary display 223 by the surgical hub 206.

Referring to FIG. 2, a surgical instrument 231 is being used in the surgical procedure as part of the surgical system 202. The hub 206 may be configured to coordinate information flow to a display of the surgical instrument 231. For example, in U.S. Patent Application Publication No. US 2019-0200844 A1 (U.S. patent application Ser. No. 16/209, 385), tided METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 226 can be routed by the hub 206 to the surgical instrument display within the sterile field, where it can be viewed by the operator of the surgical instrument 231. Example surgical instruments that are suitable for use with the surgical system 202 are described under the heading "Surgical Instrument Hardware" and in U.S. Patent Application Publication No. US 2019-0200844 A1 (U.S. patent application Ser. No. 16/209,385), tided METHOD OF HUB COMMUNICA-TION, PROCESSING, STORAGE AND DISPLAY, filed Dec. 4, 2018, the disclosure of which is herein incorporated by reference in its entirety, for example.

FIG. 2 illustrates an example of a surgical system 202 being used to perform a surgical procedure on a patient who is lying down on an operating table 224 in a surgical operating room 235. A robotic system 234 may be used in the surgical procedure as a part of the surgical system 202. The robotic system 234 may include a surgeon's console 236, a patient side cart 232 (surgical robot), and a surgical robotic hub 233. The patient side cart 232 can manipulate at least one removably coupled surgical tool 237 through a minimally invasive incision in the body of the patient while the surgeon views the surgical site through the surgeon's console 236. An image of the surgical site can be obtained by a medical imaging device 230, which can be manipulated by the patient side cart 232 to orient the imaging device 230. The robotic hub 233 can be used to process the images of the surgical site for subsequent display to the surgeon through the surgeon's console 236.

Other types of robotic systems can be readily adapted for use with the surgical system 202. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud computing system 208, and are suitable for use with the present disclosure, are described in U.S. Patent Application Publication No. US 2019-0206569 A1 (U.S. patent application Ser. No. 16/209,403), tided METHOD OF CLOUD BASED DATA ANALYTICS FOR USE WITH THE HUB, filed Dec. 4, 2018, the disclosure of which is herein incorporated by reference in its entirety.

In various aspects, the imaging device 230 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 230 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is the portion of the electromagnetic spectrum that is visible to (i.e., can be detected by) the human eye and may be referred to as visible light or simply light. A typical human eye will respond to wavelengths in air that range from about 380 nm to about 750 nm.

The invisible spectrum (e.g., the non-luminous spectrum) is the portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), micro-wave, and radio electromagnetic radiation. Wavelengths less than about 380 nm are shorter than the violet spectrum, and they become invisible ultraviolet, x-ray, and gamma ray electromagnetic radiation.

In various aspects, the imaging device 230 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and uretero-scope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information that the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 230 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Wearable sensing system 211 illustrated in FIG. 1 may include one or more sensing systems, for example, HCP sensing systems 220 as shown in FIG. 2. The HCP sensing systems 220 may include sensing systems to monitor and detect a set of physical states and/or a set of physiological states of a healthcare personnel (HCP). An HCP may be a surgeon or one or more healthcare personnel assisting the surgeon or other healthcare service providers in general. In an example, a sensing system 220 may measure a set of biomarkers to monitor the heart rate of an HCP. In an example, a sensing system 220 worn on a surgeon's wrist (e.g., a watch or a wristband) may use an accelerometer to detect hand motion and/or shakes and determine the magnitude and frequency of tremors. The sensing system 220 may send the measurement data associated with the set of biomarkers and the data associated with a physical state of the surgeon to the surgical hub 206 for further processing. One or more environmental sensing devices may send environmental information to the surgical hub 206. For example, the environmental sensing devices may include a camera 221 for detecting hand/body position of an HCP. The environmental sensing devices may include microphones 222 for measuring the ambient noise in the surgical theater. Other environmental sensing devices may include devices, for example, a thermometer to measure temperature and a hygrometer to measure humidity of the surroundings in the surgical theater, etc. The surgical hub 206, alone or in communication with the cloud computing system, may use the surgeon biomarker measurement data and/or environmental sensing information to modify the control algorithms of hand-held instruments or the averaging delay of a robotic interface, for example, to minimize tremors. In an example, the HCP sensing systems 220 may measure one or more surgeon biomarkers associated with an HCP and send the measurement data associated with the surgeon biomarkers to the surgical hub 206. The HCP sensing systems 220 may use one or more of the following RF protocols for communicating with the surgical hub 20006: Bluetooth, Bluetooth Low-Energy (BLE), Bluetooth Smart, Zigbee, Z-wave, IPv6 Low-power wireless Personal Area Network (6LoWPAN), Wi-Fi. The surgeon biomarkers may include one or more of the following: stress, heart rate, etc. The environmental measurements from the surgical theater may include ambient noise level associated with the surgeon or the patient, surgeon and/or staff movements, surgeon and/or staff attention level, etc.

The surgical hub 206 may use the surgeon biomarker measurement data associated with an HCP to adaptively control one or more surgical instruments 231. For example, the surgical hub 206 may send a control program to a surgical instrument 231 to control its actuators to limit or compensate for fatigue and use of fine motor skills. The surgical hub 206 may send the control program based on situational awareness and/or the context on importance or criticality of a task. The control program may instruct the instrument to alter operation to provide more control when control is needed.

Figure 3:
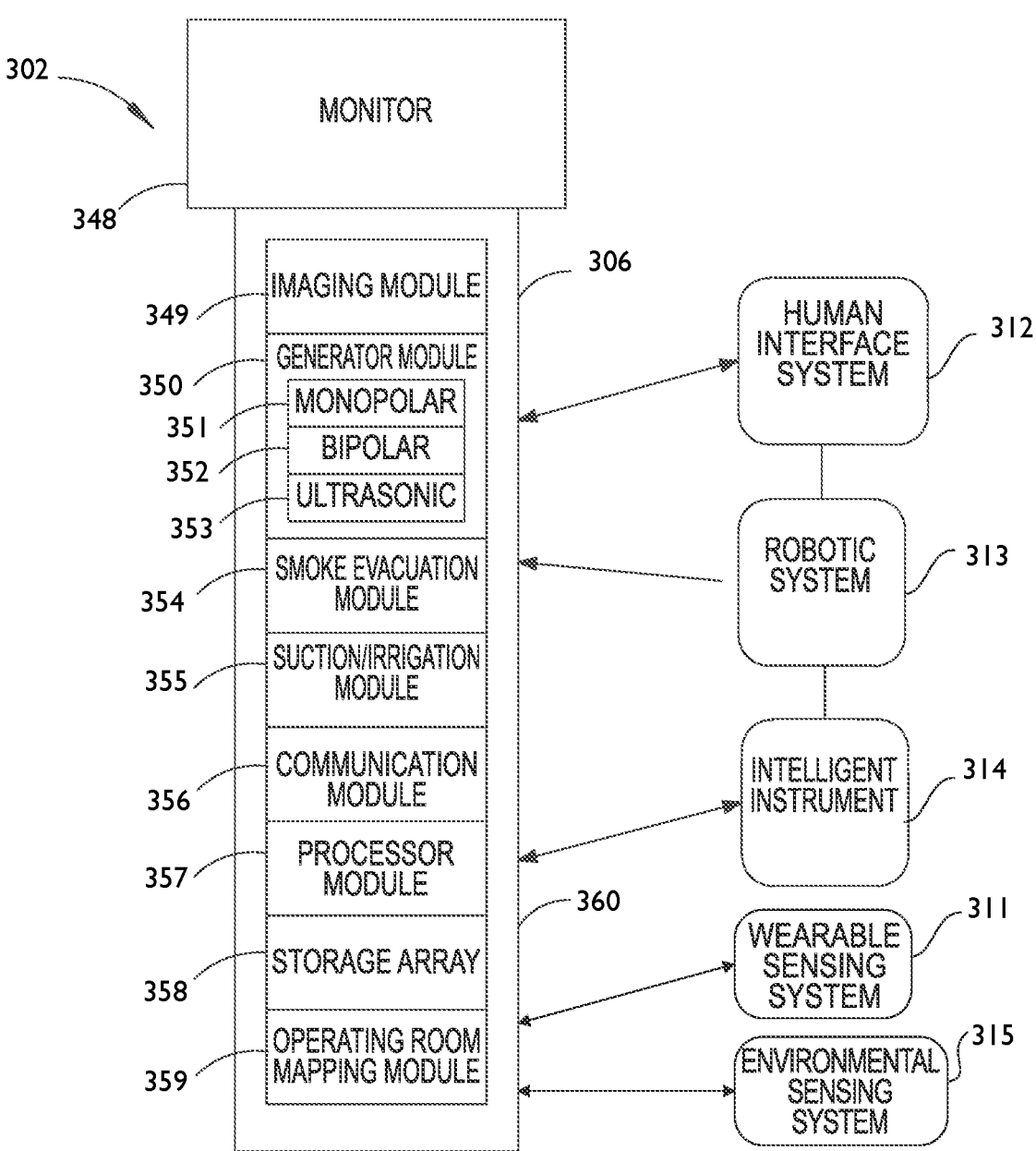
FIG. 3 illustrates an example surgical hub paired with various systems.

FIG. 3 shows an example surgical system 302 with a surgical hub 306. The surgical hub 306 may be paired with, via a modular control, a wearable sensing system 311, an environmental sensing system 315, a human interface system 312, a robotic system 313, and an intelligent instrument 314. The hub 306 includes a display 348, an imaging module 349, a generator module 350, a communication module 356, a processor module 357, a storage array 358, and an operating-room mapping module 359. In certain aspects, as illustrated in FIG. 3, the hub 306 further includes a smoke evacuation module 354 and/or a suction/irrigation module 355. The various modules and systems may be connected to the modular control either directly via a router or via the communication module 356. The operating theater devices may be coupled to cloud computing resources and data storage via the modular control. The human interface system 312 may include a display sub-system and a notification sub-system.

The modular control may be coupled to non-contact sensor module. The non-contact sensor module may measure the dimensions of the operating theater and generate a map of the surgical theater using, ultrasonic, laser-type, and/or the like, non-contact measurement devices. Other distance sensors can be employed to determine the bounds of an operating room. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety. The sensor module may be configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 360 offers a unified environment for managing the power, data, and fluid lines, which reduces the frequency of entanglement between such lines. Aspects of the present disclosure present a surgical hub 306 for use in a surgical procedure that involves energy application to tissue at a surgical site.

The surgical hub 306 includes a hub enclosure 360 and a combo generator module slidably receivable in a docking station of the hub enclosure 360. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line may be a first fluid line, and a second fluid line may extend from the remote surgical site to a suction and irrigation module 355 slidably received in the hub enclosure 360. In one aspect, the hub enclosure 360 may include a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 360 is configured to accommodate different generators and facilitate an interactive communication therebetween. The hub modular enclosure 360 may enable the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 360 that allows the modular integration of a generator module 350, a smoke evacuation module 354, and a suction/irrigation module 355. The hub modular enclosure 360 further facilitates interactive communication between the modules 359, 354, and 355. The generator module 350 can be with integrated monopolar, bipolar, and ultrasonic components supported in a single housing unit slidably insertable into the hub modular enclosure 360. The generator module 350 can be configured to connect to a monopolar device 351, a bipolar device 352, and an ultrasonic device 353. Alternatively, the generator module 350 may comprise a series of monopolar, bipolar, and/or ultrasonic generator modules that interact through the hub modular enclosure 360. The hub modular enclosure 360 can be configured to facilitate the insertion of multiple generators and interactive communication between the generators docked into the hub modular enclosure 360 so that the generators would act as a single generator.

Figure 4:
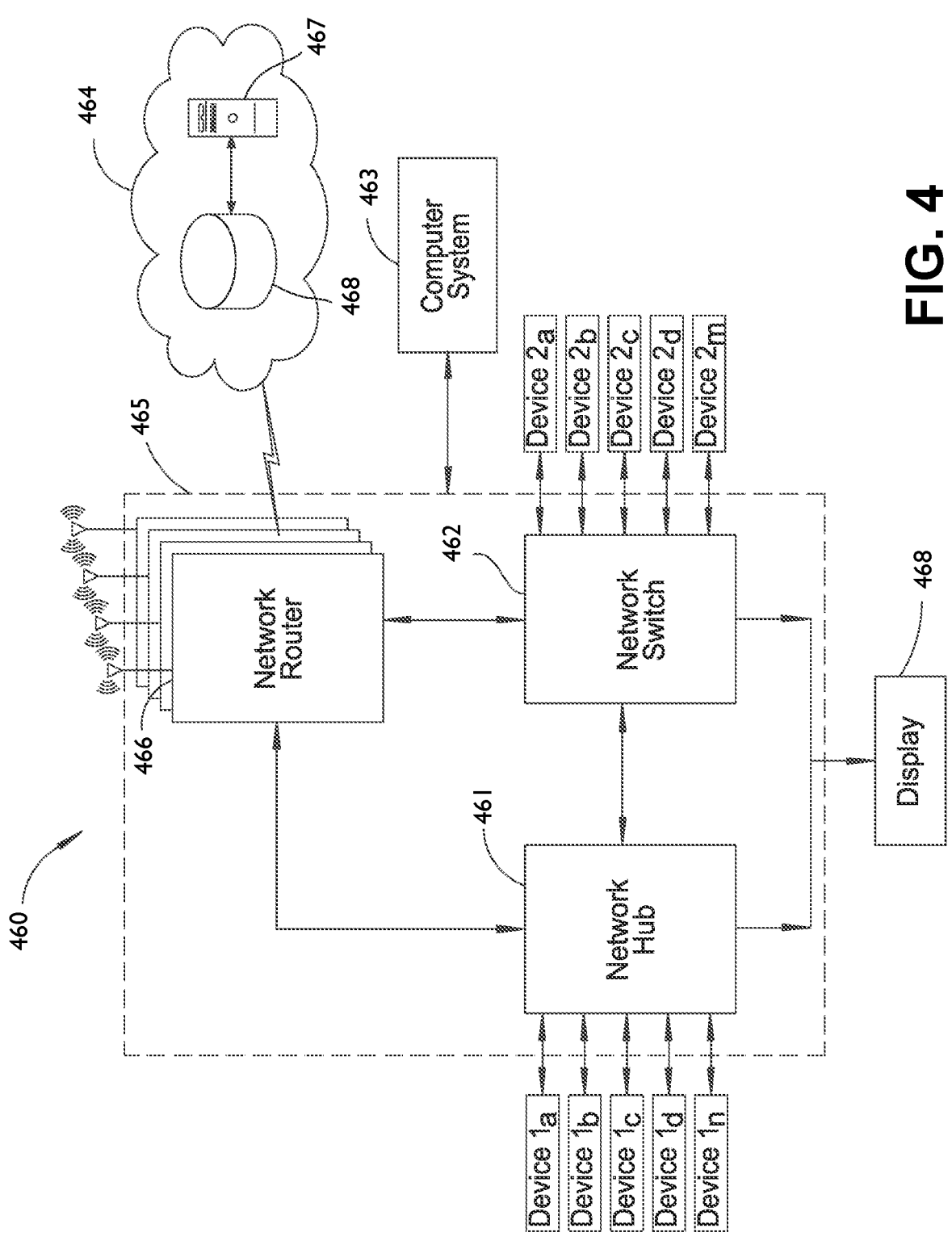
FIG. 4 illustrates a surgical data network having a set of communication surgical hubs configured to connect with a set of sensing systems, an environmental sensing system, a set of devices, etc.

FIG. 4 illustrates a surgical data network having a set of communication hubs configured to connect a set of sensing systems, environment sensing system(s), and a set of other modular devices located in one or more operating theaters of a healthcare facility, a patient recovery room, or a room in a healthcare facility specially equipped for surgical operations, to the cloud, in accordance with at least one aspect of the present disclosure.

As illustrated in FIG. 4, a surgical hub system 460 may include a modular communication hub 465 that is configured to connect modular devices located in a healthcare facility to a cloud-based system (e.g., a cloud computing system 464 that may include a remote server 467 coupled to a remote storage 468). The modular communication hub 465 and the devices may be connected in a room in a healthcare facility specially equipped for surgical operations. In one aspect, the modular communication hub 465 may include a network hub 461 and/or a network switch 462 in communication with a network router 466. The modular communication hub 465 may be coupled to a local computer system 463 to provide local computer processing and data manipulation.

The computer system 463 may comprise a processor and a network interface. The processor may be coupled to a communication module, storage, memory, non-volatile memory, and input/output (I/O) interface via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (VISA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In an example, the processor may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

It is to be appreciated that the computer system 463 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 463 through input device(s) coupled to the I/O interface. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system 463 and to output information from the computer system 463 to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 463 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5, and the like. WAN technologies may include, but are not limited to, point-to-point links, circuit-switching networks like Integrated Services Digital Networks (ISDN) and variations thereon, packet-switching networks, and Digital Subscriber Lines (DSL).

In various examples, the computer system 463 may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system 463, it can also be external to the computer system 463. The hardware/software necessary for connection to the network interface may include, for illustrative purposes only, internal and external technologies such as modems, including regular telephone-grade modems, cable modems, optical fiber modems, and DSL modems, ISDN adapters, and Ethernet cards. In some examples, the network interface may also be provided using an RF interface.

Surgical data network associated with the surgical hub system 460 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 461 or network switch 462. An intelligent surgical data network may be referred to as a manageable hub or switch. A switching hub reads the destination address of each packet and then forwards the packet to the correct port.

Modular devices 1a-1n located in the operating theater may be coupled to the modular communication hub 465. The network hub 461 and/or the network switch 462 may be coupled to a network router 466 to connect the devices 1a-1n to the cloud computing system 464 or the local computer system 463. Data associated with the devices 1a-1n may be transferred to cloud-based computers via the router for remote data processing and manipulation. Data associated with the devices 1a-1n may also be transferred to the local computer system 463 for local data processing and manipulation. Modular devices 2a-2m located in the same operating theater also may be coupled to a network switch 462. The network switch 462 may be coupled to the network hub 461 and/or the network router 466 to connect the devices 2a-2m to the cloud 464. Data associated with the devices 2a-2m may be transferred to the cloud computing system 464 via the network router 466 for data processing and manipulation. Data associated with the devices 2a-2m may also be transferred to the local computer system 463 for local data processing and manipulation.

As illustrated in FIG. 4 a computing system, such as a surgical hub system 460, may include a modular communication hub 465 that is configured to connect modular devices (e.g., surgical devices) located in a healthcare facility to a cloud-based system (e.g., a cloud computing system 464 that may include a remote server 467 coupled to a remote storage 468). The modular communication hub 465 and the devices may be connected in a room in a healthcare facility specially equipped for surgical operations. In one aspect, the modular communication hub 465 may include a network hub 461 and/or a network switch 462 in communication with a network router 466. The modular communication hub 465 may be coupled to a local computer system (e.g., a computing device) to provide local computer processing and data manipulation.

Figure 5:
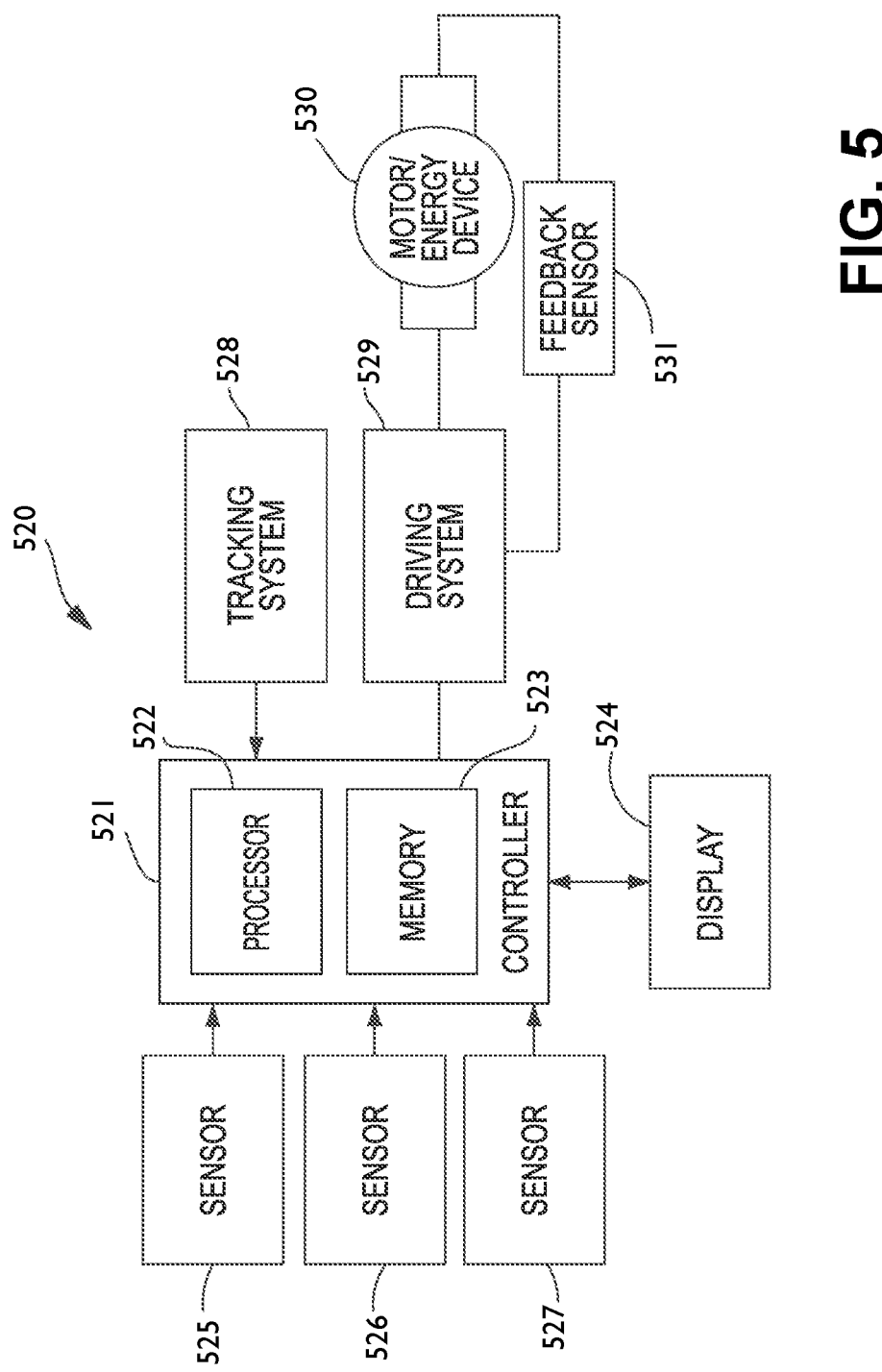
FIG. 5 illustrates a logic diagram of a control system of a surgical instrument.

FIG. 5 illustrates a logical diagram of a control system 520 of a surgical instrument or a surgical tool in accordance with one or more aspects of the present disclosure. The surgical instrument or the surgical tool may be configurable. The surgical instrument may include surgical fixtures specific to the procedure at-hand, such as imaging devices, surgical staplers, energy devices, endocutter devices, or the like. For example, the surgical instrument may include any of a powered stapler, a powered stapler generator, an energy device, an advanced energy device, an advanced energy jaw device, an endocutter clamp, an energy device generator, an in-operating-room imaging system, a smoke evacuator, a suction-irrigation device, an insufflation system, or the like. The system 520 may comprise a control circuit. The control circuit may include a microcontroller 521 comprising a processor 522 and a memory 523. One or more of sensors 525, 526, 527, for example, provide real-time feedback to the processor 522. A motor 530, driven by a motor driver 529, operably couples a longitudinally movable displacement member to drive the I-beam knife element. A tracking system 528 may be configured to determine the position of the longitudinally movable displacement member. The position information may be provided to the processor 522, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 524 may display a variety of operating conditions of the instruments and may include touch screen functionality for data input. Information displayed on the display 524 may be overlaid with images acquired via endoscopic imaging modules.

The microcontroller 521 may be any single-core or multicore processor such as those known under the trade name ARM Cortex by Texas Instruments. In one aspect, the main microcontroller 521 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

The microcontroller 521 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 521 may be programmed to perform various functions such as precise control over the speed and position of the knife and articulation systems. In one aspect, the microcontroller 521 may include a processor 522 and a memory 523. The electric motor 530 may be a brushed direct current (DC) motor with a gearbox and mechanical links to an articulation or knife system. In one aspect, a motor driver 529 may be an A3941 available from Allegro Microsystems, Inc. Other motor drivers may be readily substituted for use in the tracking system 528 comprising an absolute positioning system. A detailed description of an absolute positioning system is described in U.S. Patent Application Publication No. 2017/0296213, tided SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 521 may be programmed to provide precise control over the speed and position of displacement members and articulation systems. The microcontroller 521 may be configured to compute a response in the software of the microcontroller 521. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

The motor 530 may be controlled by the motor driver 529 and can be employed by the firing system of the surgical instrument or tool. In various forms, the motor 530 may be a brushed DC driving motor having a maximum rotational speed of approximately 25,000 RPM. In some examples, the motor 530 may include a brushless motor, a cordless motor, a synchronous motor, a stepper motor, or any other suitable electric motor. The motor driver 529 may comprise an H-bridge driver comprising field-effect transistors (FETs), for example. The motor 530 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 529 may be an A3941 available from Allegro Microsystems, Inc. A3941 may be a full-bridge controller for use with external N-channel power metal-oxide semiconductor field-effect transistors (VIOSFETs) specifically designed for inductive loads, such as brush DC motors. The driver 529 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the low-side FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 528 comprising an absolute positioning system.

The tracking system 528 may comprise a controlled motor drive circuit arrangement comprising a position sensor 525 according to one aspect of this disclosure. The position sensor 525 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 525 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photodiodes or photodetectors, or any combination thereof.

The electric motor 530 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 525 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 525 may be equivalent to a longitudinal linear displacement d1 of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 525 completing one or more revolutions for the full stroke of the displacement member. The position sensor 525 may complete multiple revolutions for the full stroke of the displacement member.

A series of switches, where n is an integer greater than one, may be employed alone or in combination with a gear reduction to provide a unique position signal for more than one revolution of the position sensor 525. The state of the switches may be fed back to the microcontroller 521 that applies logic to determine a unique position signal corresponding to the longitudinal linear displacement d1+ d2+ . . . dn of the displacement member. The output of the position sensor 525 is provided to the microcontroller 521. The position sensor 525 of the sensor arrangement may comprise a magnetic sensor, an analog rotary sensor like a potentiometer, or an array of analog Hall-effect elements, which output a unique combination of position signals or values.

The position sensor 525 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

The position sensor 525 for the tracking system 528 comprising an absolute positioning system may comprise a magnetic rotary absolute positioning system. The position sensor 525 may be implemented as an AS5055EQFT single-chip magnetic rotary position sensor available from Austria Microsystems, AG. The position sensor 525 is interfaced with the microcontroller 521 to provide an absolute positioning system. The position sensor 525 may be a low-voltage and low-power component and may include four Hall-effect elements in an area of the position sensor 525 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bit-shift, and table lookup operations. The angle position, alarm bits, and magnetic field information may be transmitted over a standard serial communication interface, such as a serial peripheral interface (SPI) interface, to the microcontroller 521. The position sensor 525 may provide 12 or 14 bits of resolution. The position sensor 525 may be an AS5055 chip provided in a small QFN 16-pin 4×4×0.85 mm package.

The tracking system 528 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 525. In some aspects, the other sensor(s) can include sensor arrangements such as those described in U.S. Pat. No. 9,345,481, tided STAPLE CARTRIDGE TISSUE THICKNESS SENSOR SYSTEM, which issued on May 24, 2016, which is herein incorporated by reference in its entirety; U.S. Patent Application Publication No. 2014/0263552, tided STAPLE CARTRIDGE TISSUE THICKNESS SENSOR SYSTEM, which published on Sep. 18, 2014, which is herein incorporated by reference in its entirety; and U.S. patent application Ser. No. 15/628,175, tided TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertia, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 530 has taken to infer the position of a device actuator, drive bar, knife, or the like.

A sensor 526, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 522. Alternatively, or in addition to the sensor 526, a sensor 527, such as, for example, a load sensor, can measure the closure force applied by the closure drive system to the anvil. The sensor 527, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 531 can be employed to measure the current drawn by the motor 530. The force required to advance the firing member can correspond to the current drawn by the motor 530, for example. The measured force may be converted to a digital signal and provided to the processor 522.

For example, the strain gauge sensor 526 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 526, such as, for example, a micro-strain gauge, that can be configured to measure one or more parameters of the end effector, for example. In one aspect, the strain gauge sensor 526 can measure the amplitude or magnitude of the strain exerted on a jaw member of an end effector during a clamping operation, which can be indicative of the tissue compression. The measured strain can be converted to a digital signal and provided to a processor 522 of the microcontroller 521. A load sensor 527 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 522.

The measurements of the tissue compression, the tissue thickness, and/or the force required to close the end effector on the tissue, as respectively measured by the sensors 526, 527, can be used by the microcontroller 521 to characterize the selected position of the firing member and/or the corresponding value of the speed of the firing member. In one instance, a memory 523 may store a technique, an equation, and/or a lookup table which can be employed by the microcontroller 521 in the assessment.

The control system 520 of the surgical instrument or tool also may comprise wired or wireless communication circuits to communicate with a surgical hub, such as surgical hub 460 for example, as shown in FIG. 4.

Figure 6:
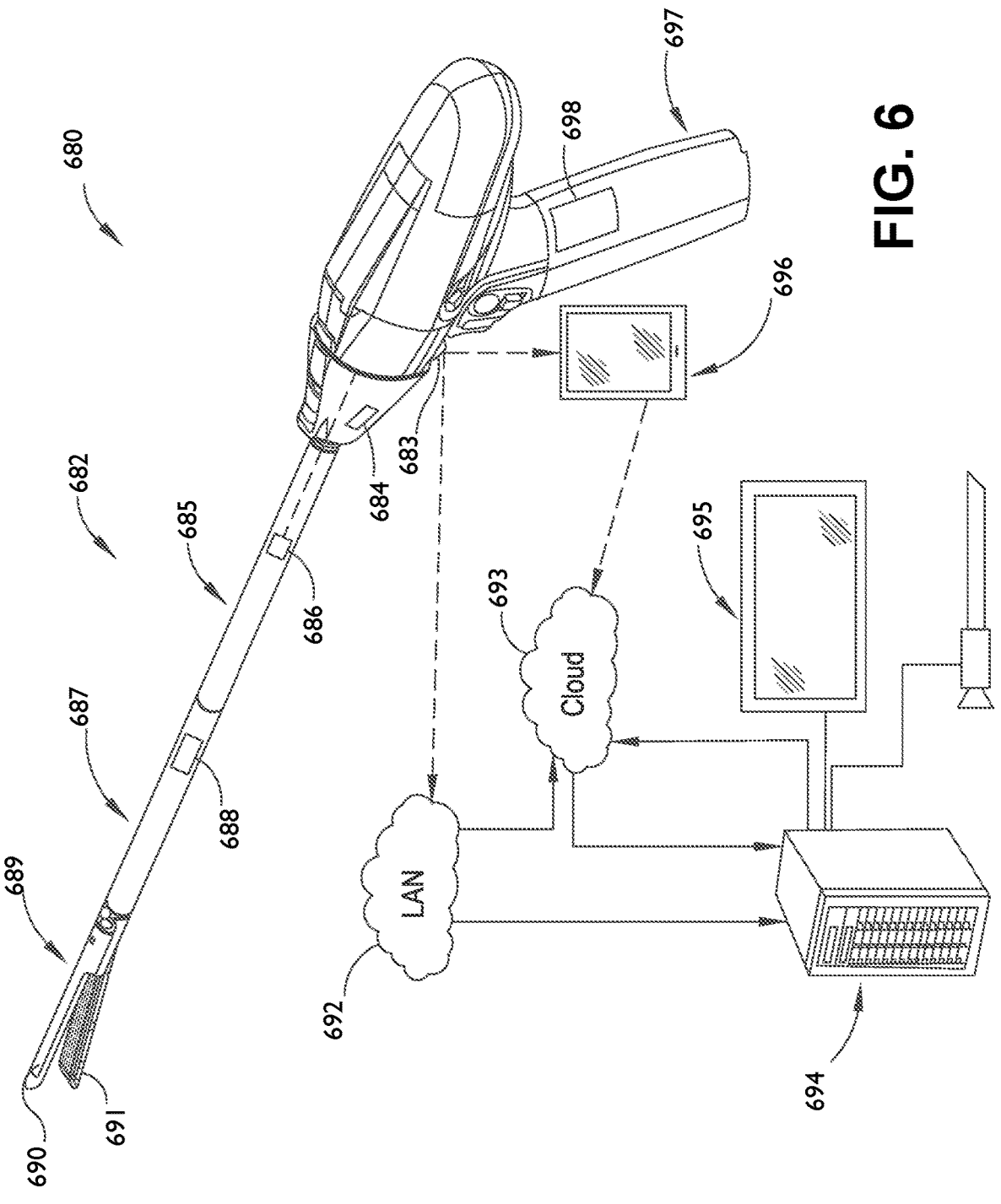
FIG. 6 shows an example surgical system that includes a handle having a controller and a motor, an adapter releasably coupled to the handle, and a loading unit releasably coupled to the adapter.

FIG. 6 illustrates an example surgical system 680 in accordance with the present disclosure and may include a surgical instrument 682 that can be in communication with a console 694 or a portable device 696 through a local area network 692 and/or a cloud network 693 via a wired and/or wireless connection. The console 694 and the portable device 696 may be any suitable computing device. The surgical instrument 682 may include a handle 697, an adapter 685, and a loading unit 687. The adapter 685 releasably couples to the handle 697 and the loading unit 687 releasably couples to the adapter 685 such that the adapter 685 transmits a force from a drive shaft to the loading unit 687. The adapter 685 or the loading unit 687 may include a force gauge (not explicitly shown) disposed therein to measure a force exerted on the loading unit 687. The loading unit 687 may include an end effector 689 having a first jaw 691 and a second jaw 690. The loading unit 687 may be an in-situ loaded or multi-firing loading unit (MFLU) that allows a clinician to fire a plurality of fasteners multiple times without requiring the loading unit 687 to be removed from a surgical site to reload the loading unit 687.

The first and second jaws 691, 690 may be configured to clamp tissue therebetween, fire fasteners through the clamped tissue, and sever the clamped tissue. The first jaw

691 may be configured to fire at least one fastener a plurality of times or may be configured to include a replaceable multi-fire fastener cartridge including a plurality of fasteners (e.g., staples, clips, etc.) that may be fired more than one time prior to being replaced. The second jaw 690 may include an anvil that deforms or otherwise secures the fasteners, as the fasteners are ejected from the multi-fire fastener cartridge.

The handle 697 may include a motor that is coupled to the drive shaft to affect rotation of the drive shaft. The handle 697 may include a control interface to selectively activate the motor. The control interface may include buttons, switches, levers, sliders, touchscreens, and any other suitable input mechanisms or user interfaces, which can be engaged by a clinician to activate the motor.

The control interface of the handle 697 may be in communication with a controller 698 of the handle 697 to selectively activate the motor to affect rotation of the drive shafts. The controller 698 may be disposed within the handle 697 and may be configured to receive input from the control interface and adapter data from the adapter 685 or loading unit data from the loading unit 687. The controller 698 may analyze the input from the control interface and the data received from the adapter 685 and/or loading unit 687 to selectively activate the motor. The handle 697 may also include a display that is viewable by a clinician during use of the handle 697. The display may be configured to display portions of the adapter or loading unit data before, during, or after firing of the instrument 682.

The adapter 685 may include an adapter identification device 684 disposed therein and the loading unit 687 may include a loading unit identification device 688 disposed therein. The adapter identification device 684 may be in communication with the controller 698, and the loading unit identification device 688 may be in communication with the controller 698. It will be appreciated that the loading unit identification device 688 may be in communication with the adapter identification device 684, which relays or passes communication from the loading unit identification device 688 to the controller 698.

The adapter 685 may also include a plurality of sensors 686 (one shown) disposed thereabout to detect various conditions of the adapter 685 or of the environment (e.g., if the adapter 685 is connected to a loading unit, if the adapter 685 is connected to a handle, if the drive shafts are rotating, the torque of the drive shafts, the strain of the drive shafts, the temperature within the adapter 685, a number of firings of the adapter 685, a peak force of the adapter 685 during firing, a total amount of force applied to the adapter 685, a peak retraction force of the adapter 685, a number of pauses of the adapter 685 during firing, etc.). The plurality of sensors 686 may provide an input to the adapter identification device 684 in the form of data signals. The data signals of the plurality of sensors 686 may be stored within or be used to update the adapter data stored within the adapter identification device 684. The data signals of the plurality of sensors 686 may be analog or digital. The plurality of sensors 686 may include a force gauge to measure a force exerted on the loading unit 687 during firing.

The handle 697 and the adapter 685 can be configured to interconnect the adapter identification device 684 and the loading unit identification device 688 with the controller 698 via an electrical interface. The electrical interface may be a direct electrical interface (i.e., include electrical contacts that engage one another to transmit energy and signals therebetween). Additionally, or alternatively, the electrical interface may be a non-contact electrical interface to wirelessly transmit energy and signals therebetween (e.g., inductively transfer). It is also contemplated that the adapter identification device 684 and the controller 698 may be in wireless communication with one another via a wireless connection separate from the electrical interface.

The handle 697 may include a transceiver 683 that is configured to transmit instrument data from the controller 698 to other components of the system 680 (e.g., the LAN 20292, the cloud 693, the console 694, or the portable device 696). The controller 698 may also transmit instrument data and/or measurement data associated with one or more sensors 686 to a surgical hub. The transceiver 683 may receive data (e.g., cartridge data, loading unit data, adapter data, or other notifications) from the surgical hub 670. The transceiver 683 may receive data (e.g., cartridge data, loading unit data, or adapter data) from the other components of the system 680. For example, the controller 698 may transmit instrument data including a serial number of an attached adapter (e.g., adapter 685) attached to the handle 697, a serial number of a loading unit (e.g., loading unit 687) attached to the adapter 685, and a serial number of a multi-fire fastener cartridge loaded into the loading unit to the console 694. Thereafter, the console 694 may transmit data (e.g., cartridge data, loading unit data, or adapter data) associated with the attached cartridge, loading unit, and adapter, respectively, back to the controller 698. The controller 698 can display messages on the local instrument display or transmit the message, via transceiver 683, to the console 694 or the portable device 696 to display the message on the display 695 or portable device screen, respectively.

Figure 7A:
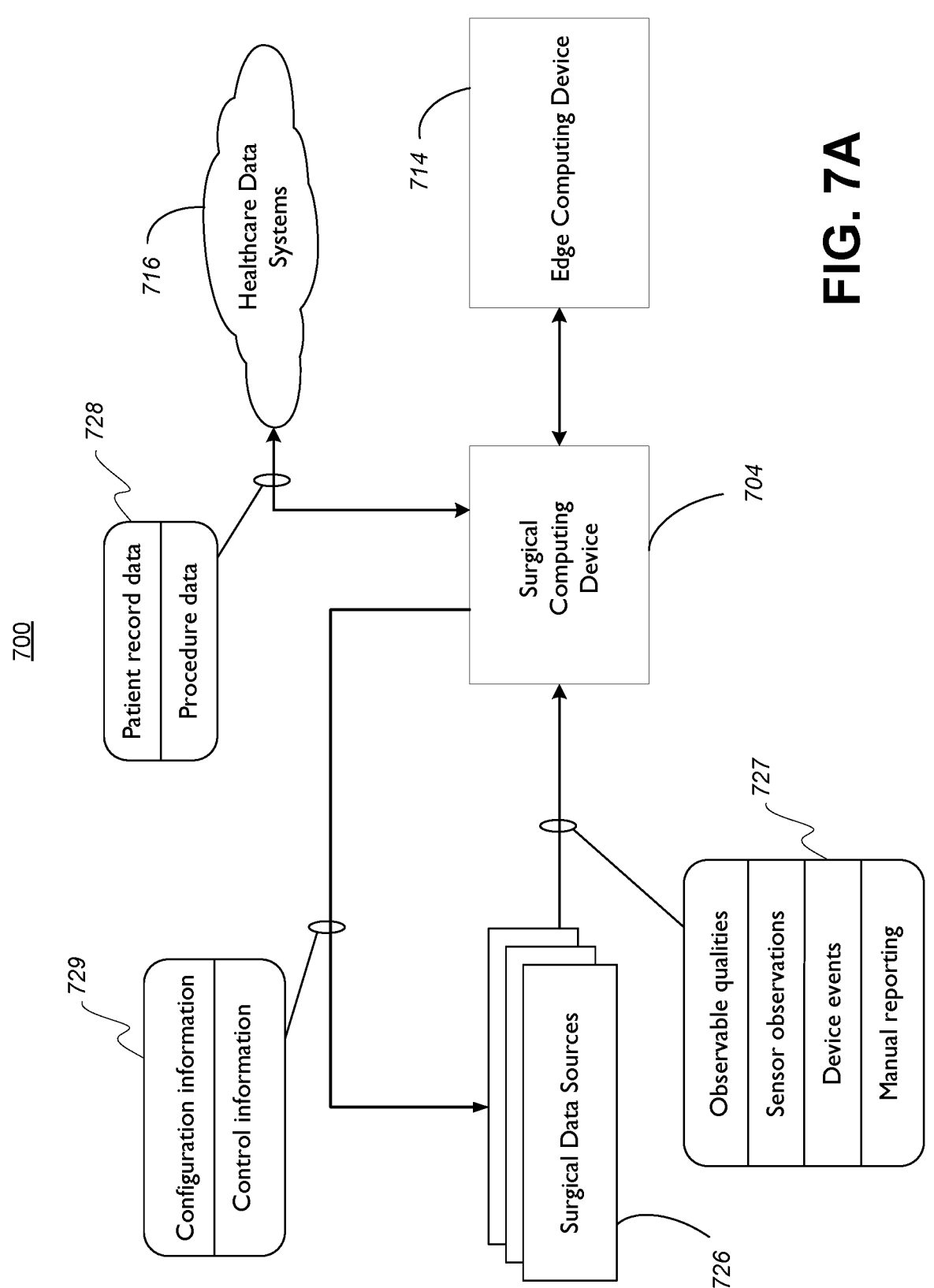
FIG. 7A-D show an example surgical system information matrix, an example information flow in a surgical system, an example information flow in a surgical system with a surgical robot, and an illustration of surgical information in the context of a procedure, respectively.

FIG. 7A illustrates a surgical system 700 that may include a matrix of surgical information. This surgical information may include any discrete atom of information relevant to surgical operation. Generally described, such surgical information may include information related to the context and scope of the surgery itself (e.g., healthcare information 728). Such information may include data such as procedure data and patient record data, for example. Procedure data and/or patient record data may be associated with a related healthcare data system 716 in communication with the surgical computing device 704.

The procedure data may include information related to the instruments and/or replaceable instrument components to be employed in a given procedure, such as a master list for example. The surgical computing device 704 may record (e.g., capture barcode scans) of the instruments and/or replaceable instrument components being put to use in the procedure. Such surgical information may be used to algorithmically confirm that appropriate configurations of surgical instruments and/or replaceable components are being used. See U.S. Patent Application Publication No. US 2020-0405296 A1 (U.S. patent application Ser. No. 16/458,103), tided PACKAGING FOR A REPLACEABLE COMPONENT OF A SURGICAL STAPLING SYSTEM, filed Jun. 30, 2019, the contents of which is hereby incorporated by reference herein in its entirety.

For example, patient record data may be suitable for use in changing the configurations of certain surgical devices. For example, patient data may be used to understand and improve surgical device algorithmic behavior. In an example, surgical staplers may adjust operational parameters related to compression, speed of operation, location of use, feedback based on information (e.g., information indicative of a specific patient's tissue and/or tissue characteristics) in the patient record. See U.S. Patent Application Publication No. US 2019-0200981 A1 (U.S. patent application Ser. No. 16/209,423), titled METHOD OF COMPRESSING TISSUE WITHIN A STAPLING DEVICE AND SIMULTANEOUSLY DISPLAYING THE LOCATION OF THE TISSUE WITHIN THE JAWS, filed Dec. 4, 2018, the contents of which is hereby incorporated by reference herein in its entirety The surgical information may include information related to the configuration and/or control of devices being used in the surgery (e.g., device operational information 729). Such device operational information 729 may include information about the initial settings of surgical devices. Device operational information 729 may include information about changes to the settings of surgical devices. Device operational information 729 may include information about controls sent to the devices from the surgical computing device 704 and information flows related to such controls.

The surgical information may include information generated during the surgery itself (e.g., surgery information 727). Such surgery information 727 may be include any information generated by a surgical data source 726. The data sources 726 may include any device in a surgical context that may generate useful surgery information 727. This surgery information 727 may present itself as observable qualities of the data source 726. The observable qualities may include static qualities, such as a device's model number, serial number, and the like. The observable qualities may include dynamic qualities such as the state of configurable settings of the device. The surgery information 727 may present itself as the result of sensor observations for example. Sensor observations may include those from specific sensors within the surgical theatre, sensors for monitoring conditions, such as patient condition, sensors embedded in surgical devices, and the like. The sensor observations may include information used during the surgery, such as video, audio, and the like. The surgery information 727 may present itself as a device event data. Surgical devices may generate notifications and/or may log events, and such events may be included in surgery information 727 for communication to the surgical computing device 704. The surgery information 727 may present itself as the result of manual recording, for example. A healthcare professional may make a record during the surgery, such as asking that a note be taken, capturing a still image from a display, and the like The surgical data sources 726 may include modular devices (e.g., which can include sensors configured to detect parameters associated with the patient, HCPs and environment and/or the modular device itself), local databases (e.g., a local EMR database containing patient records), patient monitoring devices (e.g., a blood pressure (BP) monitor and an electrocardiography (EKG) monitor), HCP monitoring devices, environment monitoring devices, surgical instruments, surgical support equipment, and the like.

Intelligent surgical instruments may sense and measure certain operational parameters in the course of their operation. For example, intelligent surgical instruments, such as surgical robots, digital laparoscopic devices, and the like, may use such measurements to improve operation, for example to limit over compression, to reduce collateral damage, to minimize tissue tension, to optimize usage location, and the like. See U.S. Patent Application Publication No. US 2018-0049822 A1 (U.S. patent application Ser. No. 15/237,753), titled CONTROL OF ADVANCEMENT RATE AND APPLICATION FORCE BASED ON MEASURED FORCES, filed Aug. 16, 2016, the contents of which is hereby incorporated by reference herein in its entirety. Such surgical information may be communicated to the surgical computing device 704.

The surgical computing device 704 can be configured to derive the contextual information pertaining to the surgical procedure from the data based upon, for example, the particular combination(s) of received data or the particular order in which the data is received from the data sources 726. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical computing device 704 to derive or infer information related to the surgical procedure from received data can be referred to as "situational awareness." For example, the surgical computing device 704 can incorporate a situational awareness system, which is the hardware and/or programming associated with the surgical computing device 704 that derives contextual information pertaining to the surgical procedure from the received data and/or a surgical plan information received from the edge computing system 714 or a healthcare data system 716 (e.g., enterprise cloud server). Such situational awareness capabilities may be used to generation surgical information (such as control and/or configuration information) based on a sensed situation and/or usage. See U.S. Patent Application Publication No. US 2019-0104919 A1 (U.S. patent application Ser. No. 16/209,478), tided METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, filed Dec. 4, 2018, the contents of which is hereby incorporated by reference herein in its entirety.

In operation, this matrix of surgical information may be present as one or more information flows. For example, surgical information may flow from the surgical data sources 726 to the surgical computing device 704. Surgical information may flow from the surgical computing device 704 to the surgical data sources 726 (e.g., surgical devices). Surgical information may flow between the surgical computing device 704 and one or more healthcare data systems 716. Surgical information may flow between the surgical computing device 704 and one or more edge computing devices 714. Aspects of the information flows, including, for example, information flow endpoints, information storage, data interpretation, and the like, may be managed relative to the surgical system 700 (e.g., relative to the healthcare facility) See U.S. Patent Application Publication No. US 2019-0206564 A1 (U.S. patent application Ser. No. 16/209,490), tided METHOD FOR FACILITY DATA COLLECTION AND INTERPRETATION, filed Dec. 4, 2018, the contents of which is hereby incorporated by reference herein in its entirety.

Surgical information, as presented in its one or more information flows, may be used in connection with one or more artificial intelligence (AI) systems to further enhance the operation of the surgical system 700. For example, a machine learning system, such as that described herein, may operate on one or more information flows to further enhance the operation of the surgical system 700.

Figure 7B:
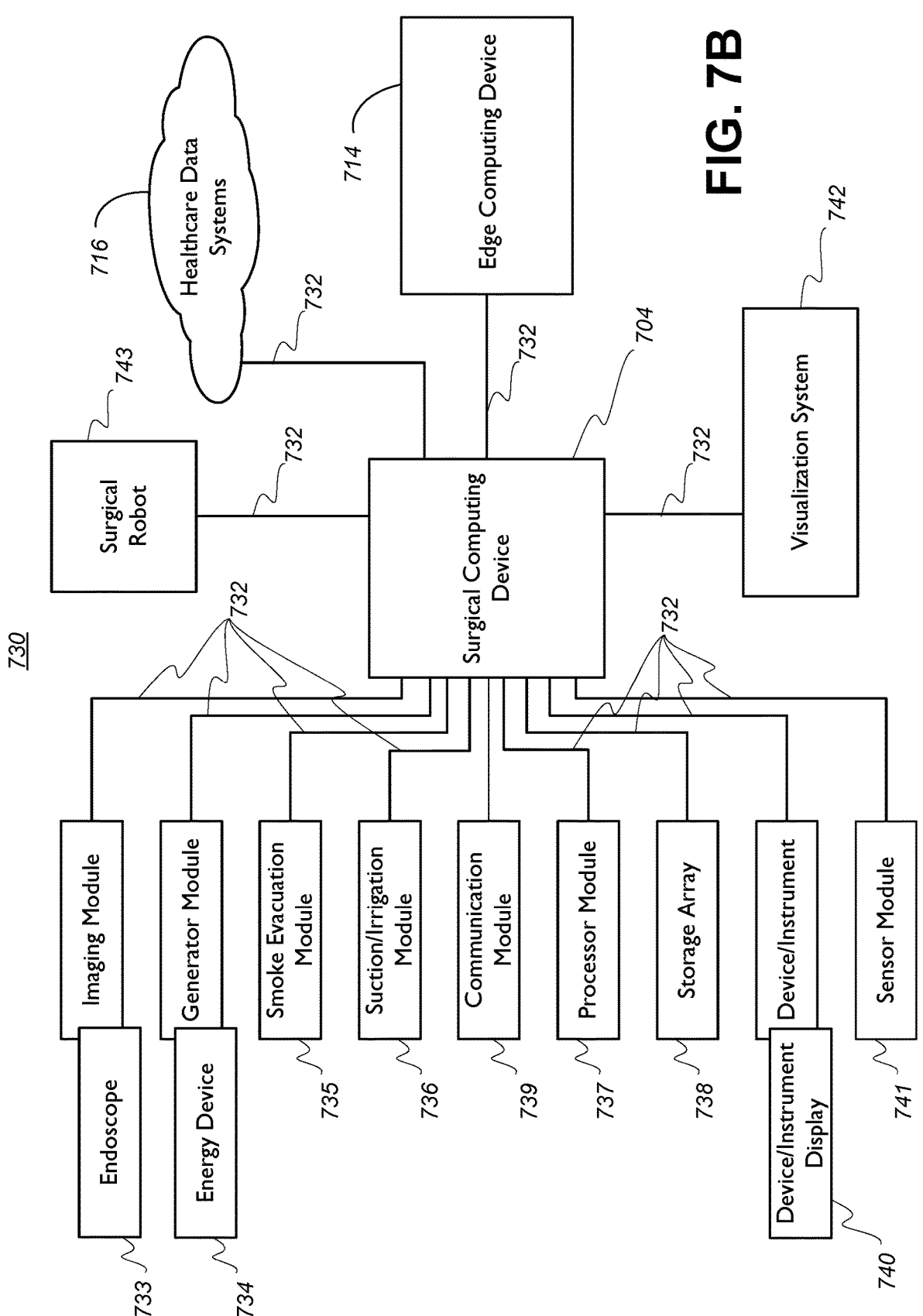

FIG. 7B shows an example computer-implement surgical system 730 with a plurality of information flows 732. A surgical computing device 704 may communication with and/or incorporate one or more surgical data sources. For example, an imaging module 733 (and endoscope) may exchange surgical information with the surgical computing device 704. Such information may include information from the imaging module 733 (and endoscope), such as video information, current settings, system status information, and the like. The imaging module 733 may receive information from the surgical computing device 704, such as control information, configuration information, operational updates (such as software/firmware), and the like.

For example, a generator module 734 (and corresponding energy device) may exchange surgical information with the surgical computing device 704. Such information may include information from the generator module 734 (and corresponding energy device), such as electrical information (e.g., current, voltage, impedance, frequency, wattage), activity state information, sensor information such as temperature, current settings, system events, active time duration, and activation timestamp, and the like. The generator module 734 may receive information from the surgical computing device 704, such as control information, configuration information, changes to the nature of the visible and audible notifications to the healthcare professional (e.g., changing the pitch, duration, and melody of audible tones), electrical application profiles and/or application logic that may instruct the generator module to provide energy with a defined characteristic curve over the application time, operational updates (such as software/firmware), and the like.

For example, a smoke evacuator 735 may exchange surgical information with the surgical computing device 704. Such information may include information from the smoke evacuator 735, such as operational information (e.g., revolutions per minute), activity state information, sensor information such as air temperature, current settings, system events, active time duration, and activation timestamp, and the like. The smoke evacuator 735 may receive information from the surgical computing device 704, such as control information, configuration information, operational updates (such as software/firmware), and the like.

For example, a suction/irrigation module 736 may exchange surgical information with the surgical computing device 704. Such information may include information from the suction/irrigation module 736, such as operational information (e.g., liters per minute), activity state information, internal sensor information, current settings, system events, active time duration, and activation timestamp, and the like. The suction/irrigation module 736 may receive information from the surgical computing device 704, such as control information, configuration information, operational updates (such as software/firmware), and the like.

For example, a communication module 739, a processor module 737, and/or a storage array 738 may exchange surgical information with the surgical computing device 704. In an example, the communication module 739, the processor module 737, and/or the storage array 738 may constitute all or part of the computing platform upon which the surgical computing device 704 runs. In an example, the communication module 739, the processor module 737, and/or the storage array 738 may provide local computing resources to other devices in the surgical system 730. Information from the communication module 739, the processor module 737, and/or the storage array 738 to the surgical computing device 704 may include logical computing-related reports, such as processing load, processing capacity, process identification, CPU %, CPU time, threads, GPU %, GPU time, memory utilization, memory thread, memory ports, energy usage, bandwidth related information, packets in, packets out, data rate, channel utilization, buffer status, packet loss information, system events, other state information, and the like. The communication module 739, the processor module 737, and/or the storage array 738 may receive information from the surgical computing device 704, such as control information, configuration information, operational updates (such as software/firmware), and the like. The communication module 739, the processor module 737, and/or the storage array 738 may also receive information from the surgical computing device 704 generated by another element or device of the surgical system 730. For example, data source information may be sent to and stored in the storage array. For example, data source information may be processed by the processor module 737.

For example, an intelligent instrument 740 (with or without a corresponding display) may exchange surgical information with the surgical computing device 704. Such information may include information from the intelligent instrument 740 relative to the instrument's operation, such as device electrical and/or mechanical information (e.g., current, voltage, impedance, frequency, wattage, torque, force, pressure, etc.), load state information (e.g., information regarding the identity, type, and/or status of reusables, such as staple cartridges), internal sensor information such as clamping force, tissue compression pressure and/or time, system events, active time duration, and activation timestamp, and the like. The intelligent instrument 740 may receive information from the surgical computing device 704, such as control information, configuration information, changes to the nature of the visible and audible notifications to the healthcare professional (e.g., changing the pitch, duration, and melody of audible tones), mechanical application profiles and/or application logic that may instruct a mechanical component of the instrument to operate with a defined characteristic (e.g., blade/anvil advance speed, mechanical advantage, firing time, etc.), operational updates (such as software/firmware), and the like.

For example, in a surgical stapling and cutting instrument, control and configuration information may be used to modify operational parameters, such as motor velocity for example. Data collections of surgical information may be used to define the power, force, and/or other functional operation and/or behavior of an intelligent surgical stapling and cutting instrument. See U.S. Pat. No. 10,881,399 B2 (U.S. patent application Ser. No. 15/628,175), tided TECHNIQUES FOR ADAPTIVE CONTROL OF MOTOR VELOCITY OF A SURGICAL STAPLING AND CUTTING INSTRUMENT, filed Jun. 20, 2017, the contents of which is hereby incorporated by reference herein in its entirety.

For example, in energy devices, control and configuration information (e.g., control and configuration information based on a situational awareness of the surgical computing device 704) may be used to adapt the function and/or behavior for improved results. See U.S. Patent Application Publication No. US 2019-0201047 A1 (U.S. patent application Ser. No. 16/209,458), tided METHOD FOR SMART ENERGY DEVICE INFRASTRUCTURE, filed Dec. 4, 2018, the contents of which is hereby incorporated by reference herein in its entirety. Likewise, in combo energy devices (e.g., devices which may use more than one energy modality) such control and/or configuration information may be used to select an appropriate operational mode. For example, the surgical computing device 704 may use surgical information including information being received from patient monitoring to send control and/or configuration information to the combo energy device. See U.S. Patent Application Publication No. US 2017-0202605 A1 (U.S. patent application Ser. No. 15/382,515), titled MODULAR BATTERY POWERED HANDHELD SURGICAL INSTRUMENT AND METHODS THEREFOR, filed Dec. 16, 2016, the contents of which is hereby incorporated by reference herein in its entirety.

For example, a sensor module 741 may exchange surgical information with the surgical computing device 704. Such information may include information from the sensor module 741 relative to its sensor function, such as sensor results themselves, observational frequency and/or resolution, observational type, device alerts such as alerts for sensor failure, observations exceeding a defined range, observations exceeding an observable range, and the like. The sensor module 741 may receive information from the surgical computing device 704, such as control information, configuration information, changes to the nature of observation (e.g., frequency, resolution, observational type etc.), triggers that define specific events for observation, on control, off control, data buffering, data preprocessing algorithms, operational updates (such as software/firmware), and the like.

For example, a visualization system 742 may exchange surgical information with the surgical computing device 704. Such information may include information from the visualization system 742, such visualization data itself (e.g., still image, video, advanced spectrum visualization, etc.), visualization metadata (e.g., visualization type, resolution, frame rate, encoding, bandwidth, etc.). The visualization system 742 may receive information from the surgical computing device 704, such as control information, configuration information, changes to the video settings (e.g., visualization type, resolution, frame rate, encoding, etc.), visual display overlay data, data buffering size, data preprocessing algorithms, operational updates (such as software/firmware), and the like.

Surgical information may be exchanged and/or used with advanced imaging systems. For example, surgical information may be exchanged and/or used to provide context for imaging data streams. For example, surgical information may be exchanged and/or used to expand the conditional understanding of such imaging data streams. See U.S. patent application Ser. No. 17/493,904, titled SURGICAL METHODS USING MULTI-SOURCE IMAGING, filed Oct. 5, 2021, the contents of which is hereby incorporated by reference herein in its entirety. See U.S. patent application Ser. No. 17/493,913, tided SURGICAL METHODS USING FIDUCIAL IDENTIFICATION AND TRACKING, filed Oct. 5, 2021, the contents of which is hereby incorporated by reference herein in its entirety.

For example, a surgical robot 743 may exchange surgical information with the surgical computing device 704. In an example, surgical information may include information related to the cooperative registration and interaction of surgical robotic systems. See U.S. patent application Ser. No. 17/449,765, tided COOPERATIVE ACCESS HYBRID PROCEDURES, filed Oct. 1, 2021, the contents of which is hereby incorporated by reference herein in its entirety. Information from the surgical robot 743 may include any aforementioned information as applied to robotic instruments, sensors, and devices. Information from the surgical robot 743 may also include information related to the robotic operation or control of such instruments, such as electrical/mechanical feedback of robot articulators, system events, system settings, mechanical resolution, control operation log, articulator path information, and the like. The surgical robot 743 may receive information from the surgical computing device 704, such as control information, configuration information, operational updates (such as software/firmware), and the like.

Surgical devices in communication with the surgical computing device 704 may exchange surgical information to aid in cooperative operation among the devices. For example, with the surgical robot 743 and the energy generator 734 may exchange surgical information with each other and/or the surgical computing device 704 for cooperative operation. Cooperative operation between the cooperatively the surgical robot 743 and the energy generator 734 may be used to minimize unwanted side effects like tissue sticking for example. Cooperative operation between the cooperatively the surgical robot 743 and the energy generator 734 may be used to improve tissue welding. See U.S. Patent Application Publication No. US 2019-0059929 A1 (U.S. patent application Ser. No. 15/689,072), titled METHODS, SYSTEMS, AND DEVICES FOR CONTROLLING ELECTROSURGICAL TOOLS, filed Aug. 29, 2017, the contents of which is hereby incorporated by reference herein in its entirety. Surgical information may be generated by the cooperating devices and/or the surgical computing device 704 in connection with their cooperative operation.

The surgical computing system 704 may be record, analyze, and/or act on surgical information flows, like those disclosed above for example. The surgical computing system 704 may aggregate such data for analysis. For example, the surgical computing system 704 may perform operations such as defining device relationships, establishing device cooperative behavior, monitoring and/or storing procedure details, and the like. Surgical information related to such operations may be further analyzed to refine algorithms, identify trends, and/or adapt surgical procedures. For example, surgical information may be further analyzed in comparison with patient outcomes as a function of such operations. See U.S. Patent Application Publication No. US 2019-0206562 A1 (U.S. patent application Ser. No. 16/209,416), tided METHOD OF HUB COMMUNICATION, PROCESSING, DISPLAY, AND CLOUD ANALYTICS, filed Dec. 4, 2018, the contents of which is hereby incorporated by reference herein in its entirety.

Figure 7C:
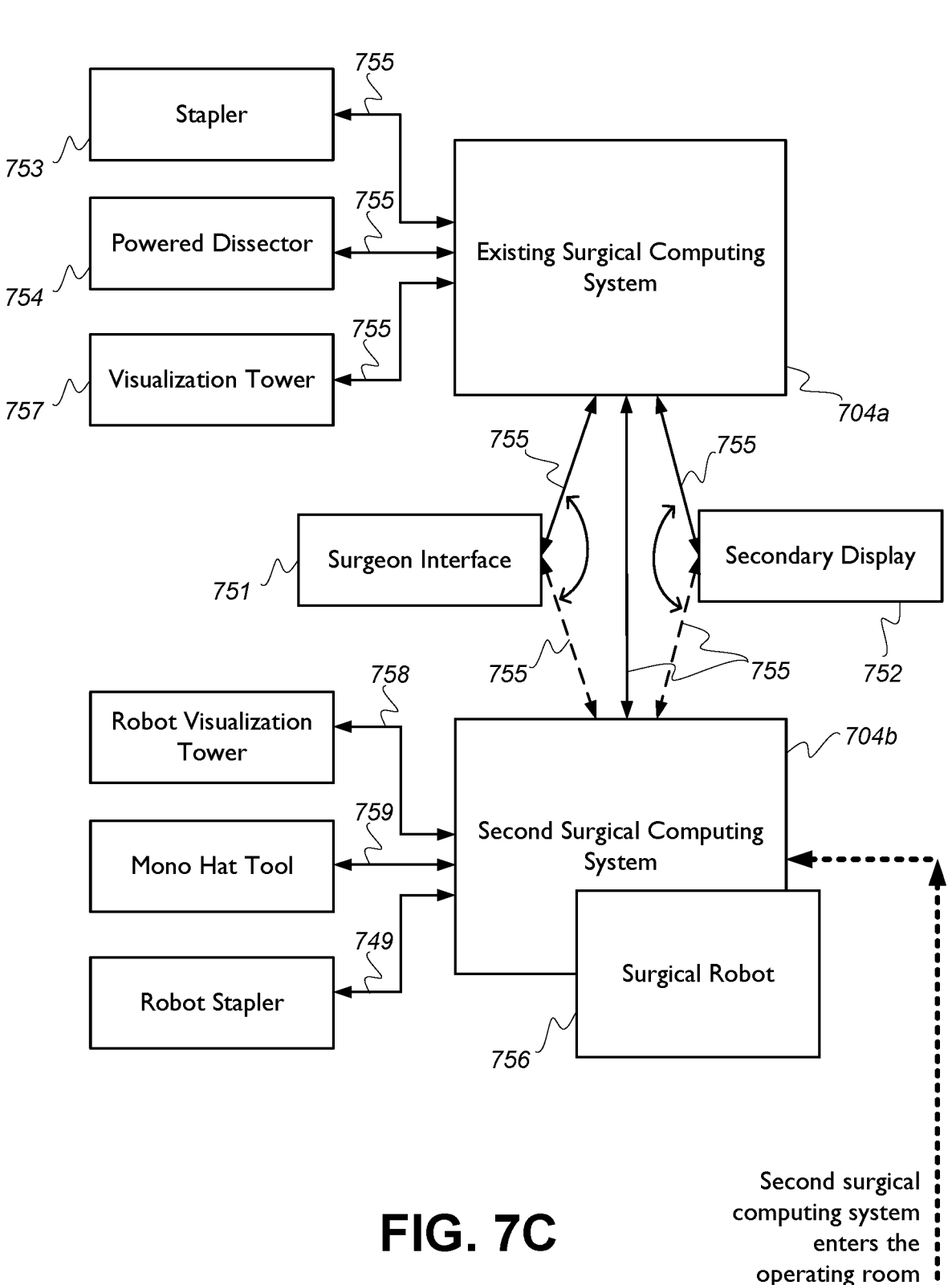

FIG. 7C illustrates an example information flow associated with a plurality of surgical computing systems 704a, 704b in a common environment. When the overall configuration of a computer-implement surgical system (e.g., computer-implement surgical system 750) changes (e.g., when data sources are added and/or removed from the surgical computing system, for example), further surgical information may be generated to reflect the changes. In this example, a second surgical computing system 704b (e.g., surgical hub) may be added (with a corresponding surgical robot) to surgical system 750 with an existing surgical computing system 704a. The messaging flow described here represents further surgical information flows 755 to be employed as disclosed herein (e.g., further consolidated, analyzed, and/or processed according to an algorithm, such as a machine learning algorithm).

Here, the two surgical computing systems 704a, 704b request permission from a surgical operator for the second surgical computing system 704b (with the corresponding surgical robot 756) to take control of the operating room from the existing surgical computing system 704a. The second surgical computing system 704b presents in the operating theater with control of the corresponding surgical robot 756, a robot visualization tower 758, a mono hat tool 759, and a robot stapler 749. The permission can be requested through a surgeon interface or console 751. Once permission is granted, the second surgical computing system 704b messages the existing surgical computing system 704a a request a transfer of control of the operating room.

In an example, the surgical computing systems 704*a*, 704*b* can negotiate the nature of their interaction without external input based on previously gathered data. For example, the surgical computing systems 704*a*, 704*b* may collectively determine that the next surgical task requires use of a robotic system. Such determination may cause the existing surgical computing system 704*a* to autonomously surrender control of the operating room to the second surgical computing system 704*b*. Upon completion of the surgical task, the second surgical computing system 704*b* may then autonomously return the control of the operating room to the existing surgical computing system 704*a*.

As illustrated in FIG. 7C, the existing surgical computing system 704*a* has transferred control to the second surgical computing system 704*b*, which has also taken control of the surgeon interface 751 and the secondary display 752. The second surgical computing system 704*b* assigns new identification numbers to the newly transferred devices. The existing surgical computing system 704*a* retains control the handheld stapler 753, the handheld powered dissector 754, and visualization tower 757. In addition, the existing surgical computing system 704*a* may perform a supporting role, wherein the processing and storage capabilities of the existing surgical computing system 704*a* are now available to the second surgical computing system 704*b*.

Figure 7D:
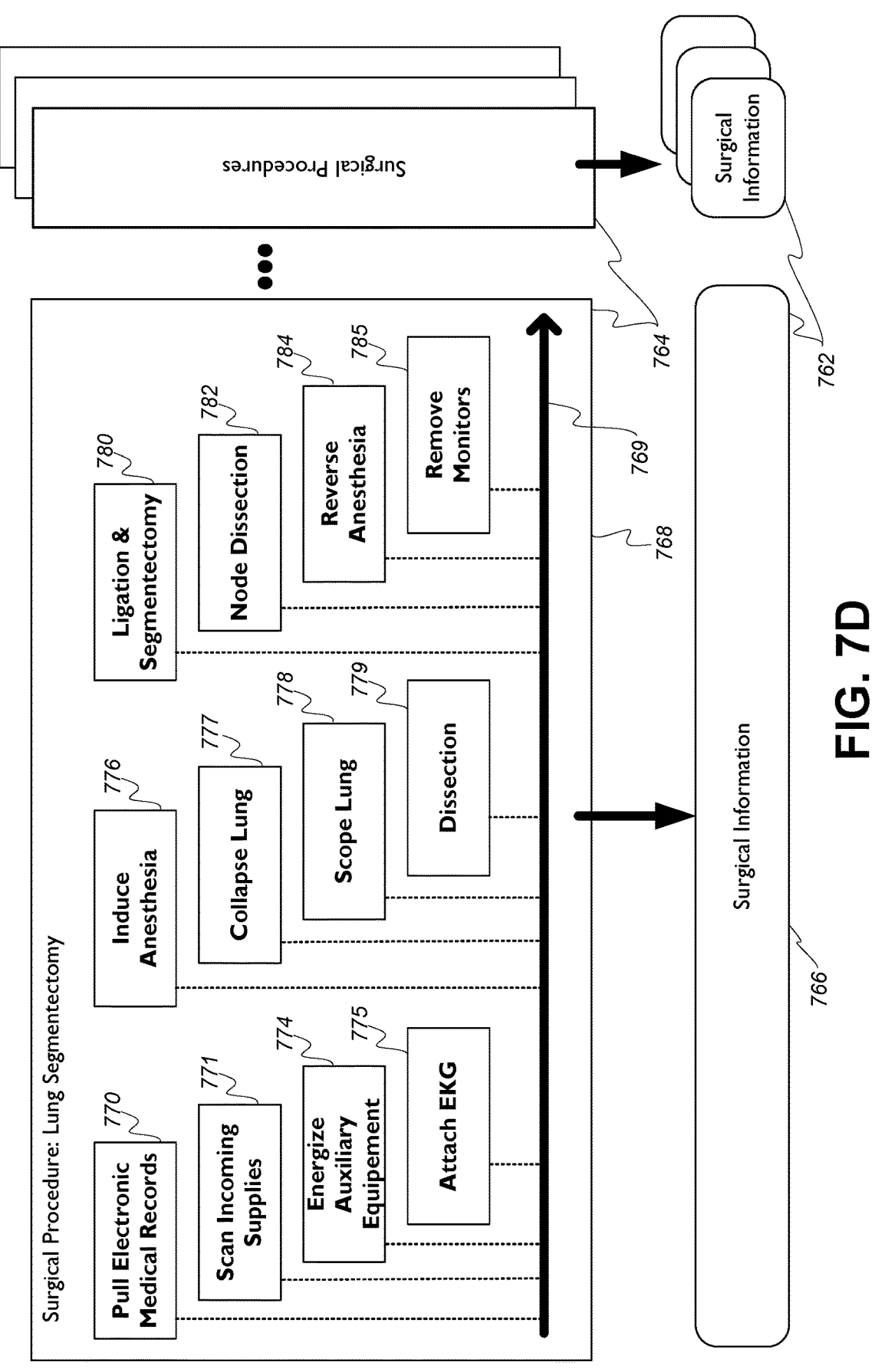

FIG. 7D illustrates an example surgical information flow in the context of a surgical procedure and a corresponding example use of the surgical information for predictive modeling. The surgical information disclosed herein may provide data regarding one or more surgical procedures, including the surgical tasks, instruments, instrument settings, operational information, procedural variations, and corresponding desirable metrics, such as improved patient outcomes, lower cost (e.g., fewer resources utilized, less surgical time, etc.). The surgical information disclosed herein (e.g., that disclosed in regard to FIGS. 7A-C) in the context of one or more surgical systems and devices disclosed herein, provides a platform upon which the specific machine learning algorithms and techniques disclosed herein may be used.

Surgical information 762 from a plurality of surgical procedures 764 (e.g., a subset of surgical information from each procedure) may be collected. The surgical information 762 may be collected from the plurality of surgical procedures 764 by collecting data represented by the one or more information flows disclosed herein, for example.

To illustrate, example instance of surgical information 766 may be generated from the example procedure 768 (e.g, a lung segmentectomy procedure as shown on a timeline 769). Surgical information 766 may be generated during the preoperative planning and may include patient record information. Surgical information 766 may be generated from the data sources (e.g., data sources 726) during the course of the surgical procedure, including data generated each time medical personnel utilize a modular device that is paired with the surgical computing system (e.g., surgical computing system 704). The surgical computing system may receive this data from the paired modular devices and other data sources The surgical computing system itself may generate surgical information as part of its operation during the procedure. For example, the surgical computing system may record information relating to configuration and control operations. The surgical computing system may record information related to situational awareness activities. For example, the surgical computing system may record the recommendations, prompts, and/or other information provided to the healthcare team (e.g., provided via a display screen) that may be pertinent for the next procedural step. For example, the surgical computing system may record configuration and control changes (e.g., the adjusting of modular devices based on the context). Such configuration and control changes may include activating monitors, adjusting the field of view (FOV) of a medical imaging device, changing the energy level of an ultrasonic surgical instrument or RF electrosurgical instrument, or the like.

At 770, the hospital staff members retrieve the patient's EMR from the hospital's EMR database. Based on select patient data in the EMR, the surgical computing system determines that the procedure to be performed is a thoracic procedure.

At 771, the staff members scan the incoming medical supplies for the procedure. The surgical computing system may cross-reference the scanned supplies with a list of supplies that are utilized in various types of procedures. The surgical computing system may confirm that the mix of supplies corresponds to a thoracic procedure. Further, the surgical computing system may determine that the procedure is not a wedge procedure (because the incoming supplies either lack certain supplies that are necessary for a thoracic wedge procedure or do not otherwise correspond to a thoracic wedge procedure). The medical personnel may also scan the patient band via a scanner that is communicably connected to the surgical computing system. The surgical computing system may confirm the patient's identity based on the scanned data.

At 774, the medical staff turns on the auxiliary equipment. The auxiliary equipment being utilized can vary according to the type of surgical procedure and the techniques to be used by the surgeon. In this example, the auxiliary equipment may include a smoke evacuator, an insufflator, and medical imaging device. When activated, the auxiliary equipment may pair with the surgical computing system. The surgical computing system may derive contextual information about the surgical procedure based on the types of paired. In this example, the surgical computing system determines that the surgical procedure is a VATS procedure based on this particular combination of paired devices. The contextual information about the surgical procedure may be confirmed by the surgical computing system via information from the patient's EMR.

The surgical computing system may retrieve the steps of the procedure to be performed. For example, the steps may be associated with a procedural plan (e.g., a procedural plan specific to this patient's surgery, a procedural plan associated with a particular surgeon, a procedural plan template for the procedure generally, or the like).

At 775, the staff members attach the EKG electrodes and other patient monitoring devices to the patient. The EKG electrodes and other patient monitoring devices pair with the surgical computing system. The surgical computing system may receive data from the patient monitoring devices.

At 776, the medical personnel induce anesthesia in the patient. The surgical computing system may record information related to this procedural step such as data from the modular devices and/or patient monitoring devices, including EKG data, blood pressure data, ventilator data, or combinations thereof, for example.

At 777, the patient's lung subject to operation is collapsed (ventilation may be switched to the contralateral lung). The surgical computing system may determine that this procedural step has commenced and may collect surgical information accordingly, including for example, ventilator data, one or more timestamps, and the like At 778, the medical imaging device (e.g., a scope) is inserted and video from the medical imaging device is initiated. The surgical computing system may receive the medical imaging device data (i.e., video or image data) through its connection to the medical imaging device. The data from the medical imaging device may include imaging data and/or imaging metadata, such as the angle at which the medical imaging device is oriented with respect to the visualization of the patient's anatomy, the number or medical imaging devices presently active, and the like. The surgical computing system may record positioning information of the medical imaging device. For example, one technique for performing a VATS lobectomy places the camera in the lower anterior corner of the patient's chest cavity above the diaphragm. Another technique for performing a VATS segmentectomy places the camera in an anterior intercostal position relative to the segmental fissure.

Using pattern recognition or machine learning techniques, for example, the surgical computing system may be trained to recognize the positioning of the medical imaging device according to the visualization of the patient's anatomy. For example, one technique for performing a VATS lobectomy utilizes a single medical imaging device. Another technique for performing a VATS segmentectomy uses multiple cameras. Yet another technique for performing a VATS segmentectomy uses an infrared light source (which may be communicably coupled to the surgical computing system as part of the visualization system).

At 779, the surgical team begins the dissection step of the procedure. The surgical computing system may collect data from the RF or ultrasonic generator indicating that an energy instrument is being fired. The surgical computing system may cross-reference the received data with the retrieved steps of the surgical procedure to determine that an energy instrument being fired at this point in the process (i.e., after the completion of the previously discussed steps of the procedure) corresponds to the dissection step. In an example, the energy instrument may be an energy tool mounted to a robotic arm of a robotic surgical system.

At 780, the surgical team proceeds to the ligation step of the procedure. The surgical computing system may collect surgical information 766 with regard to the surgeon ligating arteries and veins based on receiving data from the surgical stapling and cutting instrument indicating that such instrument is being fired. Next, the segmentectomy portion of the procedure is performed. The surgical computing system may collect information relating to the surgeon transecting the parenchyma. For example, the surgical computing system may receive surgical information 766 from the surgical stapling and cutting instrument, including data regarding its cartridge, settings, firing details, and the like.

At 782, the node dissection step is then performed. The surgical computing system may collect surgical information 766 with regard to the surgical team dissecting the node and performing a leak test. For example, the surgical computing system may collect data received from the generator indicating that an RF or ultrasonic instrument is being fired and including the electrical and status information associated with the firing. Surgeons regularly switch back and forth between surgical stapling/cutting instruments and surgical energy (i.e., RF or ultrasonic) instruments depending upon the particular step in the procedure. The surgical computing system may collect surgical information 766 in view of the particular sequence in which the stapling/cutting instruments and surgical energy instruments are used. In an example, robotic tools may be used for one or more steps in a surgical procedure. The surgeon may alternate between robotic tools and handheld surgical instruments and/or can use the devices concurrently, for example.

Next, the incisions are closed up and the post-operative portion of the procedure begins. At 784, the patient's anesthesia is reversed. The surgical computing system may collect surgical information regarding the patient emerging from the anesthesia based on ventilator data (e.g., the patient's breathing rate begins increasing), for example.

At 785, the medical personnel remove the various patient monitoring devices from the patient. The surgical computing system may collect information regarding the conclusion of the procedure. For example, the surgical computing system may collect information related to the loss of EKG, BP, and other data from the patient monitoring devices.

The surgical information 762 (including the surgical information 766) may be structured and/or labeled. The surgical computing system may provide such structure and/or labeling inherently in the data collection. For example, in surgical information 762 may be labeled according to a particular characteristic, a desired result (e.g., efficiency, patient outcome, cost, and/or a combination of the same, or the like), a certain surgical technique, an aspect of instrument use (e.g., selection, timing, and activation of a surgical instrument, the instrument's settings, the nature of the instrument's use, etc.), the identity of the health care professionals involved, a specific patient characteristic, or the like, each of which may be present in the data collection.

Surgical information (e.g., surgical information 762 collected across procedures 764) may be used in connection with one or more artificial intelligence (AI) systems. AI may be used to perform computer cognitive tasks. For example, AI may be used to perform complex tasks based on observations of data. AI may be used to enable computing systems to perform cognitive tasks and solve complex tasks. AI may include using machine learning and machine learning techniques. ML techniques may include performing complex tasks, for example, without being programmed (e.g., explicitly programmed). For example, a ML technique may improve over time based on completing tasks with different inputs. A ML process may train itself, for example using input data and/or a learning dataset.

Machine learning (ML) techniques may be employed, for example, in the medical field. For example, ML may be used on a set of data (e.g., a set of surgical data) to produce an output (e.g., reduced surgical data, processed surgical data). In examples, the output of a ML process may include identified trends or relationships of the data that were input for processing. The outputs may include verifying results and/or conclusions associated with the input data. In examples, an input to a ML process may include medical data, such as surgical images and patient scans. The ML process may output a determined medical condition based on the input surgical images and patient scans. The ML process may be used to diagnose medical conditions, for example, based on the surgical scans.

ML processes may improve themselves, for example, using the historic data that trained the ML processes and/or the input data. Therefore, ML processes may be constantly improving with added inputs and processing. The ML processes may update based on input data. For example, over time, a ML process that produces medical conclusions based on medical data may improve and become more accurate and consistent in medical diagnoses.

ML processes may be used to solve different complex tasks (e.g., medical tasks). For example, ML processes may be used for data reduction, data preparation, data processing, trend identification, conclusion determination, medical diagnoses, and/or the like. For example, ML processes may take in surgical data as an input and process the data to be used for medical analysis. The processed data may be used to determine a medical diagnosis. In the end, the ML processes may take raw surgical data and generate useful medical information (e.g., medical trends and/or diagnoses) associated with the raw surgical data.

ML processes may be combined to perform different discrete tasks on an input data set. For example, a ML process may include testing different combinations of ML sub-processes performing discrete tasks to determine which combination of ML sub-processes performs the best (e.g., competitive usage of different process/algorithm types and training to determine the best combination for a dataset). For example, the ML process may include sub-process (e.g., algorithm) control and monitoring to improve and/or verify results and/or conclusions (e.g., error bounding).

A ML process may be initialized and/or setup to perform tasks. For example, the ML process may be initialized based on initialization configuration information. The initialized ML process may be untrained and/or a base ML process for performing the task. The untrained ML process may be inaccurate in performing the designated tasks. As the ML process becomes trained, the tasks may be performed more accurately.

The initialization configuration information for a ML process may include initial settings and/or parameters. For example, the initial settings and/or parameters may include defined ranges for the ML process to employ. The ranges may include ranges for manual inputs and/or received data. The ranges may include default ranges and/or randomized ranges for variables not received, for example, which may be used to complete a dataset for processing. For example, if a dataset is missing a data range, the default data range may be used as a substitute to perform the ML process.

The initialization configuration information for a ML process may include data storage locations. For example, locations or data storages and/or databases associated with data interactions may be included. The databases associated with data interactions may be used to identify trends in datasets. The databases associated with data interactions may include mappings of data to a medical condition. For example, a database associated with data interactions may include a mapping for heart rate data to medical conditions, such as, for example, arrythmia and/or the like.

The initialization configuration information may include parameters associated with defining the system. The initialization configuration information may include instructions (e.g., methods) associated with displaying, confirming, and/or providing information to a user. For example, the initialization configuration may include instructions to the ML process to output the data in a specific format for visualization for a user.

ML techniques may be used, for example, to perform data reduction. ML techniques for data reductions may include using multiple different data reduction techniques. For example, ML techniques for data reductions may include using one or more of the following: CUR matrix decomposition; a decision tree; expectation-maximization (EM) processes (e.g., algorithms); explicit semantic analysis (ESA); exponential smoothing forecast; generalized linear model; k-means clustering (e.g., nearest neighbor); Naive Bayes; neural network processes; a multivariate analysis; an o-cluster; a singular value decomposition; Q-learning; a temporal difference (TD); deep adversarial networks; support vector machines (SVM); linear regression; reducing dimensionality; linear discriminant analysis (LDA); adaptive boosting (e.g., AdaBoost); gradient descent (e.g., Stochastic gradient descent (SGD)); outlier detection; and/or the like.

ML techniques may be used to perform data reduction, for example, using CUR matrix decompositions. A CUR matrix decomposition may include using a matrix decomposition model (e.g., process, algorithm), such as a low-rank matrix decomposition model. For example, CUR matrix decomposition may include a low-rank matrix decomposition process that is expressed (e.g., explicitly expressed) in a number (e.g., small number) of columns and/or rows of a data matrix (e.g., the CUR matrix decomposition may be interpretable). CUR matrix decomposition may include selecting columns and/or rows associated with statistical leverage and/or a large influence in the data matrix. Using CUR matrix decomposition may enable identification of attributes and/or rows in the data matrix. The simplification of a larger dataset (e.g., using CUR matrix decomposition) may enable review and interaction (e.g., with the data) by a user. CUR matrix decomposition may facilitate regression, classification, clustering, and/or the like.

ML techniques may be used to perform data reduction, for example, using decision trees (e.g., decision tree model). Decision trees may be used, for example, as a framework to quantify values of outcomes and/or the probabilities of outcomes occurring. Decision trees may be used, for example, to calculate the value of uncertain outcome nodes (e.g., in a decision tree). Decision trees may be used, for example, to calculate the value of decision nodes (e.g., in a decision tree). A decision tree may be a model to enable classification and/or regression (e.g., adaptable to classification and/or regression problems). Decision trees may be used to analyze numerical (e.g., continuous values) and/or categorical data. Decision trees may be more successful with large data sets and/or may be more efficient (e.g., as compared to other data reduction techniques).

Decision trees may be used in combination with other decision trees. For example, a random forest may refer to a collection of decision trees (e.g., ensemble of decision trees). A random forest may include a collection of decision trees whose results may be aggregated into a result. A random forest may be a supervised learning algorithm. A random forest may be trained, for example, using a bagging training process.

A random decision forest (e.g., random forest) may add randomness (e.g., additional randomness) to a model, for example, while growing the trees. A random forest may be used to search for a best feature among a random subset of features, for example, rather than searching for the most important feature (e.g., while splitting a node). Searching for the best feature among a random subset of features may result in a wide diversity that may result in a better (e.g., more efficient and/or accurate) model.

A random forest may include using parallel ensembling. Parallel ensembling may include fitting (e.g., several) decision tree classifiers in parallel, for example, on different data set sub-samples. Parallel ensembling may include using majority voting or averages for outcomes or final results. Parallel ensembling may be used to minimize overfitting and/or increase prediction accuracy and control. A random forest with multiple decision trees may (e.g., generally) be more accurate than a single decision tree-based model. A series of decision trees with controlled variation may be built, for example, by combining bootstrap aggregation (e.g., bagging) and random feature selection.

ML techniques may be used to perform data reduction, for example, using an expectation maximization (EM) model (e.g., process, algorithm). For example, an EM model may be used to find a likelihood (e.g., local maximum likelihood) parameter of a statistical model. An EM model may be used for cases where equations may not be solved directly. An EM model may consider latent variables and/or unknown parameters and known data observations. For example, the EM model may determine that missing values exist in a data set. The EM model receive configuration information indicating to assume the existence of missing (e.g., unobserved) data points in a data set.

An EM model may use component clustering. For example, component clustering may enable the grouping of EM components into high-level clusters. Components may be treated as clustered, for example, if component clustering is disabled (e.g., in an EM model).

ML techniques may be used to perform data reduction, for example, using explicit semantic analysis (ESA). ESA may be used at a level of semantics (e.g., meaning) rather than on vocabulary (e.g., surface form vocabulary) of words or a document. ESA may focus on the meaning of a set of text, for example, as a combination of the concepts found in the text. ESA may be used in document classification. ESA may be used for a semantic relatedness calculation (e.g., how similar in meaning words or pieces of text are to each other). ESA may be used for information retrieval.

ESA may be used in document classification, for example. Document classification may include tagging documents for managing and sorting. Tagging a document (e.g., with a keyword) may allow for easier searching. Keyword tagging (e.g., only using keyword tagging) may limit the accuracy and/or efficiency of document classification. For example, using keyword tagging may uncover (e.g., only uncover) documents with the keywords and not documents with words with similar meaning to the keywords. Classifying text semantically (e.g., using ESA) may improve a model's understanding of text. Classifying text semantically may include representing documents as concepts and lowering dependence on specific keywords.

ML techniques may be used to perform data reduction, for example, using an exponential smoothing forecast model. Exponential smoothing may be used to smooth time series data, for example, using an exponential window function. For example, in a moving average, past observations may be weighted equally, but exponential functions may be used to assign exponentially decreasing weights over time.

ML techniques may be used to perform data reduction, for example, using linear regression. Linear regression may be used to predict continuous outcomes. For example, linear regression may be used to predict the value of a variable (e.g., dependent variable) based on the value of a different variable (e.g., independent variable). Linear regression may apply a linear approach for modeling a relationship between a scalar response and one or more explanatory variables (e.g., dependent and/or independent variables). Simple linear regression may refer to linear regression use cases associated with one explanatory variable. Multiple linear regression may refer to linear regression use cases associated with more than one explanatory variables. Linear regression may model relationships, for example, using linear predictor functions. The linear predictor functions may estimate unknown model parameters from a data set.

For example, linear regression may be used to identify patterns within a training dataset. The identified patterns may relate to values and/or label groupings. The model may learn a relationship between the (e.g., each) label and the expected outcomes. After training, the model may be used on raw data outside the training data set (e.g., data without a mapped and/or known output). The trained model using linear regression may determine calculated predictions associated with the raw data, for example, such as identifying seasonal changes in sales data.

ML techniques may be used to perform data reduction, for example, a generalized linear model (GLM). A GLM may be used as a flexible generalization of linear regression. GLM may generalize linear regression, for example, by enabling a linear model to be related to a response variable.

ML techniques may be used to perform data reduction, for example, using k-means clustering (e.g., a nearest neighbor model). K-means clustering may be used for vector quantization. K-means clustering may be used in signal processing. K-means clustering may be aimed at partitioning n observations into k clusters, for example, where each observation is classified into a cluster with the closest mean.

K-means clustering may include K-Nearest Neighbors (KNN) learning. KNN may be an instance-based learning (e.g., non-generalized learning, lazy learning). KNN may refrain from constructing a general internal model. KNN may include storing instances corresponding to training data in an n-dimensional space. KNN may use data and classify data points, for example, based on similarity measures (e.g., Euclidean distance function). Classification may be computed, for example, based on a majority vote of the k nearest neighbors of a (e.g., each) point. KNN may be robust for noisy training data. Accuracy may depend on data quality (e.g., for KNN). KNN may include choosing a number of neighbors to be considered (e.g., optimal number of neighbors to be considered). KNN may be used for classification and/or regression.

ML techniques may be used to perform data reduction, for example, using a Naive Bayes model (e.g., process). A Naive Bayes model may be used, for example, to construct classifiers. A Naive Bayes model may be used to assign class labels to problem instances (e.g., represented as vectors of feature values). The class labels may be drawn from a set (e.g., finite set). Different processes (e.g., algorithms) may be used to train the classifiers. A family of processes (e.g., family of algorithms) may be used. The family of processes may be based on a principle where the Naive Bayes classifiers (e.g., all the Naive Bayes) classifiers assume that the value of a feature is independent of the value of a different feature (e.g., given the class variable).

ML techniques may be used to perform data reduction, for example, using a neural network. Neural networks may learn (e.g., be trained) by processing examples, for example, to perform other tasks (e.g., similar tasks). A processing example may include an input and a result (e.g., input mapped to a result). The neural network may learn by forming probability-weighted associations between the input and the result. The probability-weighted associations may be stored within a data structure of the neural network. The training of the neural network from a given example may be conducted by determining the difference between a processed output of the network (e.g., prediction) and a target output. The difference may be the error. The neural network may adjust the weighted associations (e.g., stored weighted associations), for example, according to a learning rule and the error value.

ML techniques may be used to perform data reduction, for example, using multivariate analysis. Multivariate analysis may include performing multivariate state estimation and/or non-negative matrix factorization.

ML techniques may be used to perform data reduction, for example, using support vector machines (SVMs). SVMs may be used in a multi-dimensional space (e.g., high-dimensional space, infinite-dimensional space). SVCs may be used to construct a hyper-plane (e.g., set of hyper-planes). A hyper-plane that has the greatest distance (e.g., compared to the other constructed hyper-planes) from a nearest training data point in a class (e.g., any class) may achieve a strong separation (e.g., in general, the greater the margin, the lower the classifier's generalization error). SVMs may be effective in high-dimensional spaces. SVMs may behave differently, for example, based on different mathematical functions (e.g., the kernel, kernel functions). For example, kernel functions may include one or more of the following: linear, polynomial, radial basis function (RBF), sigmoid, etc. The kernel functions may be used as a SVM classifier. SVM may be limited in use cases, for example, where a data set contains high amounts of noise (e.g., overlapping target classes).

ML techniques may be used to perform data reduction, for example, such as reducing dimensionality. Reducing dimensionality of a sample of data (e.g., unlabeled data) may help refine groups and/or clusters. Reducing a number of variables in a model may simplify data trends. Simplified data trends may enable more efficient processing. Reducing dimensionality may be used, for example, if many (e.g., too many) dimensions are clouding (e.g., negatively affecting) insights, trends, patterns, conclusions, and/or the like.

Reducing dimensionality may include using principal component analysis (PCA). PCA may be used to establish principal components that govern a relationship between data points. PCA may focus on simplifying (e.g., only simplifying) the principal components. Reducing dimensionality (e.g., PCA) may be used to maintain the variety of data grouping in a data set, but streamline the number of separate groups.

ML techniques may be used to perform data reduction, for example, linear discriminant analysis (LDA). LDA may refer to a linear decision boundary classifier, for example, that may be created by fitting class conditional densities to data (e.g., and applying Bayes' rule). LDA may include a generalization of Fisher's linear discriminant (e.g., projecting a given dataset into lower-dimensional space, for example, to reduce dimensionality and minimize complexity of a model and reduce computational costs). An LDA model (e.g., standard LDA model) may suit a class with a Gaussian density. The LDA model may assume that the classes (e.g., all classes) share a covariance matrix. LDA may be similar to analysis of variance (ANOVA) processes and/or regression analysis. For example, LDA may be used to express a dependent variable as a linear combination of other features and/or measurements.

ML techniques may be used to perform data reduction, for example, such as adaptive boosting (e.g., AdaBoost). Adaptive boosting may include creating a classifier (e.g., powerful classifier). Adaptive boosting may include creating a classier by combining multiple classifiers (e.g., poorly performing classifiers), for example, to obtain a resulting classifier with high accuracy. AdaBoost may be an adaptive classifier that improves the efficiency of a classifier. AdaBoost may trigger overfits. AdaBoost may be used (e.g., best used) to boost the performance of decision trees, base estimator(s), binary classification problems, and/or the like. AdaBoost may be sensitive to noisy data and/or outliers.

ML techniques may be used to perform data reduction, for example, such as stochastic gradient descent (SGD). SGD may include an iterative process used to optimize a function (e.g., objective function). SGD may be used to optimize an objective function, for example, with certain smoothness properties. Stochastic may refer to random probability. SGD may be used to reduce computational burden, for example, in high-dimensional optimization problems. SGD may be used to enable faster iterations, for example, while exchanging for a lower convergence rate. A gradient may refer to the slop of a function, for example, that calculates a variable's degree of change in response to another variable's changes. Gradient descent may refer to a convex function that outputs a partial derivative of a set of its input parameters. For example, a may be a learning rate and Ji may be a training example cost of the ith iteration. The equation may represent the stochastic gradient descent weight update method at the jth iteration. In large-scale ML and sparse ML, SGD may be applied to problems in text classification and/or natural language processing (NLP). SGD may be sensitive to feature scaling (e.g., may need to use a range of hyperparameters, for example, such as a regularization parameter and a number of iterations).

ML techniques may be used to perform data reduction, for example, such as using outlier detection. An outlier may be a data point that contains information (e.g., useful information) on an abnormal behavior of a system described by the data. Outlier detection processes may include univariate processes and multivariate processes.

ML processes may be trained, for example, using one or more training methods. For example, ML processes may be trained using one or more of the following training techniques: supervised learning; unsupervised learning; semi-supervised learning; reinforcement learning; and/or the like.

Figure 8A:
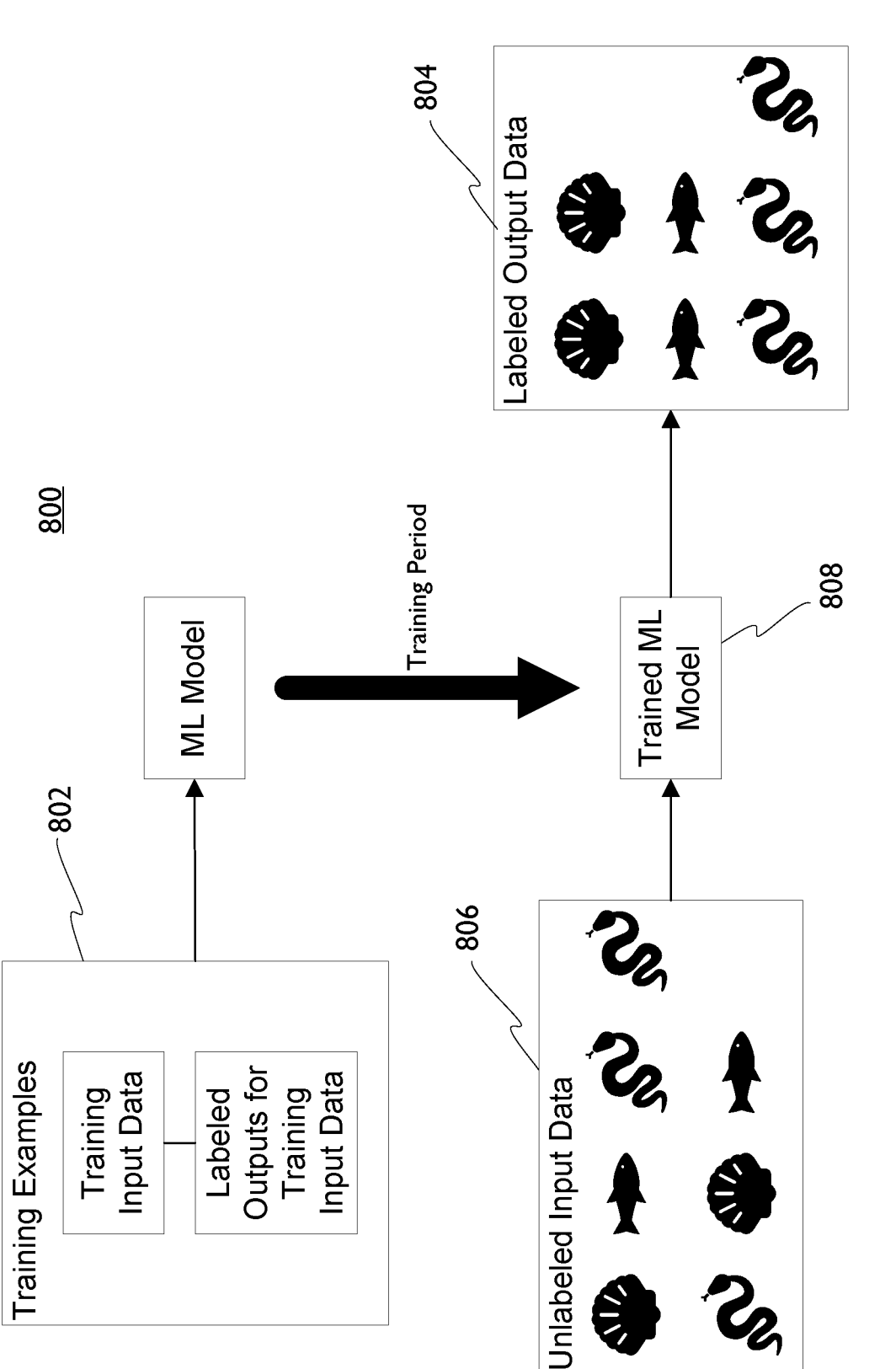
FIGS. 8A&B show an example supervised learning framework and an example unsupervised learning framework, respectively.

Machine learning may be supervised (e.g., supervised learning). A supervised learning algorithm may create a mathematical model from training a dataset (e.g., training data). FIG. 8A illustrates an example supervised learning framework 800. The training data (e.g., training examples 802, for example, as shown in FIG. 8A) may consist of a set of training examples (e.g., input data mapped to labeled outputs, for example, as shown in FIG. 8A). A training example 802 may include one or more inputs and one or more labeled outputs. The labeled output(s) may serve as supervisory feedback. In a mathematical model, a training example 802 may be represented by an array or vector, sometimes called a feature vector. The training data may be represented by row(s) of feature vectors, constituting a matrix. Through iterative optimization of an objective function (e.g., cost function), a supervised learning algorithm may learn a function (e.g., a prediction function) that may be used to predict the output associated with one or more new inputs. A suitably trained prediction function (e.g., a trained ML model 808) may determine the output 804 (e.g., labeled outputs) for one or more inputs 806 that may not have been a part of the training data (e.g., input data without mapped labeled outputs, for example, as shown in FIG. 8A). Example algorithms may include linear regression, logistic regression, neutral network, nearest neighbor, Naive Bayes, decision trees, SVM, and/or the like. Example problems solvable by supervised learning algorithms may include classification, regression problems, and the like.

Figure 8B:
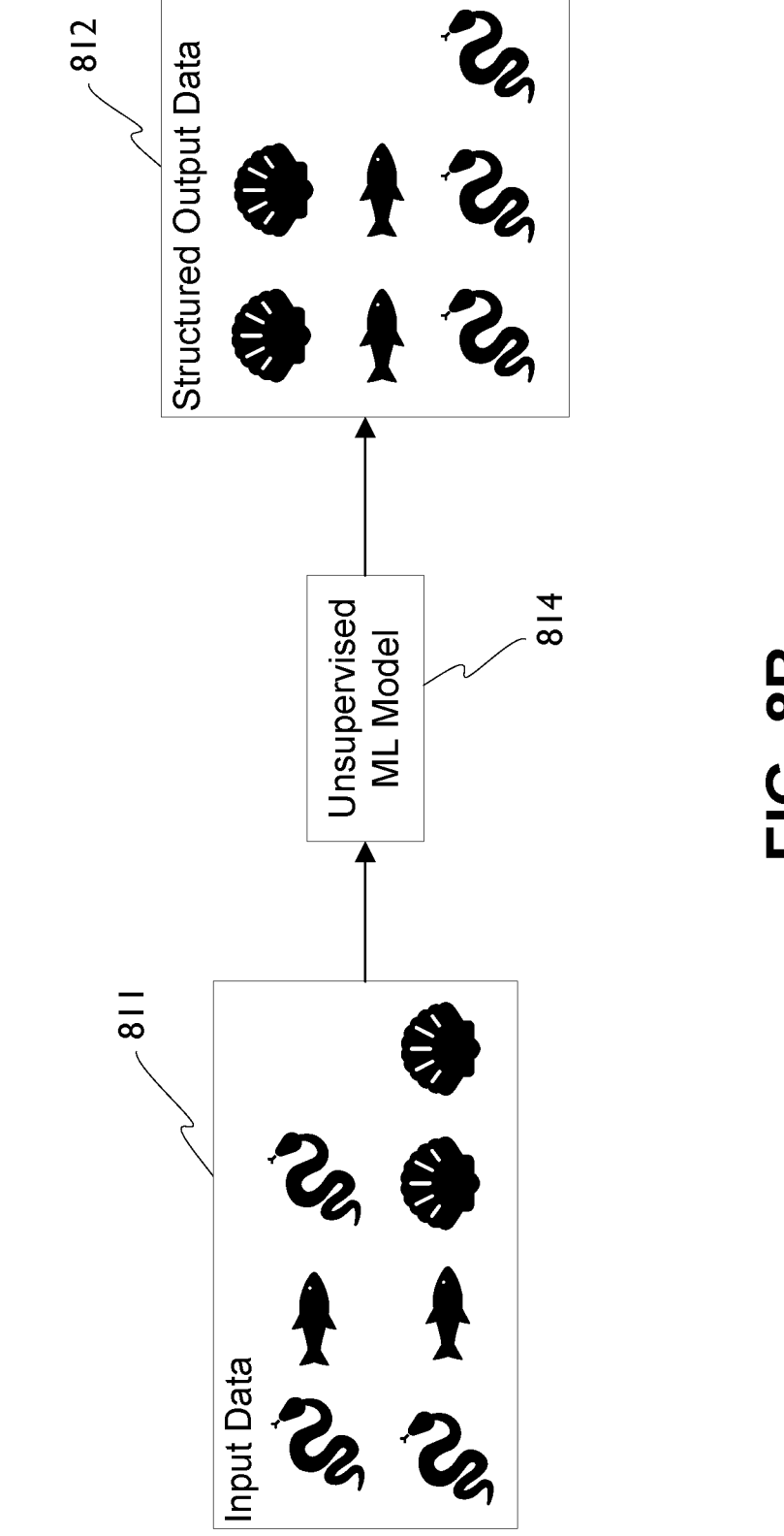

Machine learning may be unsupervised (e.g., unsupervised learning). FIG. 8B illustrates an example unsupervised learning framework 810. An unsupervised learning algorithm 814 may train on a dataset that may contain inputs 811 and may find a structure 812 (e.g., pattern detection and/or descriptive modeling) in the data. The structure 812 in the data may be similar to a grouping or clustering of data points. As such, the algorithm 814 may learn from training data that may not have been labeled. Instead of responding to supervisory feedback, an unsupervised learning algorithm may identify commonalities in training data and may react based on the presence or absence of such commonalities in each training datum. For example, the training may include operating on a training input data to generate an model and/or output with particular energy (e.g., such as a cost function), where such energy may be used to further refine the model (e.g., to define model that minimizes the cost function in view of the training input data). Example algorithms may include Apriori algorithm, K-Means, K-Nearest Neighbors (KNN), K-Medians, and the like. Example problems solvable by unsupervised learning algorithms may include clustering problems, anomaly/outlier detection problems, and the like Machine learning may be semi-supervised (e.g., semi-supervised learning). A semi-supervised learning algorithm may be used in scenarios where a cost to label data is high (e.g., because it requires skilled experts to label the data) and there are limited labels for the data. Semi-supervised learning models may exploit an idea that although group memberships of unlabeled data are unknown, the data still carries important information about the group parameters.

Machine learning may include reinforcement learning, which may be an area of machine learning that may be concerned with how software agents may take actions in an environment to maximize a notion of cumulative reward. Reinforcement learning algorithms may not assume knowledge of an exact mathematical model of the environment (e.g., represented by Markov decision process (MDP)) and may be used when exact models may not be feasible. Reinforcement learning algorithms may be used in autonomous vehicles or in learning to play a game against a human opponent. Examples algorithms may include Q-Learning, Temporal Difference (TD), Deep Adversarial Networks, and/or the like.

Reinforcement learning may include an algorithm (e.g., agent) continuously learning from the environment in an iterative manner. In the training process, the agent may learn from experiences of the environment until the agent explores the full range of states (e.g., possible states). Reinforcement learning may be defined by a type of problem. Solutions of reinforcement learning may be classed as reinforcement learning algorithms. In a problem, an agent may decide an action (e.g., the best action) to select based on the agent's current state. If a step if repeated, the problem may be referred to as an MDP.

For example, reinforcement learning may include operational steps. An operation step in reinforcement learning may include the agent observing an input state. An operation step in reinforcement learning may include using a decision making function to make the agent perform an action. An operation step may include (e.g., after an action is performed) the agent receiving a reward and/or reinforcement from the environment. An operation step in reinforcement learning may include storing the state-action pair information about the reward.

Machine learning may be a part of a technology platform called cognitive computing (CC), which may constitute various disciplines such as computer science and cognitive science. CC systems may be capable of learning at scale, reasoning with purpose, and interacting with humans naturally. By means of self-teaching algorithms that may use data mining, visual recognition, and/or natural language processing, a CC system may be capable of solving problems and optimizing human processes.

The output of machine learning's training process may be a model for predicting outcome(s) on a new dataset. For example, a linear regression learning algorithm may be a cost function that may minimize the prediction errors of a linear prediction function during the training process by adjusting the coefficients and constants of the linear prediction function. When a minimal may be reached, the linear prediction function with adjusted coefficients may be deemed trained and constitute the model the training process has produced. For example, a neural network (NN) algorithm (e.g., multilayer perceptrons (MLP)) for classification may include a hypothesis function represented by a network of layers of nodes that are assigned with biases and interconnected with weight connections. The hypothesis function may be a non-linear function (e.g., a highly non-linear function) that may include linear functions and logistic functions nested together with the outermost layer consisting of one or more logistic functions. The NN algorithm may include a cost function to minimize classification errors by adjusting the biases and weights through a process of feedforward propagation and backward propagation. When a global minimum may be reached, the optimized hypothesis function with its layers of adjusted biases and weights may be deemed trained and constitute the model the training process has produced.

Data collection may be performed for machine learning as a first stage of the machine learning lifecycle. Data collection may include steps such as identifying various data sources, collecting data from the data sources, integrating the data, and the like. For example, for training a machine learning model for predicting surgical complications and/or post-surgical recovery rates, data sources containing pre-surgical data, such as a patient's medical conditions and biomarker measurement data, may be identified. Such data sources may be a patient's electronical medical records (EMR), a computing system storing the patient's pre-surgical biomarker measurement data, and/or other like data-stores. The data from such data sources may be retrieved and stored in a central location for further processing in the machine learning lifecycle. The data from such data sources may be linked (e.g. logically linked) and may be accessed as if they were centrally stored. Surgical data and/or post-surgical data may be similarly identified, collected. Further, the collected data may be integrated. In examples, a patient's pre-surgical medical record data, pre-surgical biomarker measurement data, pre-surgical data, surgical data, and/or post-surgical may be combined into a record for the patient. The record for the patient may be an EMR.

Data preparation may be performed for machine learning as another stage of the machine learning lifecycle. Data preparation may include data preprocessing steps such as data formatting, data cleaning, and data sampling. For example, the collected data may not be in a data format suitable for training a model. Such data record may be converted to a flat file format for model training. Such data may be mapped to numeric values for model training. Such identifying data may be removed before model training. For example, identifying data may be removed for privacy reasons. As another example, data may be removed because there may be more data available than may be used for model training. In such case, a subset of the available data may be randomly sampled and selected for model training and the remainder may be discarded.

Data preparation may include data transforming procedures (e.g., after preprocessing), such as scaling and aggregation. For example, the preprocessed data may include data values in a mixture of scales. These values may be scaled up or down, for example, to be between 0 and 1 for model training. For example, the preprocessed data may include data values that carry more meaning when aggregated.

Model training may be another aspect of the machine learning lifecycle. The model training process as described herein may be dependent on the machine learning algorithm used. A model may be deemed suitably trained after it has been trained, cross validated, and tested. Accordingly, the dataset from the data preparation stage (e.g., an input dataset) may be divided into a training dataset (e.g., 60% of the input dataset), a validation dataset (e.g., 20% of the input dataset), and a test dataset (e.g., 20% of the input dataset). After the model has been trained on the training dataset, the model may be run against the validation dataset to reduce overfitting. If accuracy of the model were to decrease when run against the validation dataset when accuracy of the model has been increasing, this may indicate a problem of overfitting. The test dataset may be used to test the accuracy of the final model to determine whether it is ready for deployment or more training may be required.

Model deployment may be another aspect of the machine learning lifecycle. The model may be deployed as a part of a standalone computer program. The model may be deployed as a part of a larger computing system. A model may be deployed with model performance parameters(s). Such performance parameters may monitor the model accuracy as it is used for predicating on a dataset in production. For example, such parameters may keep track of false positives and false positives for a classification model. Such parameters may further store the false positives and false positives for further processing to improve the model's accuracy.

Post-deployment model updates may be another aspect of the machine learning cycle. For example, a deployed model may be updated as false positives and/or false positives are predicted on production data. In an example, for a deployed MLP model for classification, as false positives occur, the deployed MLP model may be updated to increase the probably cutoff for predicting a positive to reduce false positives. In an example, for a deployed MLP model for classification, as false negatives occur, the deployed MLP model may be updated to decrease the probably cutoff for predicting a positive to reduce false negatives. In an example, for a deployed MLP model for classification of surgical complications, as both false positives and false negatives occur, the deployed MLP model may be updated to decrease the probably cutoff for predicting a positive to reduce false negatives because it may be less critical to predict a false positive than a false negative.

For example, a deployed model may be updated as more live production data become available as training data. In such case, the deployed model may be further trained, validated, and tested with such additional live production data. In an example, the updated biases and weights of a further-trained MLP model may update the deployed MLP model's biases and weights. Those skilled in the art recognize that post-deployment model updates may not be a one-time occurrence and may occur as frequently as suitable for improving the deployed model's accuracy.

ML techniques may be used independently of each other or in combination. Different problems and/or datasets may benefit from using different ML techniques (e.g., combinations of ML techniques). Different training types for models may be better suited for a certain problem and/or dataset. An optimal algorithm (e.g., combination of ML techniques) and/or training type may be determined for a specific usage, problem, and/or dataset. For example, a process may be performed to for one or more of the following: choose a data reduction type, choose a configuration for a model and/or algorithm, determine a location for the data reduction, choose an efficiency of the reduction and/or result, and/or the like.

For example, a ML technique and/or combination of ML techniques may be determined for a particular problem and/or use case. Multiple data reduction and/or data analysis processes may be performed to determine accuracy, efficiency, and/or compatibility associated with a dataset. For example, a first ML technique (e.g., first set of combined ML techniques) may be used on a dataset to perform data reduction and/or data analysis. The first ML technique may produce a first output. Similarly, a second ML technique (e.g., second set of combined ML techniques) may be used on the dataset (e.g., same dataset) to perform data reduction and/or data analysis. The second ML technique may produce a second output. The first output may be compared with the second output to determine which ML technique produced more desirable results (e.g., more efficient results, more accurate results). Multiple ML techniques may be compared with the same dataset to determine the optimal ML technique(s) to use on a future similar dataset and/or problem.

In examples, in a medical context, a surgeon or healthcare professional may give feedback to ML techniques and/or models used on a dataset. The surgeon may input feedback to weighted results of a ML model. The feedback may be used as an input by the model to determine a reduction method for future analyses.

In examples, a data analysis method (e.g., ML techniques to be used in the data analysis method) may be determined based on the dataset itself. For example, the origin of the data may influence the type of data analysis method to be used on the dataset. System resources available may be used to determine the data analysis method to be used on a given dataset. The data magnitude, for example, may be considered in determining a data analysis method. For example, the need for datasets exterior to the local processing level or magnitude of operational responses may be considered (e.g., small device changes may be made with local data, major device operation changes may require global compilation and verification).

Such ML techniques may be applied to surgical information (e.g., a combination of information flows of surgical information in FIGS. 7A-D) to generate useful ML models.

Systems, methods, and instrumentalities are disclosed for using interrelated machine learning (ML) models (e.g., algorithms). The interrelated ML models may act collectively to perform complimentary portions of a surgical analysis. The ML models may be used at various locations. For example, ML models may be implemented in a facility network, a cloud network, an edge network, and/or the like. The location of the ML models may influence the type of data the ML models process. For example, ML models used outside a HIPAA boundary (e.g., cloud network) may process non-private and/or non-confidential information. The ML models may be used to feed their respective results into other ML models to provide a more complete result.

For example, a computing system may include a processor that may implement interrelated ML models. The computing system may determine sets of data (e.g., first set of data, second set of data, etc.) to be sent to ML models for processing. The sets of data may be determined, for example, based on the processing task associated with the ML model the set of data is to process. The computing system may generate (e.g., using a machine learning model) an output based on a set of data. Multiple ML models may process different sets of data. The outputs from the different ML models may be fed into subsequent ML model(s), for example, for additional processing. The subsequent ML model(s) may receive the outputs from the interrelated ML models and/or other sets of data. The subsequent ML model(s) may generate a result based on the received outputs and/or sets of data.

The processing tasks associated with the ML model(s) may be associated with surgical data processing. For example, the ML model(s) may be associated with data preparation, data reduction, trend analysis, recommendation determination, and/or the like.

Surgical data may be prepared and/or processed to provide medical insights on the surgical data. For example, surgical data for a live surgical procedure may provide insights on the live surgical procedure. The insights may give context to health care professionals (HCPs) in the surgical theater performing the live surgical procedure. For example, the HCPs may be informed by the insights about certain events and/or recommendations associated with the live surgical procedure. Insights on the surgical data may indicate that a patient is experiencing a higher heart rate than may be normal for the surgical procedure and/or surgical procedure step. Insights may be valuable to HCPs and/or medical training. Insights give context to surgical procedures and the medical field.

Machine learning (ML) may be used, for example, in the medical field to receive raw surgical data for processing to produce helpful information. For example, machine learning may be used to pre-process the surgical data for HCPs to perform analyses. Pre-processing data may include data reduction, data clean up, and/or data completion. Machine learning may be used on prepared surgical data, for example, to perform surgical analysis on the prepared surgical data. For example, ML may be used to identify trends, patterns, and/or relationships in the data. ML may be used, for example, to determine methodologies on how to communicate the identified trends, patterns and/or relationships. For example, ML may be used to determine surgical recommendations (e.g., on the fly adaptations of control programs) based on surgical data, and the ML may be used to communicate the recommendations to a user (e.g., HCP, surgeon, nurse).

Multiple ML processes (e.g., techniques, algorithms, models) may be used on the surgical data. For example, separate but interrelated ML models may be used in conjunction with each other to identify different portions of a surgical analysis (e.g., data preparation, relationships within the data, methodologies of how to communicate the recommendations, or on the fly adaptations of control programs. For example, a first ML model may be used to prepared raw surgical data and output a first set of data to be used for pattern identification. A second ML model may use the first set of data to identify patterns within the first set of data. The second ML model may output a second set of data that indicates relationships within the first set of data. A third ML model may receive the second set of data and determine a method of communicating the data, which may be output to as a third set of data. In the end, the identified patterns of the surgical data may be communicated to a user. The ML models in conjunction may be used to take raw surgical data and produce helpful surgical insights in a digestible manner to a user.

Figure 9:
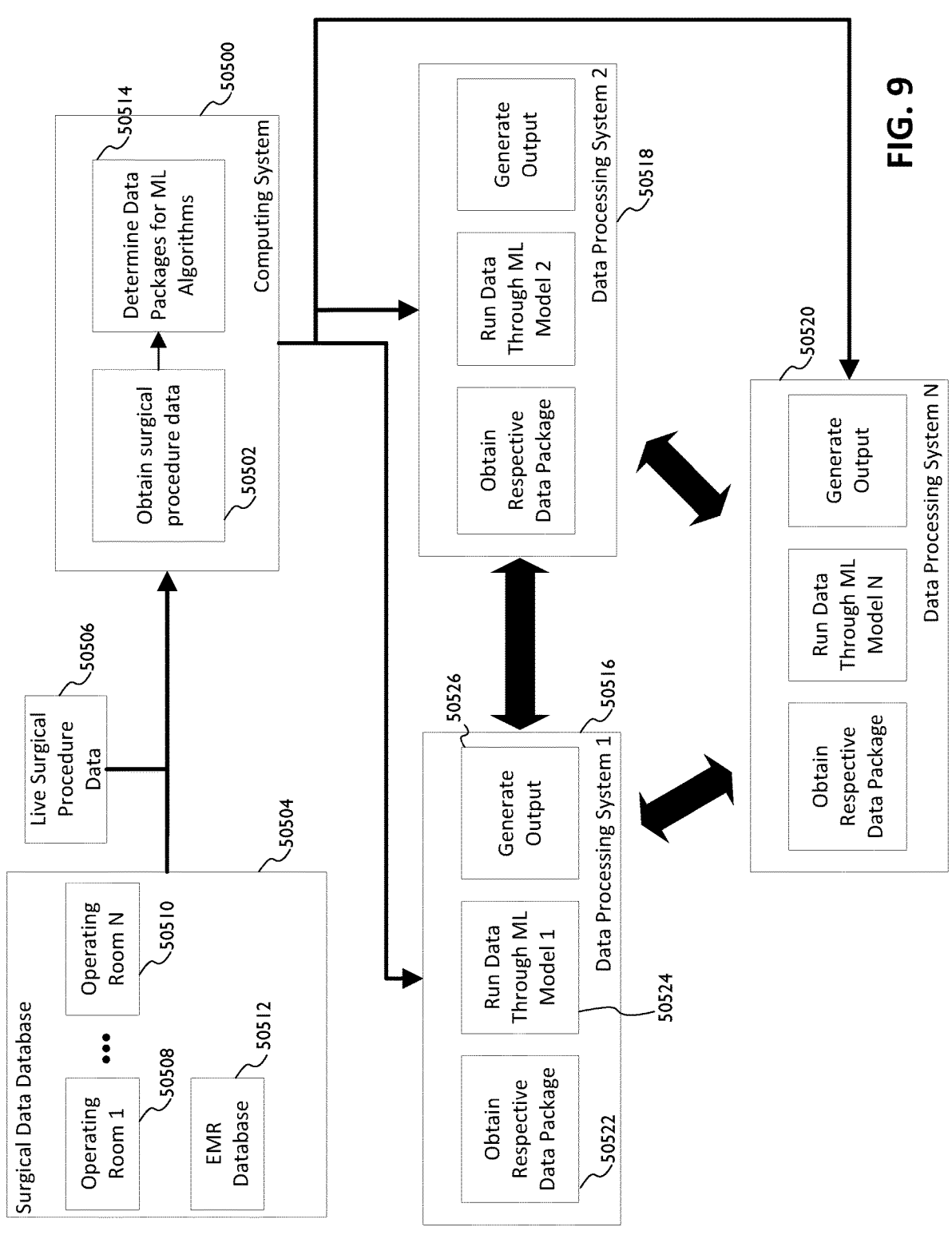
FIG. 9 illustrates an example of using interrelated ML algorithms to perform different portions of analysis for surgical data

FIG. 9 illustrates an example of using interrelated ML algorithms to perform different portions of analysis for surgical data. As shown in FIG. 9 at 50502, a computing system 50500 may receive surgical data (e.g., surgical procedure data). The surgical procedure data may include surgical data from a surgical data database 50504 and/or live surgical procedure data 50506. Surgical data from the surgical data database 50504 may include surgical data from different operating rooms (e.g., such as Operating Room 1 50508, Operating Room N 50510, etc.), data from an electronic medical record database (e.g., associated with a particular patient) 50512, and/or the like. As shown in FIG. 9 at 50514, data packages (e.g., comprising sets of the obtained surgical data) may be determined, for example, to be sent to different interrelated ML models (e.g., algorithms) for processing. For example, data packages may be sent to a first data processing system 50516, a second data processing system 50518, an Nth data processing system 50520, and/or the like.

The respective data processing systems (e.g., ML models, ML algorithms, etc.) may process their respectively obtained data packages (e.g., using ML). The first data processing system A50516 may obtain its respective data package (e.g., as shown at 50522). The first data processing system may process the data package (e.g., run data through a ML model), for example, as shown at 50524. The ML model may used to perform one or more of the data processing goals (e.g., data reduction, trend identification, recommendation determination, etc.) as described herein. The ML model may output a set of data associated with the ML model's processing goals. For example, the ML model may be used to reduce raw surgical data. The output may comprise reduced surgical data, for example, that may be used by a user and/or other ML models to produce surgical insights and/or recommendations.

As shown at 50514, the data packages for the respective data processing systems (e.g., ML models) may be determined. The data packages may be determined, for example, based on the processing task and/or goal of the respective data processing systems and/or ML models. For example, a data package for a ML model that is associated with performing data reduction may include raw surgical data that needs to be sifted through before performing accurate trend analysis. For example, raw surgical data may include various data outliers that may occur due to improper calibration of instruments and/or sensors, and/or other data collection errors. The data outliers (e.g., if considered/used during data analysis) may produce inaccurate results and/or conclusions. Removing the data outliers may allow for more accurate analysis. The ML model may identify and remove outlier data during data reduction, for example, before sending the cleaned data for analysis using a different ML model.

In examples, a data package for a data processing system (e.g., ML model) that is associated with determining a baseline surgical procedure plan may include data associated with historic surgical procedure performed on patients with similar biometrics and/or body compositions. Data from historic surgical procedures may be used to influence future surgical procedures. The data package may comprise different data that may be used to map out an optimal surgical procedure plan.

In examples, the data packages may be determined based on the processing capabilities of the ML models and/or data processing systems. For example, a data processing system may be limited based on its processing capabilities. Higher amounts of data to be processed and/or complexity of the processing task may use more processing resources. For example, a data processing system may be limited to using a threshold number of processing resources for a given task. The data packages may be determined by considering the processing power of the data processing system. For example, a local data processing system that is associated with processing lower amounts of data in a non-complex manner may receive a smaller data package than a cloud based data processing system equipped to handle databases of data for complex processing. The computing system 50500 may determine the processing capabilities associated with ML models and the data processing systems, for example, before sending the data packages.

The data processing systems may (e.g., also, in addition to the data packages from the computer system) receive outputs from the other data processing systems (e.g., interrelated ML models) as (e.g., additional) inputs for their respective processing. For example, the first data processing system 50516 may process the received data such that the output comprises reduced data (e.g., first ML algorithm performs data reduction). The reduced data may be an input to the second data processing system AA045. The reduced data may be used (e.g., in conjunction with the respective data package obtained by the second data processing system) to perform the ML algorithm associated with the second data processing system. The reduced data may enhance the outputs produced by the second data processing system (e.g., provide more accurate results, and/or allow for more efficient processing).

In examples, outputs may be determined by ML models and/or data processing systems in anticipation of sending the output to a different interrelated ML model and/or data processing system. For example, a first data processing system may process a first set of data and output a second set of data intended for a second data processing system. The second set of data may be generated based on the determined processing capabilities associated with the intended recipient of the second set of data. For example, a second data processing system may be limited to handling only non-complex processing tasks. The output of the first data processing system may take into consideration the lower processing power of the second data processing system and reduce the complexity of the data in the out and/or the amount of data in the output.

Figure 10:
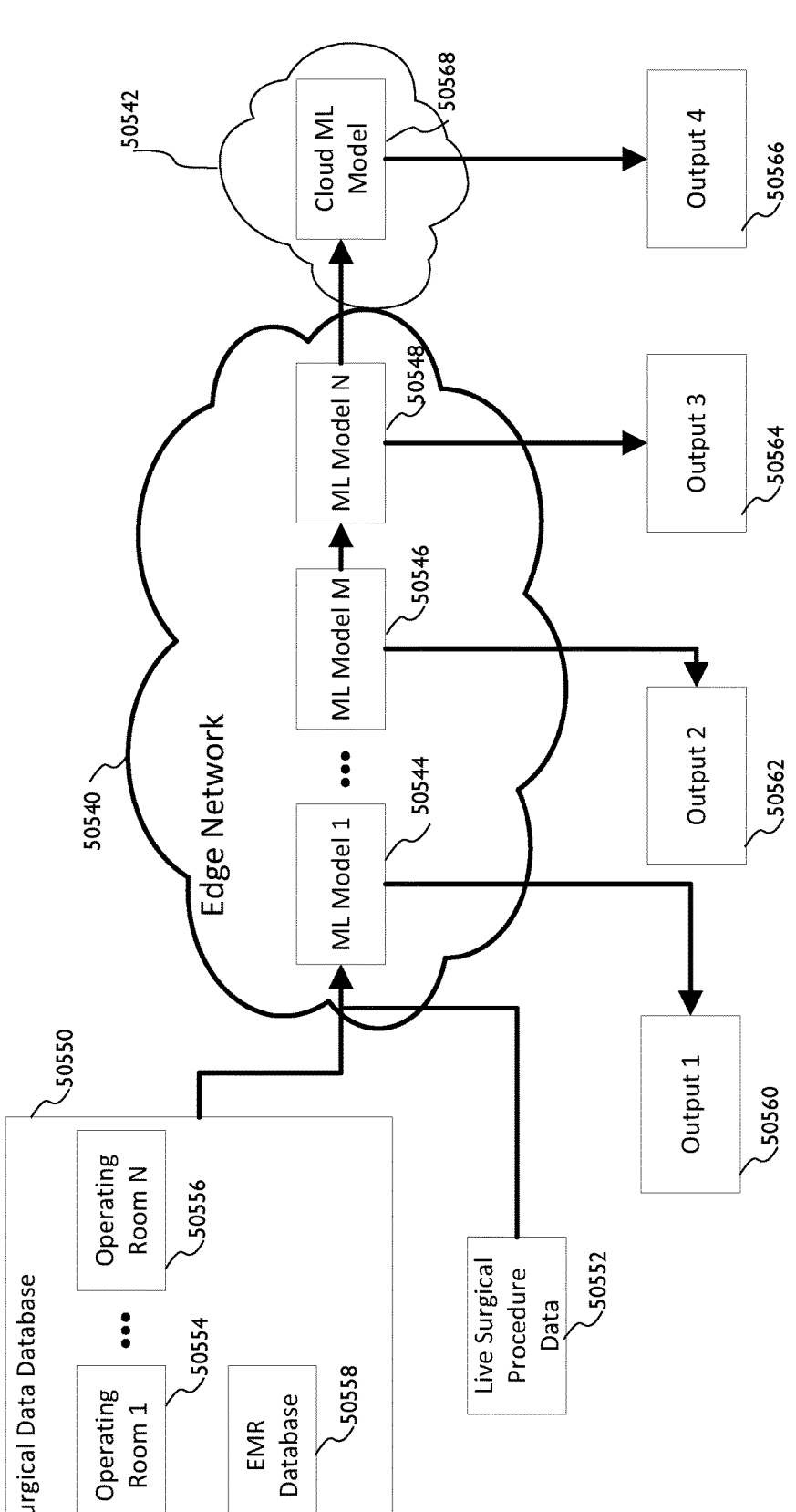
FIG. 10 illustrates an example of interrelated ML models processing data in different locations.

FIG. 10 illustrates an example of interrelated ML models processing data in different locations. As shown in FIG. 10, ML models may be used to process surgical data in an edge network 50540 or a cloud network 50542. In examples, ML models may be used to process surgical data locally (e.g., in a facility, such as a medical facility, an operating room, and/or the like). As shown in FIG. 10, surgical data may be transmitted to ML models (e.g., algorithms) for processing within different networks. The ML models (e.g., each ML model) may generate an output (e.g., and send the output to a user, storage, or further ML model for processing). The location of the data processing (e.g., ML model) may affect the type of data received for processing.

The Health Information Portability and Accountability Act may provide guidelines for handling medical data. For example, a HIPAA boundary may restrict private and/or confidential data from being sent between a protected area and an unprotected area. In examples, confidential data may be transmitted locally in a facility network and/or an edge network hosted within the facility. However, private and/or confidential data may be restricted from being transmitted beyond the HIPAA boundary (e.g., a cloud network).

Data obtained for processing may include data from a surgical data database 50550 and/or live surgical procedure data 50552. Data obtained from the surgical data database 50550 may include data from operating rooms in a medical facility (e.g., operating room 1 50554, operating room N 50556, etc.), data from electronic medical records 50558, and/or the like. The surgical data database 50550 may include at least some data classified as private and/or confidential (e.g., under HIPAA guidelines).

In examples, the data packages may be determined based on privacy concerns associated with the surgical data and the ML models (e.g., location of the ML models processing the data). Data tagged with a confidential and/or private type indicator may be refrained from being transmitted beyond the HIPAA boundary.

For example, ML models within the edge network and/or local network (e.g., of a medical facility) may receive private and/or confidential data for processing. As shown in FIG. 10, multiple ML models may be located in the edge network for processing data, such as ML Model 1 50544, ML Model M 50546, and ML Model N 50548. Based on the location of the ML models (e.g., within the HIPAA boundary in the edge network), the data received for processing may include data tagged as private and/or confidential. For example, the surgical data received for processing at ML model 1 50544, ML Model M 50546, ML Model N 50548, and/or other ML models within the edge network may receive surgical data that includes confidential and/or private data.

ML models in the cloud network (e.g., outside the HIPAA boundary) may receive surgical data that excludes confidential and/or private data. The data received as an output from a different ML model (e.g., within the HIPAA boundary) may not include the confidential and/or private data.

In examples, an ML model may generate an output specific to the destination the output is to be sent to. For example, ML Model 1 50544 may produce a first output 50560. The first output may be an input to a ML Model M 50546. ML The input to ML Model M 50546 may include private and/or confidential data, for example, because it is located within the HIPAA boundary (e.g., permitted to receive such data). Similarly, ML Model M 50546 may produce a second output 50562 (e.g., based on the input from ML Model 1 and/or an input from another source) that considers ML Model N 50548. The input to ML Model N 50548 may include private and/or confidential data, for example, because it is similarly located within the HIPAA boundary. ML Model N 50548 may generate a third output 50564 (e.g., based on the input received from ML Model M and/or a different source). The third output 50564 may be generated, for example, as an input to a Cloud ML Model 50568. The output 50564 may consider that Cloud ML Model 50568 is located in a cloud network (e.g., outside the HIPAA boundary). The Cloud ML Model 50568 may be restricted to data not containing private and/or confidential information. ML Model N 50548 may redact (e.g., remove) any confidential and/or private information in the third output 50564 (e.g., before sending to the Cloud ML Model 50568). A fourth output 50566 may be generated, for example, using the Cloud ML Model 50568.

Figure 11:
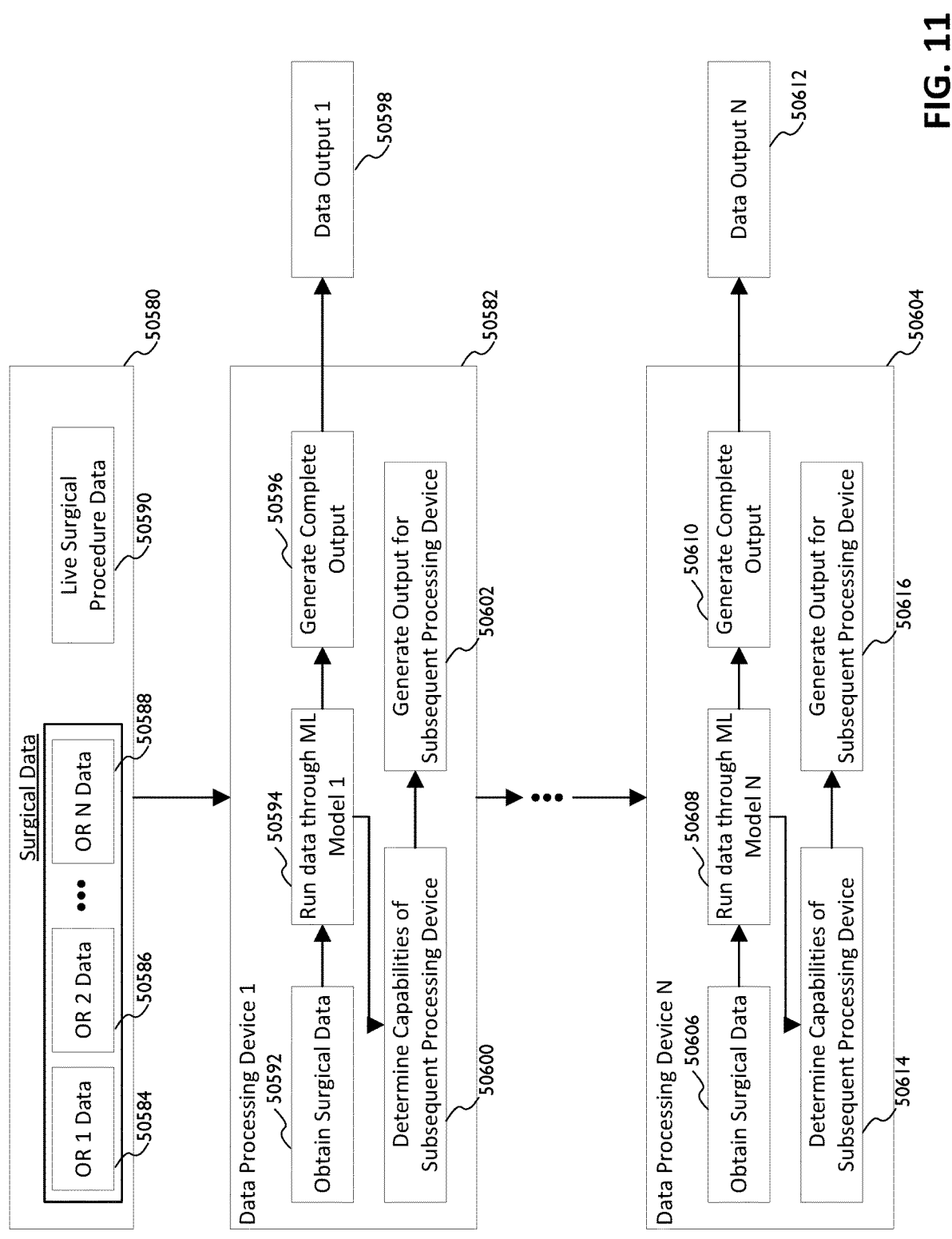
FIG. 11 illustrates an example flow of interrelated ML models generating processed data for other ML models and generating a completed set of processed data.

FIG. 11 illustrates an example flow of interrelated ML models generating processed data for other ML models and generating a completed set of processed data. ML models may process data and generate an output intended for a subsequent use and/or ML model (e.g., as described herein with respect to FIGS. 9 and 10). The ML models may general multiple outputs (e.g., different data packages). For example, a first ML model may generate a first output (e.g., to be transmitted to a second ML model) and a second output (e.g., to be transmitted to a third ML model). The first output may be generated based on the second ML model (e.g., capabilities, processing goal, etc.). The second output may be generated based on the second ML model. The first ML model may produce a third output, for example, that may include the entire output of the ML model processing. For example, a first data set may be input to the first ML model.

The ML model may process the first data set. Based on the processing, the ML model may generate a complete result including all the processed data. The ML model may further determine data packages (e.g., subsets of the complete result of the processed data), for example, to be generated for other uses (e.g., other ML models to use). For example, a first data package may be generated and output for a second ML model. The first data package may be a subset of the complete result of the processed data. A second data package may be generated and output for a third ML model. The second data package may be a subset of the complete result of the processed data (e.g., including at least a portion of different data from the first data package).

As shown in FIG. 11, surgical data 50580 may be input to a first data processing device (e.g., first ML model) 50582. The surgical data may include data (e.g., as described herein), for example, such as data associated with an operating room (e.g., OR 1 data 50584, OR 2 data 50586, OR N data 50588, etc.), live surgical procedure data 50590, and/or the like. As shown at 50592, the first data processing device 50582 may obtain the surgical data 50580 (e.g., a portion of the surgical data). The obtained surgical data may be processed, for example, using an ML model (e.g., as shown at 50594). A complete result 50596 may be generated, for example, based on the using the ML model on the obtained surgical data. The complete result 50596 may be output as a first output (e.g., as shown at 50598). The data processing device may determine capabilities (e.g., processing capabilities, privacy capabilities, etc.) associated with a subsequent processing device (e.g., subsequent ML model), for example, as shown at 50600. Based on the determined capabilities associated with the subsequent processing device, a data package (e.g., output) may be generated to be transmitted to the subsequent data processing device (e.g., as shown at 50602). The data package may be transmitted to the subsequent data processing device (e.g., as shown in FIG. 11). The subsequent data processing device may be, for example, data processing device N 50604.

Data processing device N 50604 may obtain surgical data (e.g., an output from a previous ML model and/or data processing device, such as the output from data processing device 1 50582), for example, as shown at 50606. Data processing device N 50608 may process the obtained surgical data (e.g., as shown at 50608). Similar to the previous data processing devices, a complete result may be generated based on the processing using the ML model (e.g., as shown at 50610). The complete result may be output (e.g., as shown at 50612). Similarly, data processing device N 50604 may determine a capability associated with a subsequent processing device (e.g., as shown at 50614) to generate an output for the subsequent processing device (e.g., as shown at 50616).

Figure 12:
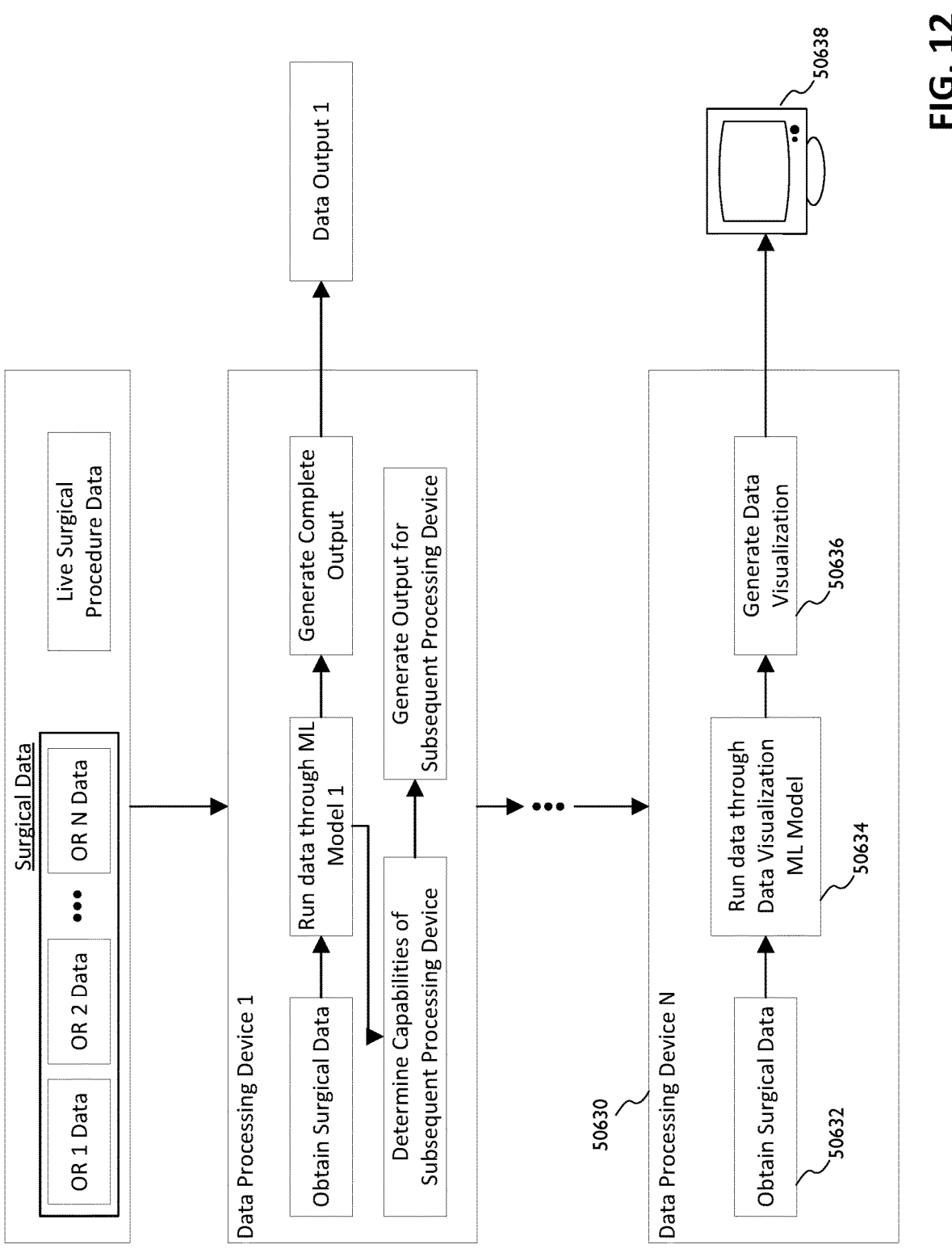
FIG. 12 illustrates an example flow of generating a data visualization using interrelated ML models.

FIG. 12 illustrates an example flow of generating a data visualization using interrelated ML models. Data processing devices may obtain surgical data and process the surgical data using ML models (e.g., as described herein). Outputs may be generated for subsequent data processing devices (e.g., as described herein). A data processing device may include a processing device using a ML model associated with generating a data visualization of input data. For example, surgical data may be input to a ML model to generate a graphic for a user that may indicate insights, trends, patterns, recommendations, etc. A data visualization of surgical data may be informative to HCPs, for example, performing a live surgical procedure.

As shown in FIG. 11, a data processing device N 50630 may include a processing device associated with data visualization. The data processing device N 50630 may obtain surgical data (e.g., as shown at 50632), for example, from previous ML models, surgical databases, and/or the like. The data processing device N 50630 may use an ML model to perform a data visualization processing task (e.g., as shown at 50634). For example, the ML model may be used to generate a graphic, chart, recommendation, etc. based on the obtained surgical data (e.g., as shown at 50636). The data visualization may be sent as an output to a user. For example, the data visualization may be sent to and displayed on a display (e.g., as shown at 50638). The display may be used, for example, in an operating room during a live surgical procedure by an HCP. The display may be used, for example, by an HCP in planning a surgical procedure.

The ML models (e.g., algorithms) may be used (e.g., within the same data processing device or within different data processing devices) to take on different portions of data reduction, data interaction, and/or data analysis. The outputs of the ML models may be fed as inputs to the other interrelated ML models (e.g., to be used for processing). The ML models may process data in different portions of a network ecosystem. For example, the network ecosystem may include data processing at a surgical hub level, an edge-network level, a cloud network level, etc. The outputs generated at the different levels of the network ecosystem may be fed to the different ML models present at varying levels of the network ecosystem. The outputs may pass conclusions, results, and/or supporting metadata to the other ML models. The outputs may be a portion of the complete dataset used in previous ML model processing. For example, multiple ML models may be processing data in different hub networks. The different hub ML models may feed their results to ML models in the edge-network and/or cloud network. The information feeding from one system to a subsequent system may be variable (e.g., dependent on the capacities of the receiving system). The information feeding from one system to a subsequent system may be variable, for example, based on the privacy level of the data and the receiving system's status within a protected HIPAA network. Multiple interrelated ML models (e.g., algorithms) may be used (e.g., in conjunction with each other) to identify different portions of data analysis (e.g., data preparation, identifying relationships in data, communicating recommendations, communicating adaptations of control programs, etc.)

In examples, the interrelated ML models may include nested ML models (e.g., algorithms) to process discrete and/or separate tasks for full processing of the data. Nested and/or hierarchical ML models may be used to prepared and process data (e.g., biomarker data).

For example, the interrelated ML models may include an ML model associated with pre-processing the data. The pre-processing ML model may be used to determine one or more of the following: integrity of the data, organizational state of the data, completeness of the data, and/or the like. The pre-processing ML model may be used to determine whether data is ready for data reduction.

For example, the pre-processing ML model may compare available datasets, for example, to look for differences in completeness, depth, annotation level, surgical task/aspects tagging, and/or the like. The identified differences may be compared with known (e.g., valid, preconfigured) interactions and/or relationships. The identified differences may be compared against a validation set of data. The identified differences may be compared against a suspected interrelationship listing. Portions of the data may be (e.g., may need to be) combined, linked, associated, etc., for example, to complete the dataset to be ready for further processing.

Datasets available for ML models may be incomplete based on policy implementations. For example, datasets available for ML models may be incomplete due to HIPAA limitations, consent issues, and/or limitations imposed on the collection of data from a surgery, patient, and/or devices. The incomplete dataset may create an issue for the ML model to use (e.g., ML models may not perform accurately on incomplete datasets). ML models may (e.g., need to) combined multiple (e.g., two or more) incomplete datasets into a complete set, for example, to perform an accurate analysis.

Preprocessing ML models may be assisted, for example, based on a directionality analysis (e.g., whether the trends generally are getting better or worse). For example, the directionality analysis may assist the pre-processing ML model to determine the weight of subjective assessments. The more iterations in combination with subject assessments may reduce the impact of subjectivity in base data that is analyzed. For outcomes, recovery, and/or treatment analysis, the processing may involve subjective appraisals (e.g., which may create a repeatable link between results from causes which are improper or questionable).

In examples, missing or combined datasets may be tagged (e.g., indicated as such), for example, to track the impact on results, outcomes recommendations, etc. For example, a post-processing check may be run (e.g., using an ML model) to ensure that no absent, marginal, or interwoven data affected (e.g., substantially affected) the results (e.g., as compared with the data set being removed instead of combined). A flag may be indicated, for example, if the tagged data did impact (e.g., substantially impact, impact beyond a threshold) a relationship, result, and/or trend based on the completeness of the data and/or the validity of the data. The flag may allow an end user to input (e.g., make a call) on the final results (e.g., the recommendations provided by the analysis generated by the ML model).

ML models may be used as a gatekeeper and/or a validity check on a fresh (e.g., new, non-training) data set. The ML model may be trained on training datasets to act as a validity check on input data. For example, the ML model may be used (e.g., depending on the confidence in the ML model) to take in input data, process the data (e.g., run a transform on the data), and determine a result based on the processing. The ML model may determine whether the result is within an acceptable level (e.g., threshold range) of deviation from data that is measured and/or recorded. The data going into the ML model may be trusted if the result is accurate. The validity check may be multiple layers deep (e.g., start with height and weight to predict basic metrics and then use complex metrics to determine complex outputs and/or medical classifications.

For example, a body mass index (BMI) may be determined for a patient. Data on co-morbidities and intensity of diabetes, blood sugar levels, and/or blood pressure may be used in conjunction with the medications the patient is taking, for example, top determine whether the combinations are within the expected and/or predicted bounds (e.g., including the current standard deviation associated with the ML model). The data may be treated as valid (e.g., ready) to be added to other data sets for reduction, for example, if the data is determined to be within the accuracy bounds. If the data is outside the accuracy bounds, the ML model may request or seek confirmations of the out of bounds (e.g., outlier) data. If the data is outside the accuracy bounds and an outside user confirms that the data is correct, the ML model may adjust the bounding check for future data sets (e.g., further training the ML model for better accuracy).

This may lead to the ML model resulting in tighter or looser constraints on the other datasets. In examples (e.g., associated with multiple levels of validity checks using the ML model), a BMI may be checked first, a heart rate and health blook pressure may be checked second, the trending of biomarkers with respect to weight gain or loss may be checked third, and/or the like. The different levels (e.g., each of the different levels) may confirm conformance to the pre-established trends or ranges (e.g., trained trends or ranges), and the data may be used to adjust the ranges and calculate future relationships and/or patterns (e.g., train the ML model to be more accurate for future data analyses).

For example, base medical measurements may be input to a ML model (e.g., height, weight, demographics, gender, previous conditions, etc.) A first (e.g., basic) processing layer may be used to link the data with more complex conditions and/or outcomes. If an ML model takes in certain input data for an analysis but a portion of the input data is missing (e.g., incomplete), the input data may be run through a different ML model to produce a complete (e.g., synthesized) dataset to be run through the complex ML model. For example, the incomplete dataset may be completed. Protocols may be set in place that may allow for the completed data to be input to the complex ML model if the completed dataset (e.g., synthesized data) is trustworthy The pre-processing ML model may be used to identify incorrect and/or erroneous data, for example, by parsing available data into sub-groups that are run through a similar ML model to determine if the data is correct and/or good data.

Grouping data sets may enable a ML model to determine whether datasets contain incorrect and/or erroneous data. In examples, available data may be parsed into multiple (e.g., three) groups based on a predefined order (e.g., all even, all odd, etc.) The groups (e.g., each group) may be processed using an ML model (e.g., the same ML model). If the results are similar between the datasets, the datasets may be determined to be good (e.g., accurate, complete, etc.). For example, if results from two of the three groupings produce similar results and results from the third grouping is not similar, the third grouping may be flagged (e.g., indicated as irregular). The irregular dataset may be dissected and/or decomposed, for example, to identify the datapoints that may cause the irregular output. The datapoints determined to cause the irregular output may be flagged to the user to confirm the accuracy. The irregular data point may be confirmed, for example, by re-choosing the three data set sub-groups and re-running the ML model (e.g., calculations/analysis) to confirm that the irregular data point is the cause of the irregular result and/or conclusion.

In examples, if two sources of the same and/or related biomarkers do not provide the same result for the same patient, a separate sub-algorithm (e.g., different ML model) may be used to perform comparison and pattern identifications in related data, for example, to distinguish which of the conflicting data sets is more correct (e.g., the dataset closer to the verified set is determined to be more correct). The sub-algorithm may be enabled to return the result and/or identified pattern to a higher layer of processing (e.g., which may resolve the conflicting datapoints issue). The problematic datapoint may be discarded. Discarding a reading may be considered, for example, based on an input from an HCP. HCPs may look at the entirety of a dataset and determine that a problematic datapoint does not fit or does not have a rational explanation. The problematic datapoint may be overridden but still allow for the collection of the semi-erroneous data. For example, HCPs may determine that datapoints are irregular but there are enough regular datapoints to continue. For example, an anesthesiologist may determine that a surgical procedure is in a critical step and the data is needed to perform the step. The anesthesiologist may determine that there are sufficient accurate datapoints to make logical conclusions (e.g., based on knowledge, intuition, other data) in order to continue the procedure in a safe manner.

For example, the interrelated ML models may include an ML model associated with performing data reduction. The data reduction ML model may operate on surgical procedure data (e.g., completed, master, ready surgical procedure data). The data reduction ML model may perform a reduction methodology (e.g., as described herein) to identify trends, generate relationships, identify patterns, create recommendations, and/or the like.

The data reduction ML model may use a history of past datapoints (e.g., that map historic inputs to history outputs), for example to determine an unknown output given a complex input. During a training phase of the ML model, the model may generate relationships between inputs and outputs. The ML model may be used to predict outputs based on the complex input and previous training on mapped data. Trends, recommendations, conclusions, and/or relationships may be determined based on the training dataset. The trained ML model may, for example, take an unknown image as an input, and determine a classification associated with the unknown image with a certain degree of confidence (e.g., based on historic data that trained the ML model). The model may not identify trends not identified in the training dataset (e.g., new trends). The model may focus on mapped trends based on the training.

For example, the interrelated ML models may include an ML model associated with data display and/or visualization. The data display ML model may combine the recommendations, conclusions, trends, relationships, and/or other results it has determined, for example, in combination with a decomposed manifestation (e.g., visualization) of the data. The visualization of the data may be presented to a user, for example, so the user can see the recommendation and at least some supporting metadata supporting the determined trends and/or conclusions.

Data visualization may be used to learn about the available data and identify main patterns in the data. Data visualizations may be represented by one or more of the following: a parallel coordinates plot, a prediction table, a hierarchical segmented plotting of decision tree results, decision boundaries, and/or the like.

For example, data visualization ML models may include using a parallel coordinates plot. The parallel coordinates plot may enable a user to compare different variables (e.g., features) together to discover possible relationships. For example, in the scenario of hyperparameters optimization, a parallel coordinates plot may be used to inspect what combination of parameters may give the greatest test accuracy. For example, parallel coordinates plots may be used in data analysis to inspect relationships in values between the different features in a data frame.

For example, data visualization ML models may include using a prediction table. Prediction tables may be used for time-series data. Prediction tables may be used to identify on which datapoints (e.g., in time-series data) the ML model may be underperforming. The prediction tables may be used to identify the limitations the ML model may be facing. Creating a prediction table may include creating a summary table that includes actual and predicted values and a form of metrics summarizing how well and/or bad a data point has been predicted.

For example, data visualization ML models may include using hierarchical segmented plotting of decision tree results. Linked bar charts and/or pie graphs may be used, for example, based on the level of the decision tree. The visualization may illustrate overall trends (e.g., plotted trends) identified by the ML model.

Figure 13:
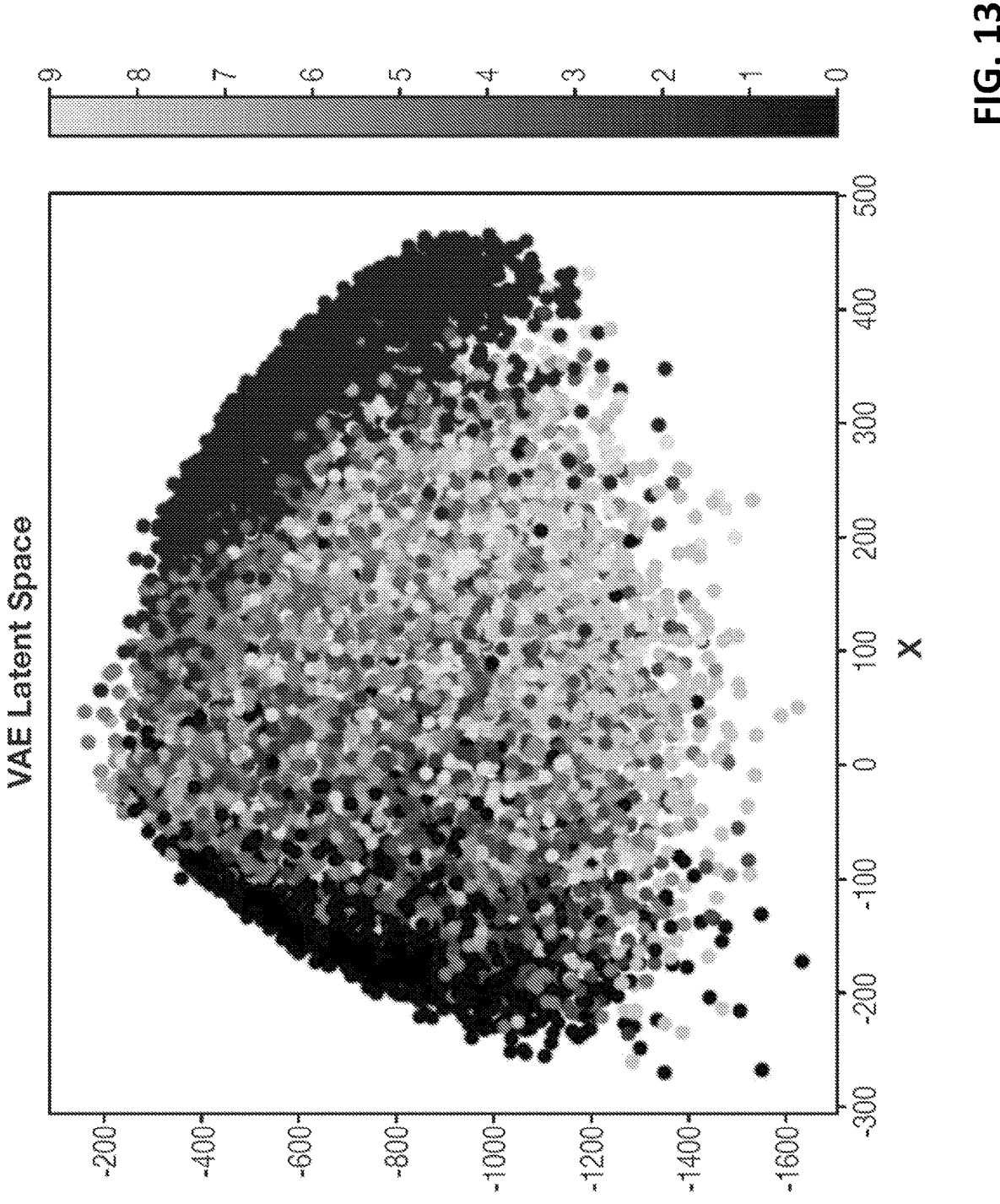
FIG. 13 illustrates an example plot point graph for VAE latent space.
Figure 14:
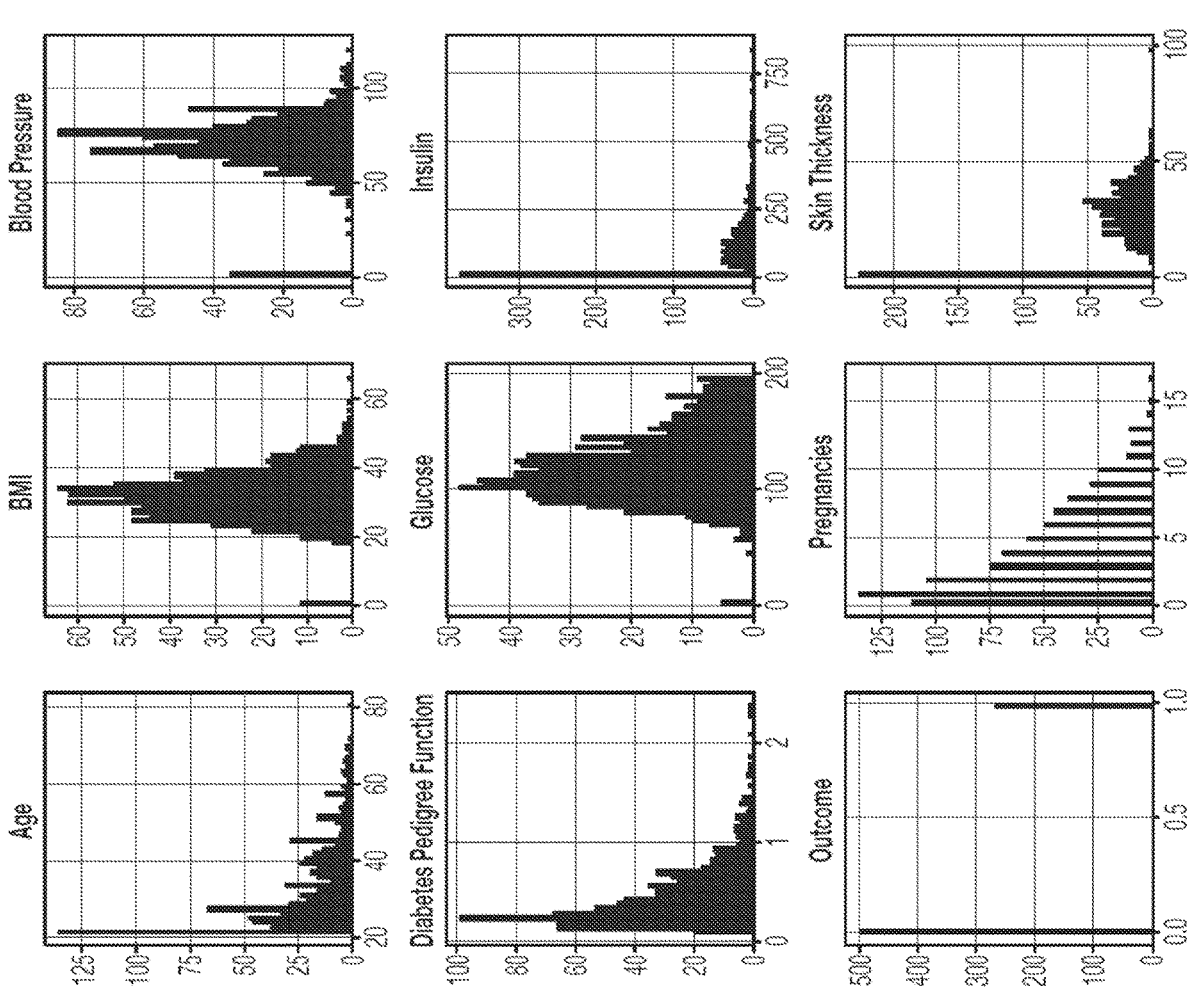
FIG. 14 illustrates an example of implementing decision boundaries for the VAE latent space data plot.

For example, data visualization ML models may include using decision boundaries. Decision boundaries may enable graphical understanding on how a ML makes its predictions. Decision boundaries associated with the ML model process may be plotted. FIG. 13 illustrates an example plot point graph for VAE latent space. FIG. 14 illustrates an example of implementing decision boundaries for the VAE latent space data plot. As shown in FIG. 14, comparative trending used with decision boundaries on key variables may be used to identify relationships within the data.

Data visualization performed by ML models may enable trend identification that may not be captured by human analysis, for example, based on the multidimensional optimization performed by the ML models.

For example, the interrelated ML models may include an ML model associated with performance. For example, after a conclusion and/or recommendation is determined (e.g., agreed on) and permitted to adjust the behavior of an attached system, a ML model may collect on-the-fly datasets that may enable small additional customizations within the predefined threshold range defined by the data reduction recommendation.

For example, the interrelated ML models may include an ML model associated with determining whether data should be substituted. For example, the ML model may determine data boundaries that may be used to determine whether data should be substituted. For example, an ML model may determine if a baseline (e.g., standard) control algorithm (e.g., parameter) should be substituted with a different (e.g., irregular) control algorithm (e.g., parameter). The ML model may determine that the different (e.g., irregular) control algorithm may enable a surgical instrument to operate in a manner adapting to the surgical procedure. The ML model may determine to use a different control algorithm, for example, based on a different biomarker of a functional instrument measurement. The ML model may determine errant data sets relative to the ML boundary (e.g., as a separate process/computation), for example, to enable the ML model to determine if a baseline control algorithm should be substituted for a different control algorithm.

For example, a low impendence measure on a bipolar radio frequency device may indicate one or more conditions (e.g., low impendence tissue, immersion in a conductive fluid, a physical short in the electrical path, and/or the like). The ML model may receive (e.g., compile) weld capacity data associated with the tissue and biomarker data (e.g., link the data together), for example, to determine different control parameters (e.g., different temperature and/or power level control of a generator) that may enable a better surgical step (e.g., better welds performed based on different temperature and/or power level control of the generator). The ML model may determine that a zone of the dataset (e.g., low impendence) does not fit within the pattern and/or groupings. The ML model may process the irregular zone in a different (e.g., separate, independent) process with a direction (e.g., goal) to find a different control means and/or pattern (e.g., to run the instrument when in the irregular zone). The ML model separately processing the irregular zone may enable adaptively changing control parameters for surgical instruments and/or equipment being used in a surgical procedure. The different control parameters may be used for the irregular zone (e.g., only).

For example, the interrelated ML models may include a secondary ML model to oversee a primary real-time ML operation. For example, the nested ML algorithms may be statically sequential and/or have a real-time component (e.g., aspect). A command structure may be implemented, for example, to control interactions between a number of ML algorithms (e.g., independently processing ML algorithms) reporting on status for systems and/or ML processes performed (e.g., data validity, model selection, result verification, etc.). The primary command algorithm may use the summarized data and determined command decisions. The primary command algorithm may request status data from a system (e.g., any system) to use the data for a decision. Other ML systems may interrupt the primary algorithm with data, for example, if the system meets a condition (e.g., reaches a ready status, disabled status, etc.).

Multiple ML models (e.g., algorithms) may be combined, for example, to be used in concert. ML models used in concern may achieve a better, faster, or more accurate result (e.g., pattern), for example, as compared with separate, independent ML models. ML models may back stacked. Stacking models may improve performance metrics for large models. Stacking ML models may benefit from obtaining known relationships between outputs that can already be computed (e.g., adding additional speed and reliability to the model).

For example, stacked ML models may be used in parallel (e.g., parallel utilization of stacked ML algorithms). Stacking models may enable training using the same training dataset with multiple types of modeling techniques. The predictions of the different models may be used as input features for a meta-classifier. The meta-classifier may minimize the weaknesses and maximize the strengths of the individual models. Different types of models may have different strengths associated with their predictive capacity. Stacking multiple models on a single dataset and using a meta-classifier on the outputs may enable parallel utilization of stacked models. The result may be more robust, for example, as compared to if the model was run multiple times and/or was more complex. Utilization of a stacked model may enable better predictions and/or faster predictions, for example, compared to standard computations. The stacked ML models may boost (e.g., convert) weak learners to strong learners faster than other techniques. Ensembled learning may enable the combining of several learners for improved efficiency and accuracy.

For example, stacked ML models may be used in series (e.g., serial utilization of stacked ML algorithms). Serial use of models may include feeding results from a first ML model into a second ML model, for example, to compartmentalize the stages of an analysis. Serial use of models may be useful, for example, if the stages produce meaningful trends the user may use as insight. Serial use of models may be useful, for example, if there are checks along the stages to ensure that errors are more propagated within the several layers into the algorithm (e.g., in case the data is unbalanced or flawed). Serial use of models may allow separation of overall processing resources, for example, such that multiple systems, locations, and/or separate networks may be used (e.g., to determine the overall trending/pattern identification), as shown in FIG. 10. Separation of processing resources may be used, for example, if a primary system has insufficient physical resource and/or time to achieve the processing goals.

For example, serial utilization of stacked ML algorithms may include training the ML models on the same set of training data. The ML algorithms may include using a layer (e.g., additional layer) of a meta-classifier that takes in predicted values of the model and processes the predicted results, for example, to reduce error and strengthen the best outcomes from the different modeling techniques. The data may be fed through the same level ML models separately with the outputs compared and adjusted by a meta-classifier.

Serial utilization of stacked ML algorithms may include using different parts of different models at different stages of an analysis (e.g., a layer of a first model that is taking in data to predict a second layer, where there may be a device that directly measures the result associated with the second layer). Collected data may be used to override part of the first layer of the ML algorithm (e.g., saving resources and/or reducing drift in the final layer of the model). Collected data may be used to compare with the predicted results (e.g., to check prediction quality and the quality of the data being measured, for example, whether the instrument is malfunctioning due to the model predicting an output that is different than expected). Systematic errors may be detected (e.g., errors in collection and/or recordation) based on the predicted results. The systematic errors may be corrected (e.g., using the instruments differently).

Figure 15:
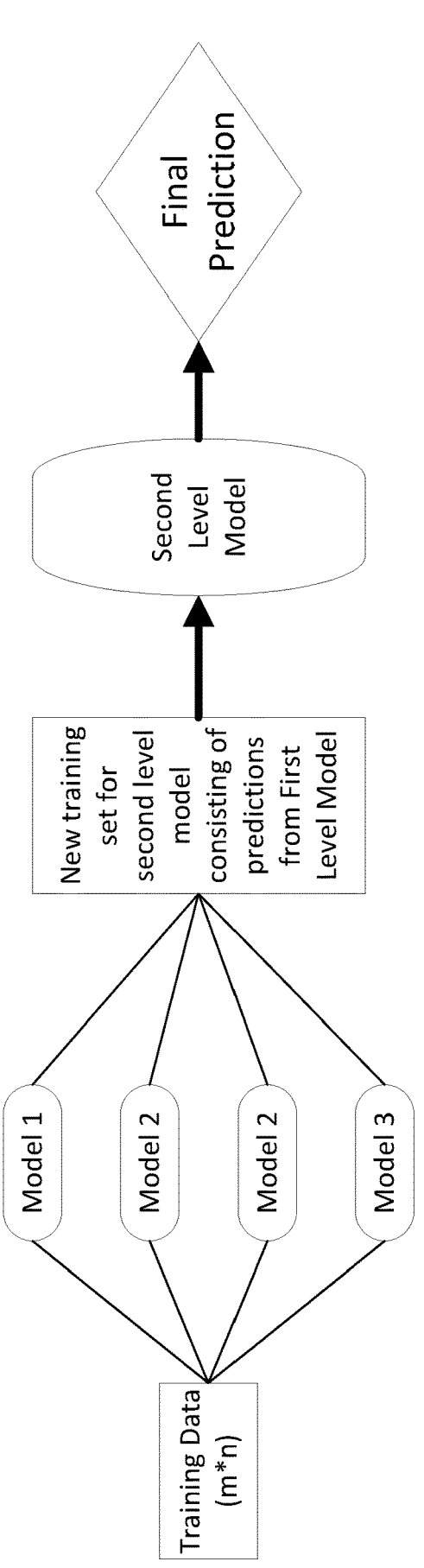
FIG. 15 illustrates an example of using ML models in series and parallel.

A combination of serial utilization and parallel utilization of stacked ML algorithms may be used. FIG. 15 illustrates an example of using ML models in series and parallel.

Incomplete and/or inconsistent data may be adapted to be used by ML models, for example, by using related but independent available data. Datasets may be flawed (e.g., partially flawed). Data preparation may include processing data to be more suitable for ML. Data preparation may include establishing a data collection process. The ability to resolve incomplete data sets may enable better use and more reliable computation using ML models. For example, incomplete and/or inconsistent data may be prepared to be better suited for ML processing using one or more of the following techniques: data consolidation, leveling data quality, data consistency, and/or the like.

Data consolidation may be used, for example, to make data more suitable for ML models. Data consolidation may use data warehouses and an extract, transform, and load (ETL) process. For example, data may be deposited in warehouses (e.g., storages). The storages may be created for structured records (e.g., SQL). The records may be suitable for standard table formats. Warehouses may load (e.g., store) data after transforming the data (e.g., to a more usable format).

Data consolidation may use data lakes and an extract, load, and transform (ELT) process. Data lakes may be a storage capable of keeping structured and unstructured data (e.g., images, videos, sounds, records, PRDF files, etc.). Data may not be transformed before storing, for example, if it is structured. Data may be stored as is, and the determination on how to use and process the data may be performed later (e.g., on demand). Data lakes may be used for ML (e.g., better fit as compared to data warehouses).

Leveling data quality may be performed, for example, to make data more suitable for ML models. Leveling data quality may include dealing with omitted data. For example, omitting data may be associated with record sampling. Removing dataset records (e.g., objects) that contain missing, erroneous, and/or representative values may level data quality. Record sampling may be performed to form datasets that may be reduced (e.g., to identify key variables of data that need to be present to make a set more representative). For example, a system may determine to refrain from discarding data that has omitted data in categories and/or portions of the data that are not influential in the determination of trends and/or results (e.g., missing data would not affect overall processing task). Algorithmic templates may be created using base datasets, for example, to evaluate a final value. Adding amounts of data that are properly mapped (e.g., accurate) may allow for evaluation of a trained ML model to see if the prediction (e.g., output) is correct.

Leveling data quality may include aggregating datasets. For example, a pool of data may be combined for records (e.g., objects) pulling averages, means, random entries, and/or the like, to create datasets that represents a composite of the dataset. Aggregating may enable determining an average patients and/or randomized patients that may be representative of a broader dataset (e.g., but reflect complete records of the larger dataset). A dataset may be used (e.g., or another aspect of the data that is related to the missing data) to fill in (e.g., synthesize) the missing data, for example, which may enable inclusion of the incomplete dataset in an analysis while avoiding driving the calculation off the average (e.g., as a result of the missing data). For example, missing values may be substituted with dummy values (e.g., N/A for categorical values, 0 for numerical values). Missing numerical values may be substituted with mean figured. Categorical values may be substituted with the most frequent items.

Leveling data quality may include joining transactional and/or attribute data. Transaction data may include events that snapshot moments (e.g., the price of boots at a given time, when a user with a certain IP clicking on the "Buy Now" button). Attribute data may be static (e.g., more static). For example, attribute data may include user demographics and/or age. Attribute data may not relate to specific events. Data sources and/or logs may include both transaction and attribute data. Attribute data and transaction data may enhance each other, for example, to provide more predictive power (e.g., compared to using the data types separately). For example, if machinery sensor readings are being tracked to enable predictive maintenance, logs of transactional data may be generated. Qualities (e.g., attributes) may be added, for example, such as equipment model, batch, location, etc. Dependencies between the transaction data and the attribute data may be analyzed to determine dependencies (e.g., between equipment behavior and its attributes. Transaction data may be aggregated into attributes.

Leveling data quality may include use of clinical scoring systems to complete missing data. For example, pre-existing operative scoring systems may be used to align missing aspects. For example, mortality statistics may be used as a means to link outcomes with procedure steps (e.g., order, difficult, etc.) to complete missing nominal monitored statistics. For example, an APHAR risk score may be used by HCPs to estimate post-operative outcomes as a means for using the combined output of the lower fidelity clinical model as a means to determine a missing piece of data the higher fidelity ML model uses to make a prediction. For example, bariatric suitability pre-operational scoring may be used to complete data sets.

In examples, using one combined measure in combination to another combined measure to fill in missing aspects of either or another combined biometric aspect may be performed. For example, a patient's APGAR and prolonged air leak risk scoring may be used to determine secondary uncollected data that in turn could be used by the machine learning to identify potential post-operative infection risk.

Clinical scoring systems may be limited by subjective limitations. For example, clinical scoring systems may employ subjective rating scales (e.g., patient's pain level may differ between patients). Subjective rating scales may be difficult to evaluate.

Leveling data quality may include fixing imbalanced data, for example, by rescaling the data. Data rescaling may include data normalization. Data rescaling may improve the quality of a dataset by reducing dimensions and/or avoiding situations where some values overweight other values. Min-max normalization may be used. Min-max normalization may include transforming numerical values to ranges (e.g., from 0.0 to 1.0 where 0.0 represents a minimal value and 1.0 represents a maximum value), for example, that may even out the weight of an attribute compared to other attributes in the dataset. Decimal scaling may be used to perform data rescaling. Decimal scaling may include moving decimal points in a direction to rescale the data.

ML processes may be used to ensure that the data is within a threshold amount of rescaling, for example, before further analysis. Data may be entered incorrectly (e.g., decimal point may be omitted). An ML process may detect that the incorrectly entered data is beyond a reasonable range and should be flagged for further analysis and/or review.

Leveling data quality may include fixing inadequate data, for example, using synthetic data. Synthetic data may include artificially generated samples that mimic real-world data. Synthetic data may induce bias in data. The impact of synthetic data may be limited and/or determined, for example, to minimize inadvertent data shifting due top the use and/or inclusion of the synthetic data. ML models may experience drift in predicting outputs for base datasets with the inclusion of synthetic data. The output of the ML model synthesizing data may be input to another ML model, for example, to ensure the synthetic data is not producing inappropriate results.

Leveling data quality may include fixing inconsistent medical term interchangeability. For example, a natural language filter may be used. A natural language filter may be used on medical implication terms within a dataset. The search may adjust variants and semi-interchangeable medical terms into a consistent descriptive result.

For example, a system may use an ML process to determine terms that are effectively interchangeable within the medical literature and/or billing codes. The pattern or trend may group and/or cluster the terms that are close to the same meaning. The ML process may use a boundary algorithm to device terms that may be grouped into one group and other in another near group. The listing may be used to adjust the language within the medical records to a constant terminology set. The system may run a verification on the synonym aggregation, for example, by looking at outliers along the boundary within a known teaching dataset. The adjustments may allow the system to enlarge, combine, and/or separate boundaries to better represent the information to a common language.

Natural language processing (NLP) may be used, for example, as a second ML process layer for performing classification for models. The NLP models may use information (e.g., additional information), for example, such as the background of the author, local terms, phrases, region specific words. Pairing data about the users with how the data was gathered and the history of the data may enable creating an ML model that classifies the author as a certain thing and then use the classification to further influence the sentiment analysis. Language trends may be determined, for example, using NLP models.

Sentiment analysis may be used, for example, to evaluate sentiments associated with wordings. For example, a sentiment analysis may be used to determine the happiness of populations based on the wordings of messages. Sentiment analysis may be paired with geotracking to model how happy a population is.

Leveling data quality may include ensuring data consistency. For example, data formatting may be used to ensure data consistency. Data formatting may include date formats, money denominations and symbols, numeric range settings, and/or the like. Discretizing data may be used to ensure data consistence. Predictions may be more effective, for example, based on turning numerical values into categorical values. Turning numerical values into categorical values may be performed by dividing the range of values into a number of groups.

Data structure may be used to compensate for data incompleteness. For example, consistency of a classification of learned instances may be improved and/or ensured, for example, to ensure conclusions are trustworthy and/or reliable. In examples, the measure of subjectivity may be used to report probabilities of results to be accurate and/or predictive. Individual comparison of user measured subjectivity may be used as a check and/or probability of the result of an ML process. Determination of a drift of a measurement may be used to identify uncontrolled measurements of biomarkers. For example, a drift measurement may be used to identify a potential cause of an inconsistent result. The HCPs may then identify how to modify control parameters and/or instrument configuration (e.g., to prevent the inconsistent result).

Using the structure of the data (e.g., procedure plan of the steps, the instrument usage, the HCP stress level, imaging results, combining images, and/or the like) may be used to compensate for lack of data completeness. Context of the surgical procedure, patient, and/or surgical step may be used to assist an ML model in determining a floating boundary for groupings. For example, different (e.g., ten different) liver resection procedures may be recorded using a monitored scope. The system may be aware that the data is associated with liver resection jobs. The system may determine that the instruments are being used at the liver at predefined steps of the procedure. The steps may be used to identify the liver (e.g., color, shape, location, etc.), for example, which may enable ML processes to define an accurate range of acceptable elements and/or aspects.

Systems, methods, and instrumentalities are disclosed for aggregating and/or apportioning available surgical data into a more usable dataset for machine learning (ML) model (e.g., algorithm) interaction. A ML model may be more accurate and/or reliable if using complete and/or regular data. Aggregating and/or apportioning available surgical data may enable a more complete and/or regular dataset for ML model analysis.

For example, a computing system may include a processor that may be configured to aggregate and/or apportion available surgical data into a more usable dataset for ML model analysis. The computing system may obtain a first set of surgical data associated with a surgical procedure (e.g., performed or live surgical procedure). The computing system may obtain a master set of surgical data (e.g., from a surgical database). The master set of surgical data may include a verified set of data. The master set of surgical data may be associated with historic surgical procedures. The computing system may determine that the first set of surgical data is problematic (e.g., incomplete, erroneous, irregular, etc.) The computing system may determine the first set of surgical data is problematic, for example, based on comparison to the master set of data. The computing system may generate substitute data. The substitute data may be generated based on the master set of data and the first set of data. The substitute data may be generated based on a data type that is problematic in the first set of data. The computing system may generate a second dataset (e.g., revised first set of surgical data), for example, that includes the substitute data and a portion of the first set of data (e.g., the non-problematic portion of the first set of data).

Data may be apportioned and/or aggregated, for example, to combine and/or verify incomplete datasets. Apportionment of surgical data may optimize usage of the data for comprehensiveness, accuracy, and/or verification of ML models. The combination, substitution, and/or integration of different datasets from different procedures, devices, and/or sources into a combined master set of data may be performed to enable analysis (e.g., using an ML model) to determine relationships, control program adaptations, recommendations of functional changes in surgical behavior, and/or the like. For example, a first incomplete dataset and a second incomplete data set may have related outcomes and/or procedure constraints that may be combined to generate a more complete dataset for an ML model to interpret. Segmented datasets from differing sources may be used in combination with a separate verification data set, for example, to ensure adequate combination of the datasets to draw conclusions from. Data within a portion of a protected dataset (e.g., HIPAA controlled) may be combined with a different portion of a different dataset, for example, without either dataset contributing too much identifier data that may trigger privacy controls.

ML models (e.g., algorithms) may produce more accurate and/or relatable results, for example, using a complete and accurate data set (e.g., data set with consistent data, data set without missing data, etc.). ML models may be used to ensure that a dataset for processing (e.g., using subsequent ML model(s)) may be complete and/or adequate (e.g., able to provide reliable conclusions). The ML model may (e.g., based on a determination that a dataset is incomplete or contains inaccurate data) revise the dataset (e.g., complete the dataset and/or remove outlier data) to be better suited for ML model processing.

Figure 16:
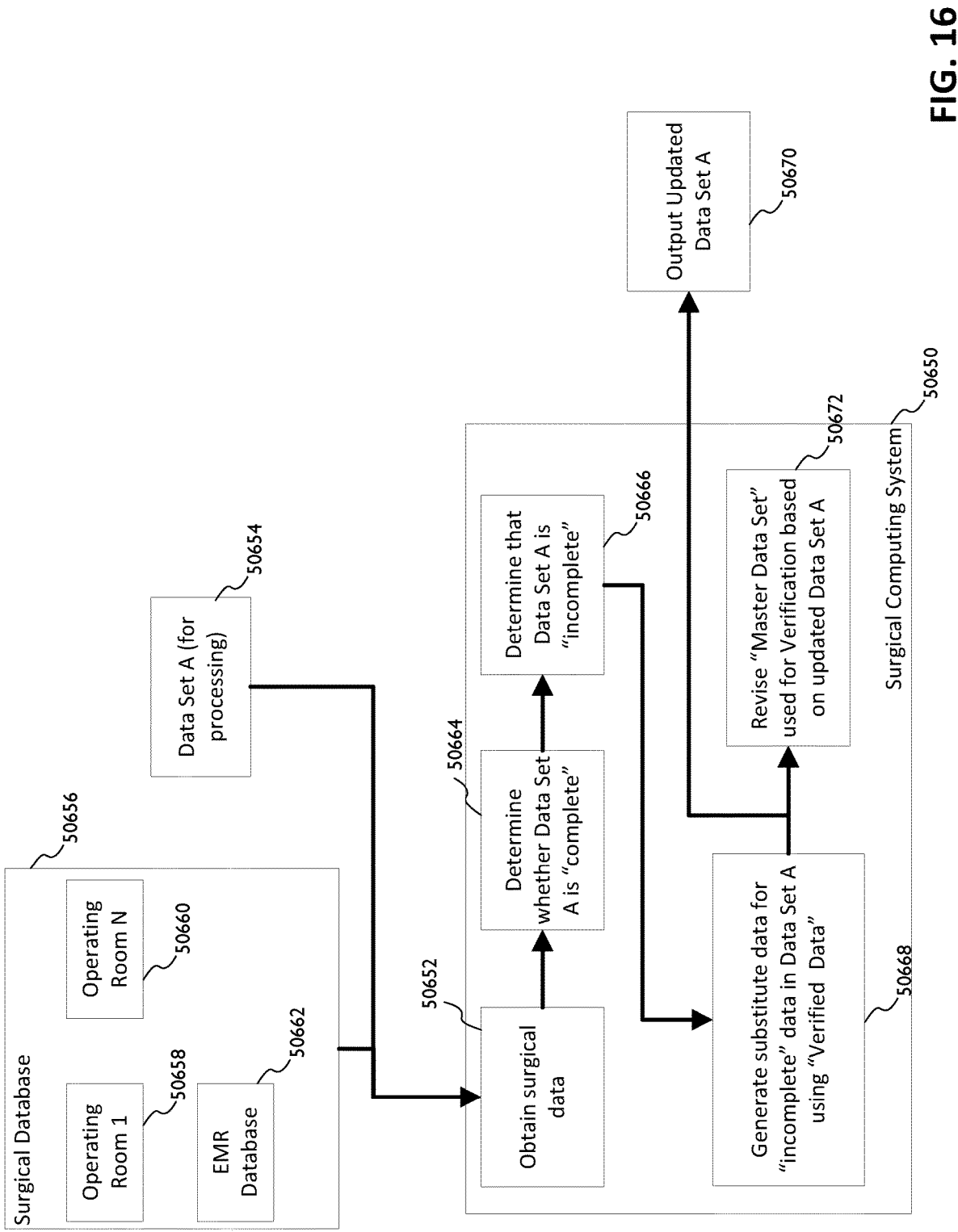
FIG. 16 illustrates an example of revising an incomplete dataset and updating a master data set for verification.

FIG. 16 illustrates an example of revising an incomplete dataset and updating a master data set for verification. As shown in FIG. 16, a surgical computing system 50650 may obtain surgical data (e.g., as shown at 50652). The surgical data may include a data set (e.g., Data Set A) for processing 50654 and/or data from a surgical database 50656. Data from a surgical database 50656 may include data associated with an operating room (e.g., operating room 1 50658, operating room N 50660, etc.), an electronic medical records database 50662, and/or the like. The surgical data from the surgical database may include data from historic surgical procedures and/or processes. The surgical computing system 50650 may determine (e.g., as shown at 50664) whether Data Set A 50654 is a complete dataset (e.g., whether the dataset is missing data, whether the dataset contains irregular data, etc.). As shown at 50666, the surgical computing system 50650 may determine that Data Set A 50654 is incomplete. The surgical computing system 50650 may rectify the incomplete dataset (e.g., using an ML model). For example (e.g., as shown at 50668), the surgical computing system 50650 may generate substitute data (e.g., using an ML model) to insert into the incomplete Data Set A (e.g., to complete the dataset). The substitute data may be generated using verified data (e.g., confirmed data, accurate data from previous confirmation), for example, from the surgical data base or ML model storage. The surgical computing system 50650 may output the updated (e.g., completed) Data Set A (e.g., as shown at 50670). Additionally, the surgical computing system 50650 may revise a master data set (e.g., data set that is used for training the ML model, data set from the surgical database, verified dataset, and/or the like), for example, based on the updated Data Set A. The updating of the master data set may enable the ML model to constantly improve its accuracy in its predictions.

For example, the surgical computing system may obtain a first set of surgical data associated with a first surgical procedure. The first set of surgical data may include data from surgical instruments, surgical equipment, patient data, HCP data, and/or the like. The first surgical procedure may be a live surgical procedure. The first set of surgical data may include incomplete data. For example, data collection at a surgical instrument may be inaccurate. The first set of surgical data may be missing data for certain portions of a surgical procedure, for example. The missing surgical data and/or erroneous surgical data may cause issues in an analysis performed using an ML model.

The surgical computing system may determine that the first set of surgical data is incomplete. The surgical computing system may determine that the first set of surgical data is incomplete using an ML model. The ML model may determine that there is missing data and/or erroneous data. The ML model may determine that there is missing data and/or erroneous data based on comparison to historic surgical data (e.g., data from a surgical database) The ML model may determine that there is missing data, for example, if there are gaps in the dataset.

The ML model may determine there is erroneous data if the dataset includes data inconsistent with the rest of the dataset. For example, the ML model may determine a heartrate measurement is inconsistent with the rest of the data based on the heartrate at a first time spiking to a level that is not within an average deviation of the time points surrounding the data point. For example, the ML model may determine that a heartrate measurement is erroneous, for example, based on the measurement exceeding normal human values.

The ML model may determine there is erroneous data if the dataset includes data inconsistent with historic surgical data (e.g., data from the surgical database). For example, a ML model may determine a landmark position in a patient's body is erroneous based on comparison to landmark positions in other patients from similar surgical procedures where the patients are similarly situated.

The ML model may determine the dataset is incomplete and/or erroneous, for example, based on comparison to a master data set (e.g., verified dataset). A verified dataset may include data that is confirmed as accurate data. The verified dataset may include a training dataset for a ML model. The ML model may determine the dataset is incomplete and/or erroneous, for example, if it contains data that is inconsistent with the master data set.

The completeness of a dataset may be determined, for example, based on a pre-processing ML model (e.g., algorithm). The pre-processing ML model may examine data looking for incomplete, irregular, and/or erroneous data.

In examples, a data reduction ML model may determine conclusions that may not be validated (e.g., conclusions are not reliable) based on comparison to a validation dataset.

The data reduction ML model may determine that the ML model is unable to identify stable conclusions on a dataset. Based on a determination that the conclusions may not be reliable, the input data may be input to a pre-processing ML model, for example, to determine the integrity of the data. The pre-processing model may look for trends within the data, for example, that may imply errors, omissions, and/or mis-classifications. The pre-processing model may determine recommendations based on identified issues with the data.

The pre-processing ML model may obtain data characterized as irregular, unstable, and/or errant. The ML model may discover issues with the data, for example, such as calibration errors with surgical instruments, failure of sensors, and/or data recordation issues.

The pre-processing ML model may determine that a dataset is problematic (e.g., incomplete, irregular, erroneous, etc.), for example, based on the sampling rate. For example, a sampling rate (e.g., Nyquist sampling rate) may affect data collection. Data may be irregular and/or incomplete based on the sampling frequency.

For example, a data reduction ML model may be used to analyze data associated with force-to fire, outcomes, complications, a procedure plan, complaints, force-to-close, visible staple form, bleeding, and/or the like. The ML model may determine (e.g., while performing data reduction on the data) that the ML model is unable to reach a conclusion that can be verified (e.g., based on a validation dataset) and/or the ML model cannot identify reliable and/or repeatable relationships. The data reduction model may pass the data to a pre-processing ML model to verify the integrity of the data. The pre-processing ML model may identify that there are irregularities in the dataset. The pre-processing ML model may identify issues with the data. For example, the pre-processing ML model may check for completeness, comprehensiveness, and/or erroneousness. The pre-processing ML model may identify a product inquiry classification of the failure was incorrect. The pre-processing ML model may recommend re-classification of a number of the mis-classified failures. The recommendations may be confirmed, for example, by HCPs and/or an independent system. The fixed data may be returned for data reduction trending.

The pre-processing ML model may determine the amount of drift that occurs in the data that is fed into the system. For example, the pre-processing ML model may determine that irregularities are in the data due to a detected drift. For example, if a 9V battery is actually measured as 8.7V and a 60 mm measurement is actually 59 mm, and the operating temperature is actually 60 degrees as opposed to the assumed 58 degrees, etc, then the drift may be determined to account for data irregularity. For example, the drift may be tagged in the data for consideration during data reduction.

The pre-processing ML model may identify data that is damaged and/or incomplete as a result from issues with communication models (e.g., algorithms), reduction models (e.g., algorithms), wireless buffer sizes in communication devices (e.g., if someone has a high frequency sensor polling faster than Bluetooth low energy buffer can dump data to a processor, then bits may be lost, overwritten, and/or messed up), and/or the like. The pre-processing ML model may identify the error and determine the occurrence and frequency of the error to track a pattern to identify potential causes. The identified patterns may be used to send a notification about the error and/or may resolve the issue.

The ML model (e.g., a subsequent ML model) may improve and/or rectify the incomplete and/or erroneous data set. For example, the ML model may generate substitute data (e.g., synthesize data, for example, as described herein) for the incomplete and/or erroneous dataset. The ML model may generate substitute data, for example, based on the non-incomplete and/or non-erroneous portions of data in the dataset. The ML model may generate substitute data, for example, based on the master set of data (e.g., data from a surgical database).

Additional data may be incorporated into a data set, for example, to complete a dataset for ML processing. For example, incorporation of instrumentation having incomplete and/or a limited subset of its functional operation (e.g., based on the instrumentation of the device and/or the motorization of the device) may result in a portion (e.g., only a portion) of the overall data being collected.

An ML model may be used to determine available data and the circumstances under which the data was collected. The ML model may be enabled to aggregate datasets, for example, that have missing data aspects. In examples, ML models may encounter scenarios where the models do not perform as expected (e.g., edge cases). An edge case may be a problem and/or situation that occurs (e.g., only) at a certain operating parameter (e.g., minimum or maximum operating parameter). An edge case may involve input values that may use special handling in an ML model. Unit tests may be created, for example, to validate the behavior of ML models in edge cases. The unit tests may test the boundary conditions of an algorithm, function, and/or method. A series of edge cases around a boundary may be used to give reasonable coverage and confidence (e.g., using an assumption that if it behaves correctly at the edges, it should behave correctly everywhere else).

Edge cases may occur, for example, based on a bias, variance, unpredictability, and/or the like. A bias may be associated with the ML model being simple (e.g., too simple). Bias may occur, for example, if an ML model cannot achieve good performance on a training data set. Bias may indicate that the architecture of an ML model does not have a structure that can represent nuances in training data.

Variance may occur, for example, if the ML model is inexperienced (e.g., too inexperienced). If an ML model achieves good performance on its training data but performs poorly in testing, the training data set may be too small to adequately reflect the range of variability in a ML model's operational environment.

Unpredictability may occur, for example, if the ML model operates in an environment experiencing variability and/or surprises. ML may rely on finding regular patterns in input data. A statistical variation may exist in data, but a ML model with an appropriate architecture and trained using enough training data may be able to find enough data regularity (e.g., achieve small enough bias and variance), for example, to make reliable decisions and minimizer edge cases.

A system may run multiple models (e.g., ML models) on differing portions of an incomplete dataset, for example, to determine which parameters have and do not have impacts (e.g., significant impacts) on outcomes. The ML models may run metadata related to the portions of the data that are impactful but missing portions of the data, for example, to determine if there is metadata around the data collection that may help fill in the data (e.g., intelligent substitution or averaging) or determine trends that may be used in substitution to the primary missing data.

For example, bleeding events may have a direct relationship to blood pressure of a patient. Blood pressure may not be tracked in real-time within the operating room during a surgical procedure. An electrocardiogram (EKG) version of heart rate monitoring may be used, for example, as a proxy for portions of the dataset that is missing blood pressure measurements with a nominal heart rate being set to a nominal blood pressure. The evaluation of an advanced energy device may be compared with bleeding results and using the blood pressure of the patient event, for example, if some of the patients did not have active blood pressure monitoring at the time of the surgery and imaging of the surgical site with the laparoscope.

The computing system may create a separate (e.g., independent) more complete dataset, for example, generated from and/or synthetically created and compared to the incomplete data set. The separately generated dataset may be used to ensure regularity and can be using in ML models for processing.

For example, similar datasets with similar outcomes and backgrounds may be combined into a more complete dataset for later analysis. Utilization of outcomes resulting from similar procedures, patient biomarkers, and/or predictive trend measures may be used to create directional synthetic data and/or substitution of data (e.g., to complete an incomplete dataset). This may differ from random data generation because it is based on a known and/or measured aspect of the patient, HCP, procedure, and/or outcome. The generated data may be supported by pre-established relationships of measured factors.

For example, a first patient with irregular blood sugar may be tagged with a related stress level, which may be associated with high heart rate, which may result in difficult to manage bleeding issues. A second patient may have similar difficult to managed bleeding, for example, as an event resulting from the same manger of advanced energy device usage. The second patient may not have data associated with blood sugar and/or diabetes co-morbidities. The heart rate variability may be a related measure of stress and/or pain, for example, which may be used to indicate both incomplete sets of data are resulting from stress or paint (e.g., not the blood sugar level, which may be a result, not a cause, of the stress). Both datasets may be made more complete with the measure of stress as the additional tag and/or category, for example, allowing both to be more complete and included with the analysis.

Synthetic data may be determined, for example, based on a probabilistic map of expected values from training data. A probabilistic map may be generated, for example, by running known numbers through a trained ML model and recording the data outputs as a result. The generated map may be used as a search reference, for example, to predict missing portions of data.

The ML model may compartmentalize relationships of limited datasets collected to the interrelated but isolated outcomes of sub-functions, for example, which may enable the use of the more limited dataset directly. The ML model may related the results higher into more advanced combined relationships.

The ML model may insert the generated substitute data into the dataset (e.g., to complete the dataset). The ML model may determine that the initially incomplete and/or erroneous dataset is ready for subsequent processing (e.g., complete and/or regular). The ML model may output the updated data set.

The master data set may be updated, for example, as more input data (e.g., from future surgical procedures) are fed into the ML model for processing. The ML model may learn and constantly improve with each surgical procedure dataset input to the ML model. The ML model may insert the revised dataset into the master dataset (e.g., to be used for future processing). With each iteration of processing data, the master data set may be updated and/or improved.

A validation set may be used, for example, to verify outputs (e.g., from ML models). For example, a portion of a dataset may be set aside as validation data. The validation dataset may be used on control algorithms, for example, that are generated from a cloud network and/or hospital network level cloud.

Validation datasets may be datasets that record data with a higher quality data than a standard procedure is expected to collect. Validation data sets may be generated using surgical devices in the operating room and/or using heavily instrumented devices in the operating room (e.g., non-"smart" devices, such as, for example, a thermometer that may send time stamped data to be collected with the rest of the operating room data).

Validation datasets may be confirmed and/or vetted, for example, to ensure that the correct data is received (e.g., data that falls within the bounds of expected constraints, such as, for example, patient outcomes, instrument performance, tissue performance, etc.). The validation datasets may include high quality data that may enable better analysis. The validation datasets may be cherry picked for unit tests. Certain data may be generated, such as, for example, jamming a device, and/or operating outside of standard bounds, to put into the validation data set. Devices and systems may be loaded and/or overloaded to account for possible outcomes (e.g., including failure outcomes). The validation dataset may be used to train ML models for multiple possible outcomes.

Validation datasets may be used to probe control algorithms (e.g., from other sources). For example, if a validation dataset is returned with predicted results that are different than what occurred in the procedure, the indication may be used to correct an error before deployment of the algorithm and/or a modification of the algorithm. If the validation dataset is returned with the correct predicted results from different control algorithms, an indication may be used to indicate there is a different insight due to some factor recorded in the dataset. The flagged control algorithm may be a candidate for further review to investigate why there is a difference in the controls and if the difference in the control algorithm is another way to perform the process.

A validation dataset may be created (e.g., artificially created) using a simulator and/or bench top datasets that express a known relationship of the instrument and its operation. For example, relationship data may be generated on the assembly line with defined combinations of parts leading to a specific device configuration and the resulting operational behavior. Bench top data may be generated, for example, using a user defined device and/or generator setup that may result in a device behavior that is predefined as beneficial and/or unacceptable. The unacceptable behaviors may result from a product inquiry and/or design validation testing.

Partial datasets may be used for confidence in ML model output predictions. For example, a master output may be used to check against an ML model output to confirm validation. The master output may take timing to process the (e.g., all) applicable data sets to confirm validation. For example, portions of the algorithm and/or datasets may be validated (e.g., as opposed to the entire composition of the algorithm), for example, based on a risk-based approach. The risk-based approach may expedite the results (e.g., while limited confidence in the output). The faster the output is produced may be associated with the higher the risk associated with the output.

A full master set of datasets may be created, for example, using highly instrumented procedures with exhaustive data collection and/or annotation practices (e.g., to ensure quality of data). The master dataset may be used to train the first iteration(s) of an ML model, for example, before the ML model is deployed for use in operating theaters.

Additional data may be collected for the master dataset, for example, after the deployment of the product. Additional data may be collected from controlled and/or singled out procedures that may be tooled for comprehensive data acquisition and/or labeling. System directed investigation of possible but inconclusive relationships from the original data may be performed. The additional data may be directed by a first ML model related to relationships that it identified that could have an interrelationship but the dataset was inconclusive. Targeted data collection and/or analysis may be used to seek information and/or interrelationships of a sub-portion of a primary set of information.

Preliminary relationship adjustment of some of the instruments within its reach may be used to result in minor changes in operation, for example, to monitor resulting behavior within the normal operation parameters of the device and/or subsystem to extract relationship data. For example, an RF Bipolar device may use tissue impendence and terminations of a weld. The triggering points may have a target impendence with a standard deviation that is acceptable for the triggering event to change the behavior. If the system identifies a potential relationship between the impedance value, the tissue type, the tissue thickness, and/or the resulting weld integrity, the system may direct generators that identify this set of parameters to adjust the impendence level trigger within its predefined acceptable range to one side or another side of the range (e.g., to validate or refute the potential relationship). The results may be communicated to the cloud system that may provide the resulting understanding to the other operational connected generators to further validate the result. The adjustment may be performed with micro changes that may produce (e.g., only) directional outcomes without affecting overall outcome and/or may be used to dramatically adjust the parameter to monitor larger effects.

In examples, an ML model may monitor relationships identified through a dataset to determine (e.g., with more, additional information) whether the relationships become stronger or weaker. The ML model may be enabled to re-enforce and/or adjust device control algorithms based on the initial learning.

Figure 17:
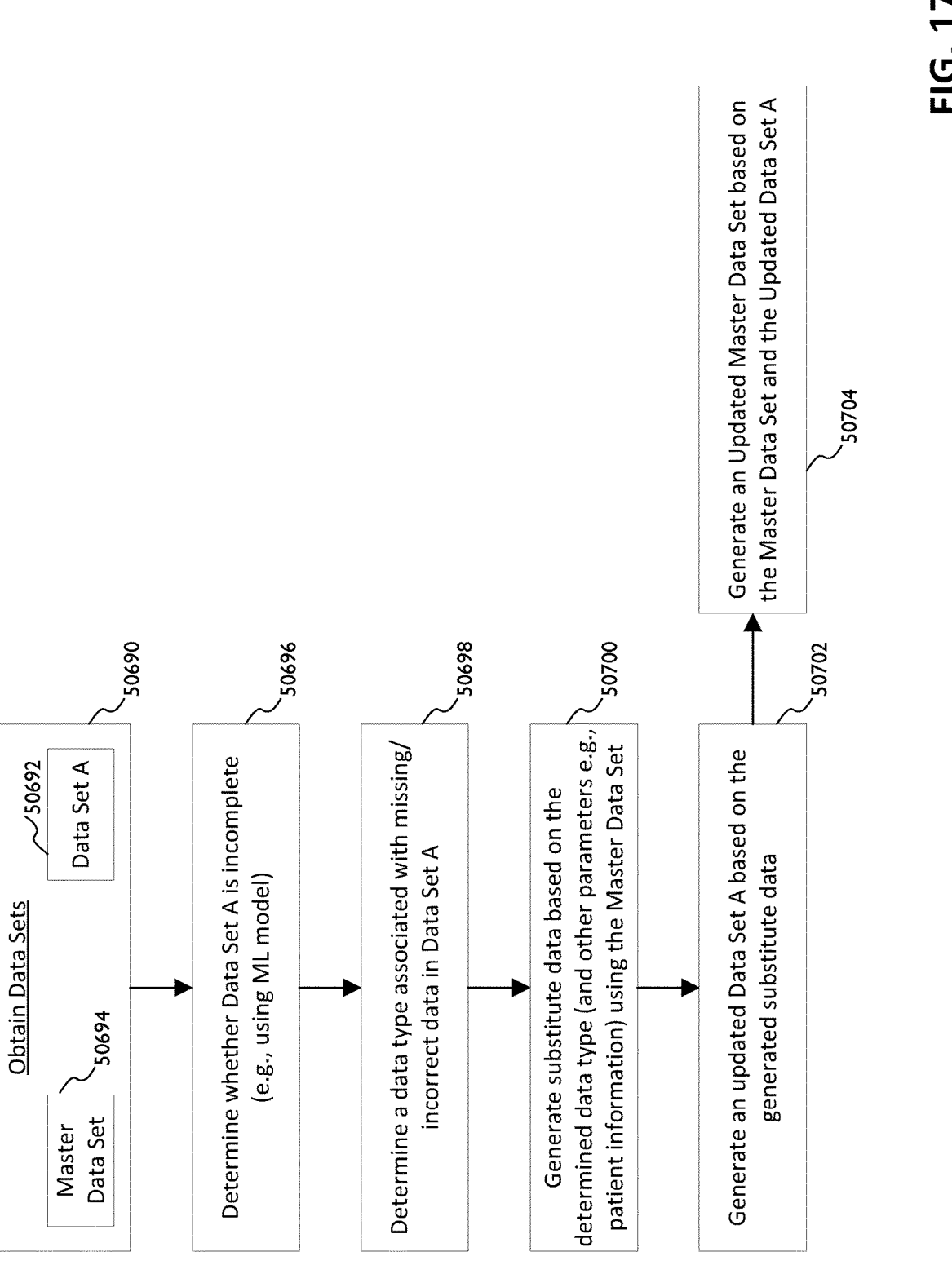
FIG. 17 illustrates an example of using a ML model to complete a dataset based on data type.

FIG. 17 illustrates an example of using a ML model to complete a dataset based on data type. As shown at 50690, surgical data sets may be obtained. The surgical data sets may include a data set to be processed (e.g., Data Set A 50692) and/or a master data set 50694. As shown at 50696, a ML model may be used to determine whether Data Set A 50692 is incomplete, irregular, and/or erroneous (e.g., as described herein). As shown at 50698, a data type associated with missing and/or incorrect data in Data Set A may be determined. As shown at 50700, substitute data (e.g., to insert in place of the missing data and/or replace the irregular and/or erroneous data) may be generated (e.g., using an ML model). As shown at 50702, Data Set A may be updated, for example, based on the generated substitute data. Additionally, the master data set may be updated (e.g., a revised master data set may be generated) based on the updated Data Set A (e.g., as shown at 50704).

The ML model may determine a data type associated with portions of data in the data set. For example, a data type may be one or more of the following: surgical instrument parameters, surgical equipment parameters, patient information, patient biomarkers, HCP information, and/or the like. For example, a data type may indicate that a piece of data is a patient biomarker, such as heart rate, for example. The ML model may determine that there is a missing portion of heart rate data during a surgical procedure. Based on the determination that the missing data is a heart rate (e.g., data type), the ML model may determine to generate substitute data of the same type (e.g., substitute heart rate data).

In examples, ML models may be used to take multiple sets of problematic (e.g., incomplete, irregular, and/or erroneous) data and generate an independent complete dataset. For example, an ML model may receive a first dataset and a second dataset. The ML model may be used to determine that the first and second datasets are problematic. The ML model may determine that the first and second datasets are problematic (e.g., incomplete, irregular, and/or erroneous), for example, based on comparison to a verified data set (e.g., master data set). The ML model may determine to aggregate the datasets and/or generate a third dataset using the first and second datasets.

The ML model may confirm that the generated independent dataset (e.g., generated based on the multiple problematic datasets) is valid for analysis. The ML model may confirm the generated independent dataset is valid for analysis, for example, based on a comparison to verified datasets and/or a master data set. The ML model may confirm that the generated independent dataset is accurate and/or reliable.

Systems, methods, and instrumentalities are disclosed for a surgical computing system with support for machine learning model interaction. Data exchange behavior between machine learning (ML) models and data storages may be determined and implemented. For example, data exchange may be determined based on privacy implications associated with a ML model and/or data storage. Data exchange may be determined based on processing goals associated with ML models.

For example, a surgical computing system may determine data exchange behaviors for ML models and processing systems. The surgical computing system may obtain surgical data. The surgical data may include subsets of surgical data. The subsets of surgical data may be associated with respective classifications (e.g., privacy classifications). For example, the respective classifications may be determined for each of the subsets of surgical data. The surgical computing system may determine processing goal(s) associated with processing systems (e.g., ML models), for example, in a hierarchy. The hierarchy may include multiple processing systems in a level-based system. The higher processing systems in the hierarchy may process non-private data. The lower processing systems may use increasingly more private data.

The surgical computing system may determine classification threshold associated with processing tasks associated with the ML models (e.g., processing systems). The processing tasks may include data preparation, reduction, analysis, and/or the like. The surgical computing system may determine whether a subset of data is above or below the classification threshold. The surgical computing system may determine data packages to send to the ML models. The data packages may be determined based on the classification threshold, processing goals, data needs, and/or the like, associated with the ML models. For example, a data package may refrain from including data that is below (e.g., or above) the classification threshold.

The classification threshold may be associated with a privacy level. For example, privacy may be balanced with processing task importance to determine data exchange and data packages. For example, private data may be refrained from being sent to a processing system associated with a minimally important processing task. However, private data may be sent to a processing system associated with an important processing task.

Data exchange between systems performing processing (e.g., ML processing) may be performed. For example, a surgical computing system may determine data sets (e.g., data packages) to be sent for processing. The surgical computing system may send discrete data packages to different processing systems based on one or more of the following: processing goals, processing location, data type, data classification, processing capability, and/or the like. Data exchange between systems may be triggered, for example, based on an event (e.g., triggering event).

Data exchange between systems may be triggered based on privacy concerns. For example, a trigger for data exchange may be limited based on privacy concerns. A trigger for data exchange may be expanded based on a processing system's data needs (e.g., integral analysis needs). The data exchange may consider both the privacy concerns and the processing system's data needs. For example, a balancing test may be performed (e.g., considering the privacy concerns and the processing system's data needs) to determine the data exchange behavior between systems. Different systems performing different processing tasks may interact, for example, to determine data exchange behavior.

Data exchange between systems may be determined, for example, to meet processing goals of different processing systems. For example, processing systems (e.g., ML models) may use different data packages to perform various processing tasks (e.g., reduction, preparation, trend analysis, recommendation determination, etc.). Data exchange between systems may enable data storage and/or data compartmentalization. For example, organization of datasets may be determined based on the use of the data for ML model usage. For example, data exchange may provide a secure data storage. Compartmentalization of data may allow for more security in the event of a data breach, for example, because the data is located in various locations. Different locations may store different levels of private data.

In examples, data exchange may enable compartmentalization in a hierarchy of data storages and/or systems that process the data. For example, a first data storage and/or first processing system (e.g., at the highest level) may receive a first data package including data associated with a minimal privacy level (e.g., not private, not confidential information, for example, as determined by HIPAA guidelines). The data received at the first data storage and/or first processing system may include non-private data and/or redacted data (e.g., data with private and/or confidential data removed). A second data storage and/or second processing system (e.g., a level below the first data storage and/or first processing system, for example, in the hierarchy) may receive a second data package. The second data package may include the data in the first data package. The second data package may include data associated with a privacy level higher than the privacy level in the first data package (e.g., the data in the second data package may have a low private information level). The second data storage and/or second processing system may be enabled to store and/or process data associated with a higher privacy level than the first data storage and/or first processing system. The second data package may be a more complete set of data as compared to the first data package.

In examples, a data storage and/or processing system in the hierarchy may be aware of the other data storages and/or processing systems in the hierarchy. The data storage and/or processing system in the hierarchy may be aware of the privacy level, processing goals, data needs, and/or the like associated with the other data storages and/or processing systems in the hierarchy. For example, a first data storage may be aware that a second data storage is associated with storing more private information as compared with the first data storage. A lower level storage (e.g., in a hierarchy) may be aware of subsequent levels in the hierarchy (e.g., processing goals and/or data storage) and/or the criticality of the patient privacy aspects associated with the subsequent levels. The lower level storage may (e.g., using the awareness of the subsequent levels in the hierarchy) determine the amount of data, data type, and/or storage location of the data. For example, a first processing system with a first processing goal and first data needs associated with the first processing goal may be aware that a second processing system is associated with a second processing goal and a second data needs associated with the second processing goal.

In examples, data classifications (e.g., privacy level classifications) may be determined for portions of surgical data. For example, privacy level classifications for data may be determined based on HIPAA boundaries and/or considerations. For example, data storages within a facility may be enabled to store private and/or confidential data. For example, data storages within an edge network (e.g., associated with a medical facility) may be enabled to store private and/or confidential data. For example, data storages in a cloud network (e.g., outside the facility network and/or edge network) may store non-private and/or non-confidential information (e.g., restricted from storing confidential information), for example, based on HIPAA guidelines.

The privacy level classifications for portions of surgical data may be compared to thresholds (e.g., privacy level thresholds) associated with data storages and/or processing systems, for example, to determine whether the portion of surgical data can be stored and/or processed at the respective data storages and/or processing systems. For example, the thresholds may be predefined (e.g., based on HIPAA boundaries). The thresholds may be used to balance privacy concerns with processing data needs, for example. For example, a data storage and/or processing system within a controlled data network may have a privacy threshold that enables receiving more private and/or confidential data. A data storage and/or processing system outside a controlled data network may have a privacy threshold that restricts receiving private and/or confidential data (e.g., receives only non-private data).

Figure 18:
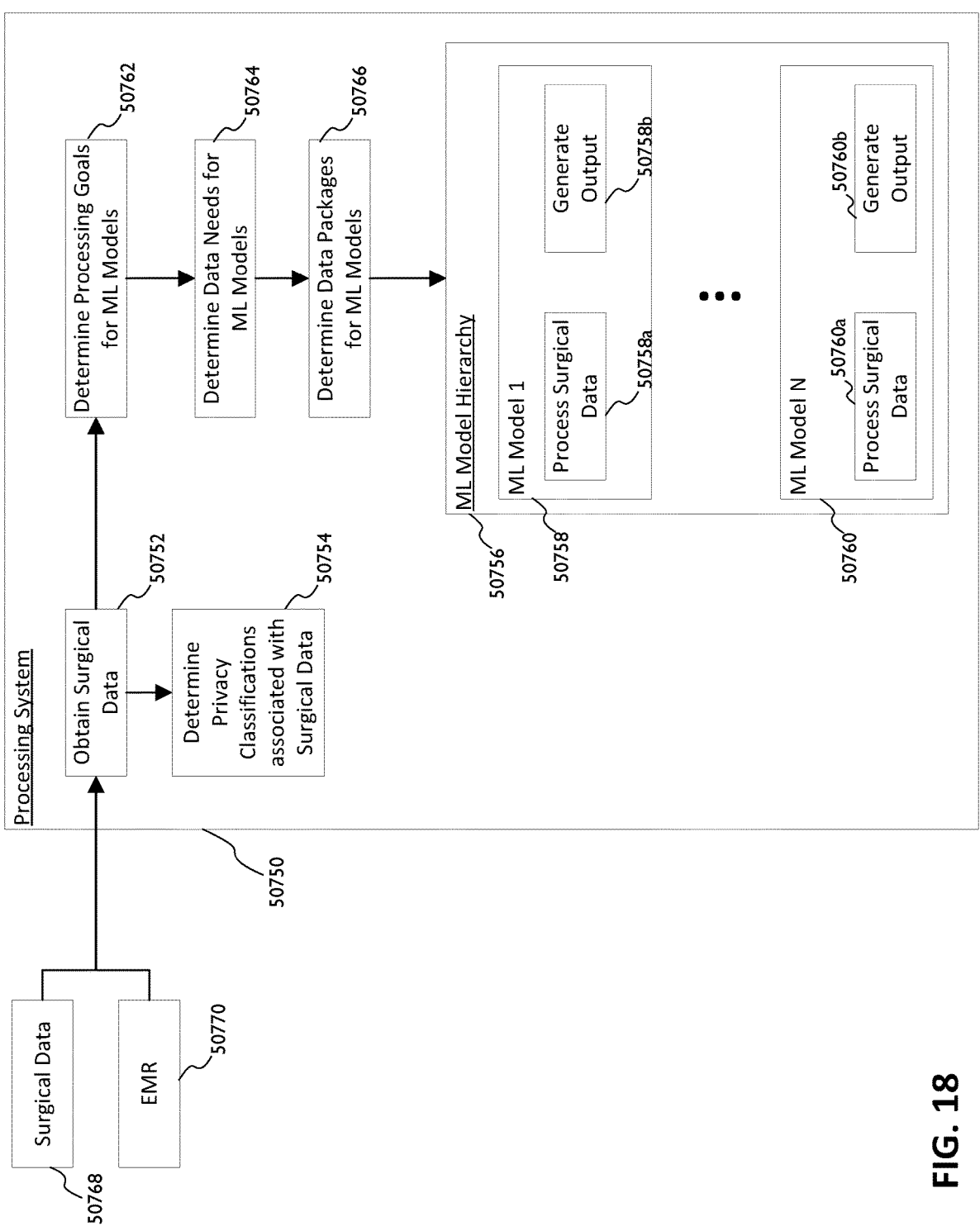
FIG. 18 illustrates an example of determining data exchange for a hierarchy of data processing systems.
Figure 19:
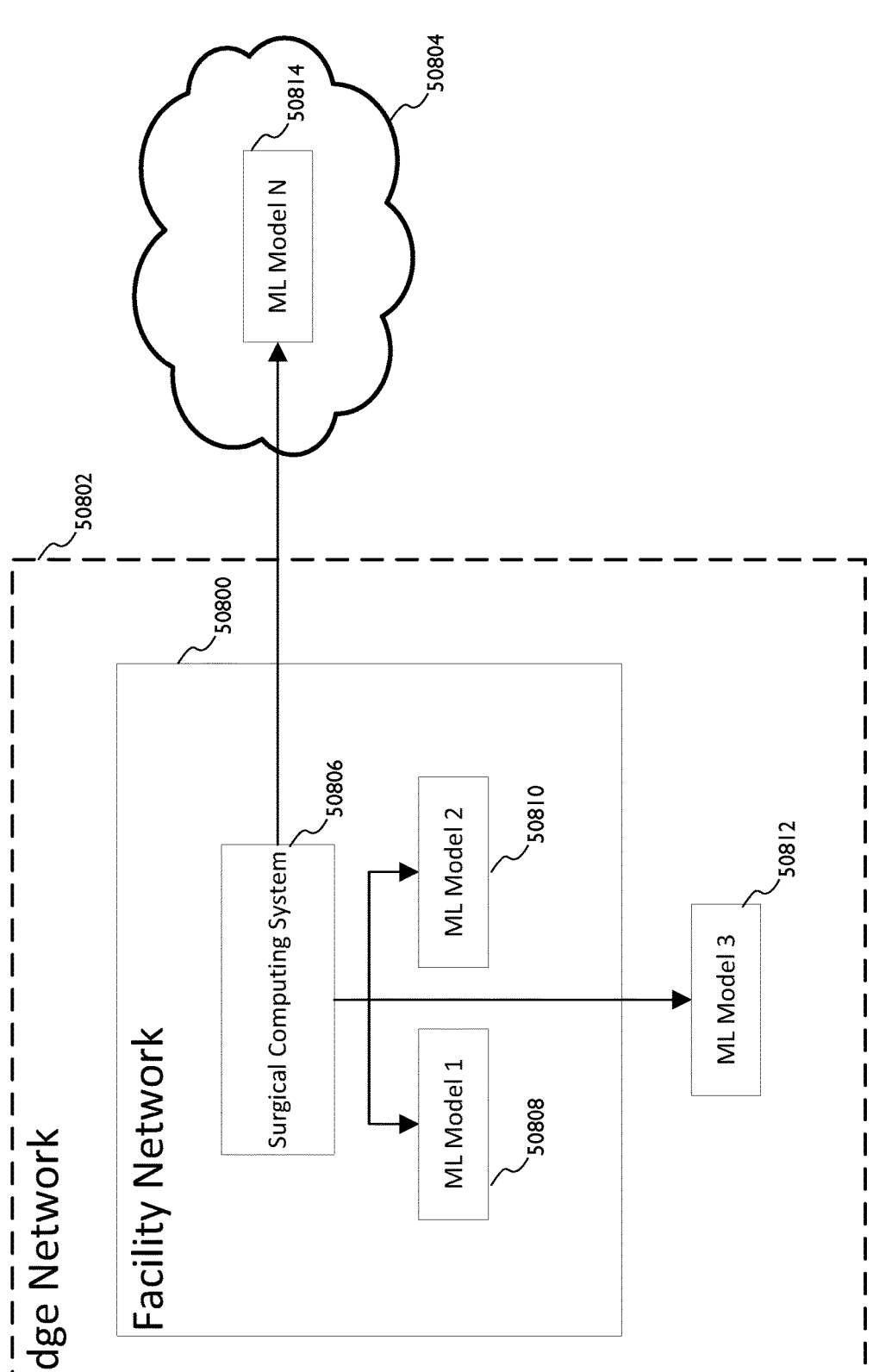
FIG. 19 illustrates example ML models in located in the facility network, edge network, and cloud network.

FIG. 18 illustrates an example of determining data exchange for a hierarchy of data processing systems. As shown in FIG. 18, a processing system (e.g., surgical processing system) 50750 may obtain surgical data (e.g., as shown at 50752) and determine data exchange behavior (e.g., for a hierarchy of data storages and/or processing systems). The processing system 50750 may determine classifications (e.g., privacy classifications) associated with the obtained surgical data (e.g., as shown at 50754 in FIG. 18). The processing system 50750 may be aware of a hierarchy of processing systems (e.g., ML models) and/or data storages. For example, the processing system 50750 may be aware of a ML model hierarchy 50756 (e.g., for processing surgical data). The ML model hierarchy 50756 may include multiple ML models (e.g., for processing data at different levels), for example, such as a first ML model

50756 and an Nth ML model 50758. The hierarchy may include data storages, for example. The ML models may be used in the processing system 50750. The ML models may be used outside the processing system 50750 (e.g., in a different processing system, for example, within the same network or outside the computing system's network). The processing system may determine processing goals associated with the ML models in the ML model hierarchy 50756 (e.g., as shown at 50762). The processing goals may be associated with data needs associated with the ML models in the ML model hierarchy 50756. The data needs associated with the ML models may be determined, for example, based on the processing goals associated with the ML models (e.g., as shown at 50764). Data packages for the ML models may be determined (e.g., as shown at 50766), for example, by the processing system. The data packages may be sent to the ML models (e.g., within the processing system or to different processing systems).

The obtained surgical data (e.g., as shown at 50752) may include surgical data 50768, electronic medical records (EMR) 50770, and/or the like. For example, the obtained surgical data may include data associated with a surgical procedure, data associated with a specific patient, data associated with similar patients, and/or the like. The obtained surgical data may be associated with a privacy level. For example, privacy levels may be determined based on HIPAA guidelines (e.g., as described herein). For example, surgical data may be determined to be private information if the data contains identifying information. Privacy classifications may include (e.g., but is not limited to) one or more of the following: not private and/or confidential, low privacy, medium privacy, high privacy, critical privacy, and/or the like. For example, portions of surgical data that are associated with data that identifies a patient may be classified with a high privacy or critical privacy level. Surgical data associated with a high privacy or critical privacy level may be refrained from being transmitted (e.g., transmitted without redaction) to a location outside the facility network and/or cloud network. Surgical data associated with a low privacy level or not private level may be enabled to be transmitted to (e.g., any) data storage and/or processing system (e.g., outside the facility and/or edge network).

Private information in surgical data may be redacted, for example, to lower the privacy concerns associated with data. For example, surgical data associated with a high privacy level may be redacted (e.g., the identifying information may be redacted), for example, so the surgical data can be classified as a lower privacy level. The redacted surgical data may conform to privacy limitations associated with a data storage and/or processing system (e.g., outside the facility and/or edge network), for example, because it does not contain the identifying information (e.g., anymore).

The processing system may determine subsets of surgical data from the obtained surgical data. For example, subsets of surgical data may be discretized portions of the obtained surgical data. The subsets of surgical data may determined, for example, based on the type of data, data format, data contents, and/or the like. For example, a subset of data may include data (e.g., only data) associated with a specific surgical instrument. A subset of data may be a table of records (e.g., with fields as columns) associated with a specific patient. A subset of data may include a particular column of data within a table of records, for example. A subset of data may include any portion of the obtained surgical data (e.g., a specific data entry in a table of data, a row of data in a table of data, a column of data in a table of data). For example, a subset of data may include data associated with a specific surgical procedure. A subset of data may include data associated with a specific surgical procedure for a specific patient, for example.

The processing system 50750 may determine respective classifications (e.g., privacy level classifications) for each determined subset of surgical data. For example, different subsets may be associated with different classifications. A first subset of data may (e.g., be determined to) contain non-private and/or non-confidential data (e.g., as determined with respect to HIPAA guidelines). The first subset of data may not have privacy implications associated with transmittal. The first subset of data may be transmitted to a data storage and/or processing system within the facility network, edge network, cloud network, and/or the like. A second subset of data may (e.g., be determined to) contain data associated with a high and/or critical privacy level classification (e.g., includes patient identifying data). The second subset of data may be subjected to restrictions on transmittal (e.g., HIPAA restrictions). For example, the second subset of data may be refrained from being sent to a data storage and/or processing system outside the facility network and/or edge network (e.g., refrained from being sent to a cloud network).

The processing system 50750 may determine processing goal(s). For example, the processing goal(s) may include an overarching processing goal (e.g., associated with a ML model hierarchy 50756). The processing goal(s) may include separate processing goals for each ML model in the ML model hierarchy. For example, a first ML model may be associated with data reduction and/or data preparation and a second ML model may be associated with trend analysis and/or the like. The ML models may perform processing tasks as described herein with respect to FIGS. 9-17.

As shown at 50764, a data needs (e.g., for each ML model) may be determined based on a determined processing goal (e.g., for each of the ML models). The data needs may include the data used (e.g., needed) to perform and/or complete the processing goal. For example, a processing goal may be data reduction to perform trend analysis. The data needs associated with the processing goal may include data used to perform the trend analysis. The data needs may consider subsequent ML models (e.g., the subsequent ML model's processing goals). For example, a first ML model may perform preprocessing and data reduction on data and a second ML model may perform trend analysis for a specific biomarker. The data needs for the first ML model may consider the data used in the second ML model.

As shown at 50766, data packages may be determined, for example, for the ML models in the ML model hierarchy 50756. Different data packages may be determined and sent to the ML models. For example, a first data package may be determined for ML Model 1 50758 and an Nth data package may be determined for ML Model N 50760. ML Model N 50760 may be the lowest level in the ML Model Hierarchy 50756. The lowest level in the ML Model Hierarchy 50756 (e.g., ML Model N 50760) may receive the most complete data package (e.g., as compared to the other data packages determined for the other ML models in the ML Model Hierarchy). For example, the lower the level in the ML Model Hierarchy, the more complete the data package may be. The more complete data packages may include more surgical data (e.g., private and/or confidential data) as compared with data packages determined for higher level ML models. The level-based system may be designed, for example, to limit private information from being sent to specific levels in the ML Model Hierarchy. For example, the lowest level ML model (e.g., only the lowest level ML model) may receive highly classified and/or private data for processing. The level-based system may provide added security precautions, for example, in the event of a data breach.

For example, the processing system may determine a first data package for a first ML model and a second data package for a second ML model. The second ML model may be a lower level ML model in the ML Model Hierarchy as compared to the first ML model. The first data package may be determined based on the data needs and/or processing goals associated with the first ML model. The second data package may be determined based on the data needs and/or processing goals associated with the second ML model. The output of the first ML model may be sent to the second ML model, for example. The first data package may be determined based on considering that the output of the first ML model will be sent to the second ML model. The second data package may include the data included in the first data package. The second data package may include at least a portion of the data included in the first data package.

The ML Model Hierarchy may include ML models outside of the processing system 50750. FIG. 18 illustrates example ML models in located in the facility network, edge network, and cloud network. For example, the ML models may process data at a different location and/or in a different processing system. For example, the processing system 50750 may be located in a medical facility (e.g., within a facility network 50800 as shown in FIG. 18 and/or within an edge network 50802 as shown in FIG. 18). The facility network may be contained within the edge network (e.g., as shown in FIG. 18). The ML Model Hierarchy may include ML models within the facility network, edge network, cloud network, and/or the like. For example, a first ML model may be located in the edge network and a second ML model may be located in the cloud network. Different privacy implications may affect the data exchange between the ML models. As shown in FIG. 18, a first ML model 50808 and a second ML model 50810 may be located in the facility network (e.g., and within the edge network). A third ML model 50812 may be located within the edge network, for example, outside the facility network. An Nth ML Model 50814 may be located in a cloud network, for example, outside the edge network. A HIPAA boundary may affect data exchange between ML Models. For example, the HIPAA boundary may restrict confidential information from being transmitted outside the edge network and/or facility network (e.g., restricted from transmitting confidential information to the cloud network). The cloud network may be outside the HIPAA boundary, for example.

The ML models may process obtained surgical data (e.g., data packages, for example, as shown at 50758a and 50760a in FIG. 18). The ML models may generate an output (e.g., as shown at 50758b and 50760b in FIG. 18). The generated outputs from the ML models may be sent to subsequent ML models (e.g., in the hierarchy). The generated outputs may be stored and/or sent to HCP for review. The generated outputs may be stored, for example, to train the ML model for subsequent inputs.

In examples, the ML models may send discretized data packages to subsequent ML models. For example, a first ML model may receive a first data package for processing. The first ML model may generate a first output based on processing the first data package. The first ML model may identify a second ML model (e.g., subsequent ML model). The first model may determine a data needs and/or processing goal associated with the second ML model. The first model may generate a second data package (e.g., to be sent to the second ML model for processing). The second data package may include at least a portion of the first output. For example, the second data package may include the entire first output. The second data package may be determined based on the privacy concerns associated with the second ML model. The second data package may be determined based on the processing capabilities associated with the second ML model. The second data package may be determined based on a balancing analysis between the processing goal and the privacy implications associated with the second ML model.

Data exchange between processing systems (e.g., ML models) may be performed, for example, based on privacy level classifications and/or processing goals for surgical data. For example, a surgical computing system may obtain surgical data (e.g., a set of surgical data). The surgical data may include at least one subset of surgical data (e.g., as described herein). The subsets of surgical data may be grouped, for example, based on data type, data format, data source, data classification (e.g., privacy classification), surgical procedure type, patient, surgical instrument, and/or the like. The surgical computing system may determine processing goal(s) associated with the surgical data. For example, the surgical computing system may determine an overarching processing goal associated with the surgical data and different processing goals associated with individual processing systems (e.g., ML models), for example, in a ML model hierarchy. The processing goal(s) may be associated with a respective data needs and/or processing task. For example, the processing goal may be achieved based on performing the processing task. For example, the processing task may be achieved based on using data fulfilling the processing task's data needs.

The surgical computing system may determine a classification threshold associated with the ML models (e.g., processing tasks associated with the ML models). For example, a classification threshold may include a privacy level threshold. In examples, a first ML model may be associated with a first privacy level threshold. The first privacy level threshold may be associated with the location and/or security associated with the ML model. For example, a ML model within the facility network may be enabled to handle and/or process data that is private and/or confidential (e.g., under HIPAA guidelines). For example, a ML model in the cloud network (e.g., outside the HIPAA boundary) may be restricted from receiving data that is classified as private and/or confidential. For example, a privacy level may be low if the data contains information that is not likely able to be used to identify confidential information (e.g., a patient's identity). A privacy level may be critical and/or high if the data is associated with information that would reveal confidential information (e.g., identifies a patient).

The classification threshold may be used to determine data packages sent to the ML models. For example, a data that is below or above the classification threshold may be refrained from being sent to the ML model associated with the classification threshold. For example, if a subset of data is determined to have a high and/or critical privacy level classification and the ML model is determined to have a classification threshold of a medium privacy level classification, the subset of data may be refrained from being sent to the ML model (e.g., because it is beyond the privacy scope of the ML model). For example, if the subset of data is determined to have a low privacy level classification and the ML model is determined to have a classification threshold of a medium privacy level classification, the subset of data may be sent to the ML model for processing.

In examples, classification thresholds associated with ML models in a ML model hierarchy may be level-based. For example, a first ML model (e.g., highest level ML model) in a ML model hierarchy may have a classification threshold associated with a zero-privacy level. The first ML model may be enabled to receive subsets of data associated with zero privacy implications (e.g., no private and/or confidential information). The first ML model may be refrained from being sent and/or receiving subsets of data with any privacy implications. Subsequent ML models (e.g., lower level models) in the ML model hierarchy may have privacy classification thresholds that are associated with receiving more private data. For example, a second ML model may be a second level in the ML model hierarchy and have a privacy level classification threshold that enables a subset of data tagged as a medium privacy level to be received by the second ML model. An Nth ML model may be the lowest level ML model in the ML model hierarchy. The Nth ML model may be associated with the most secure and private data collection and/or processing. The Nth ML model may have a privacy level threshold that enables the most private data to be received.

In examples, the classification threshold associated with ML models may be determined based on the processing goal and the privacy implications. For example, the importance of the processing goal may outweigh the privacy concerns. The classification threshold may enable more private information to be exchanged, for example, if the importance of the processing goal outweighs certain privacy concerns.

Data packages for data exchange may be determined, for example, based on the classification thresholds and/or data processing goals (e.g., data needs associated with the data processing goals). For example, data packages may be determined based on balancing privacy concerns with processing goals. A processing goal may be important, for example, to provide critical surgical procedure information regarding a patient. The processing goal's needs may outweigh privacy concerns associated with data used for the processing goal. In examples, a processing goal may be determined to have low importance and the privacy implications associated with data used to achieve the processing goals may outweigh the processing goal's needs. The data package may be determined to refrain from including the private information. The determined data package(s) may be sent to the ML models.

In examples, the surgical computing system may determine whether classifications associated with subset(s) of data are above or below a first privacy classification threshold (e.g., associated with a first ML model) and/or above or below a second privacy classification threshold (e.g., associated with a second ML model). The data packages determined for each ML model may be determined based on whether a particular subset of data has a determined classification above or below the ML model's respective privacy classification threshold. For example, a first data package may be determined to include a first portion of data that is below (e.g., or alternatively above) the first privacy classification threshold. The second data package may be determined to include a second portion of data that is below (e.g., or alternatively above) the first privacy classification threshold.

Data exchange behavior may be dynamic. For example, processing goals associated with ML models may change. The changed processing goals may affect how data is exchanged between systems (e.g., ML models). For example, a change in processing goals (e.g., in a ML model hierarchy) may be determined. Based on the change in processing goals, an updated processing goal may be determined (e.g., for a ML model). The change in processing goal in a first ML model may affect the processing goals and/or data exchange of other ML models in the ML model hierarchy.

An updated classification threshold (e.g., updated privacy classification threshold) may be determined based on the updated processing goal. Data exchange may be affected based on the updated processing goal. For example, an updated data package may be determined for a ML model based on the updated processing goal (e.g., updated data needs) and/or updated classification threshold.

What is claimed is:

1. A surgical computing system comprising:

a processor configured to:

receive surgical data comprising a plurality of subsets of surgical data;

determine a first classification for a first subset of the plurality of subsets of surgical data, wherein the first classification is associated with a first privacy level;

determine a second classification for a second subset of the plurality of subsets of surgical data, wherein the second classification is associated with a second privacy level;

determine a first processing goal and a second processing goal, wherein the first processing goal is associated with a first processing task and a first data need, and wherein the second processing goal is associated with a second processing task and a second data need;

determine a first classification threshold associated with the first processing task and a second classification threshold associated with the second processing task;

determine a first data package based on the first processing goal, the first data need, and the first classification threshold, wherein the first data package comprises at least a first portion of the surgical data, and wherein a first machine learning (ML) model is associated with processing the first data package;

determine a second data package based on the second processing goal, the second data need, and the second classification threshold, wherein the second data package comprises at least a second portion of the surgical data, wherein the second portion of the surgical data comprises the first portion of the surgical data, and wherein a second ML model is associated with processing the second data package;

determine whether the first classification for the first subset is below the first classification threshold;

based on the first classification for the first subset being below the first classification threshold, transmit the first subset as part of the first data package to a first processing system included in a facility network configured to execute the first ML model;

determine whether the second classification for the second subset is below the second classification threshold; and based on the second classification for the second subset being below the second classification threshold, transmit the second subset as part of the second data package to a second processing system that is included in a cloud network outside the facility network and is configured to execute the second ML model.

2. The surgical computing system of claim 1, wherein the processor is further configured to:

transmit the first data package to the first ML model; and transmit the second data package to the second ML model.

3. The surgical computing system of claim 1, wherein the first classification threshold is associated with the first privacy level, wherein the second classification threshold is associated with the second privacy level, and wherein the second privacy level is associated with more privacy than the first privacy level.

4. The surgical computing system of claim 1, wherein the first classification threshold is a first privacy classification threshold associated with a first location associated with the first processing task, and wherein the second classification threshold is a second privacy classification threshold associated with a second location associated with the second processing task.

5. The surgical computing system of claim 1, wherein the first processing task is performed using the first ML model, and wherein the second processing task is performed using the second ML model.

6. The surgical computing system of claim 1, wherein the first classification threshold is determined based on the first processing goal, and wherein the second classification threshold is determined based on the second processing goal.

7. The surgical computing system of claim 6, wherein the processor is configured to:

determine that the first processing goal has changed;

based on the determination that the first processing goal has changed, determine an updated first processing goal;

determine an updated first classification threshold based on the updated first processing goal;

determine a third data package based on the updated first processing goal and the updated first classification threshold;

determine an updated second processing goal based on the determination that the first processing goal has changed;

determine an updated second classification threshold based on the updated second processing goal; and determine a fourth data package based on the updated second processing goal and the updated second classification threshold.

8. A method, the method comprising:

receiving surgical data comprising a plurality of subsets of surgical data;

determining a first classification for a first subset of the plurality of subsets of surgical data, wherein the first classification is associated with a first privacy level;

determining a second classification for a second subset of the plurality of subsets of surgical data, wherein the second classification is associated with a second privacy level;

determining a first processing goal and a second processing goal, wherein the first processing goal is associated with a first processing task and a first data need, and wherein the second processing goal is associated with a second processing task and a second data need;

determining a first classification threshold associated with the first processing task and a second classification threshold associated with the second processing task;

determining a first data package based on the first processing goal, the first data need, and the first classification threshold, wherein the first data package comprises at least a first portion of the surgical data, and wherein a first machine learning (ML) model is associated with processing the first data package;

determining a second data package based on the second processing goal, the second data need, and the second classification threshold, wherein the second data package comprises at least a second portion of the surgical data, wherein the second portion of the surgical data comprises the first portion of the surgical data, and wherein a second ML model is associated with processing the second data package;

determining whether the first classification for the first subset is below the first classification threshold;

based on the first classification for the first subset being below the first classification threshold, transmitting the first subset as part of the first data package to a first processing system included in a facility network configured to execute the first ML model;

determining whether the second classification for the second subset is below the second classification threshold; and based on the second classification for the second subset being below the second classification threshold, transmitting the second subset as part of the second data package to a second processing system that is included in a cloud network outside the facility network and is configured to execute the second ML model.

9. The method of claim 8, wherein the method further comprises:

transmitting the first data package to the first ML model; and transmitting the second data package to the second ML model.

10. The method of claim 8, wherein the first classification threshold is associated with the first privacy level, wherein the second classification threshold is associated with the second privacy level, and wherein the second privacy level is associated with more privacy than the first privacy level.

11. The method of claim 8, wherein the first classification threshold is a first privacy classification threshold associated with a first location associated with the first processing task, and wherein the second classification threshold is a second privacy classification threshold associated with a second location associated with the second processing task.

12. The method of claim 8, wherein the first processing task is performed using the first ML model, and wherein the second processing task is performed using the second ML model.

13. The method of claim 8, wherein the first classification threshold is determined based on the first processing goal, and wherein the second classification threshold is determined based on the second processing goal.

14. The method of claim 8, wherein the method further comprises:

determining that the first processing goal has changed;

based on the determination that the first processing goal has changed, determining an updated first processing goal;

determining an updated first classification threshold based on the updated first processing goal;

determining a third data package based on the updated first processing goal and the updated first classification threshold;

determining an updated second processing goal based on the determination that the first processing goal has changed;

determining an updated second classification threshold based on the updated second processing goal; and determining a fourth data package based on the updated second processing goal and the updated second classification threshold.

15. A surgical computing system comprising:

a processor configured to:

receive surgical data comprising a plurality of subsets of surgical data;

determine a first classification for a first subset of the plurality of subsets of surgical data, wherein the first classification is associated with a first privacy level;

determine a second classification for a second subset of the plurality of subsets of surgical data, wherein the second classification is associated with a second privacy level;

determine a first processing goal and a second processing goal, wherein the first processing goal is associated with a first processing task and a first data need, and wherein the second processing goal is associated with a second processing task and a second data need;

determine a first privacy threshold associated with the first processing task and a second privacy threshold associated with the second processing task;

determine a first data package based on the first processing goal, the first data need, and the first privacy threshold, wherein the first data package comprises at least a first portion of the surgical data, and wherein a first machine learning (ML) model is associated with processing the first data package;

determine a second data package based on the second processing goal, the second data need, and the second privacy threshold, wherein the second data package comprises at least a second portion of the surgical data, wherein the second portion of the surgical data comprises the first portion of the surgical data, and wherein a second ML model is associated with processing the second data package;

determine whether the first classification for the first subset is below the first privacy threshold;

based on the first classification for the first subset being below the first privacy threshold, transmit the first subset as part of the first data package to a first processing system included in a facility network configured to execute the first ML model;

determine whether the second classification for the second subset is below the second privacy threshold; and based on the second classification for the second subset being below the second privacy threshold, transmit the second subset as part of the second data package to a second processing system that is included in a cloud network outside the facility network and is configured to execute the second ML model.

* * * * *